US012194057B2

(12) United States Patent
Mahajan

(10) Patent No.: US 12,194,057 B2
(45) Date of Patent: Jan. 14, 2025

(54) NXTAR-DERIVED OLIGONUCLEOTIDES AND USES THEREOF

(71) Applicant: Nupam Mahajan, St. Louis, MO (US)

(72) Inventor: Nupam Mahajan, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 17/554,274

(22) Filed: Dec. 17, 2021

(65) Prior Publication Data

US 2022/0193110 A1 Jun. 23, 2022

Related U.S. Application Data

(60) Provisional application No. 63/126,916, filed on Dec. 17, 2020.

(51) Int. Cl.
*A61K 31/713* (2006.01)
*A61K 31/506* (2006.01)
*A61P 35/00* (2006.01)

(52) U.S. Cl.
CPC .......... *A61K 31/713* (2013.01); *A61K 31/506* (2013.01); *A61P 35/00* (2018.01)

(58) Field of Classification Search
CPC ............................ A61K 31/713; A61K 31/506
See application file for complete search history.

(56) References Cited

U.S. PATENT DOCUMENTS 8,957,042 B2 2/2015 Safe et al.
10,017,478 B2 7/2018 Mahajan et al.
2003/0219770 A1* 11/2003 Eshleman ............ C12Q 1/6869 435/6.14
2005/0164970 A1 7/2005 Li
2011/0229408 A1 9/2011 Ain et al.
2015/0191722 A1* 7/2015 Krieg .................. A61K 47/543 435/375
2015/0225722 A1 8/2015 Ozsolak
2019/0212343 A1 7/2019 Mahajan
2020/0179435 A1* 6/2020 Revenko ................. A61P 35/00
2020/0318196 A1 10/2020 Iyer et al.

FOREIGN PATENT DOCUMENTS

CN 109718241 A 5/2019
WO WO-0216620 A2 * 2/2002 ............ C12N 15/63
WO WO-2012065051 A1 * 5/2012 ........... C12N 15/111
WO WO 2019/067210 A1 4/2019

OTHER PUBLICATIONS

Kim et al (Cell Reports 25, 2808-2820, 2018) (Year: 2018).*
Buck et al., (Biotechniques, 1999, 27:528-536) (Year: 1999).*
GenBank Accession AL356358.19 (Year: 2015).*
Abdelmohsen et al. (2013) Senescence-associated lncRNAs: senescence-associated long noncoding RNAs. Aging Cell. vol. 12, No. 5, pp. 890-900.
Antonarakis et al. (2014) AR-V7 and resistance to enzalutamide and abiraterone in prostate cancer. N Engl J Med. vol. 371, pp. 1028-1038.
Arora et al. (2013) Glucocorticoid receptor confers resistance to antiandrogens by bypassing androgen receptor blockade. Cell. vol. 155, No. 6, pp. 1309-1322.
Attard (2018) Abiraterone Alone or in Combination With Enzalutamide in Metastatic Castration-Resistant Prostate Cancer With Rising Prostate-Specific Antigen During Enzalutamide Treatment. J Clin Oncol. vol. 36, No. 25, pp. 2639-2646.
Boyer et al. (2004) The SANT domain: a unique histone-tail-binding module? Nat Rev Mol Cell Bio. vol. 5, 6 pages.
Buchwald et al. (2013) SIAH ubiquitin ligases target the nonreceptor tyrosine kinase ACK1 for ubiquitinylation and proteasomal degradation. Oncogene. vol. 32, pp. 4913-4920.
Chu et al. (2016) Understanding RNA-Chromatin Interactions Using Chromatin Isolation by RNA Purification (ChIRP). Methods Mol Biol. vol. 1480, pp. 115-123.
Consortium et al. (2012) An integrated encyclopedia of DNA elements in the human genome. Nature. vol. 489, pp. 57-74.
Dehm et al. (2008) Splicing of a novel androgen receptor exon generates a constitutively active androgen receptor that mediates prostate cancer therapy resistance. Cancer Res. vol. 68, No. 13, pp. 5469-5477.
Fizazi et al. (2017) Abiraterone plus Prednisone in Metastatic, Castration-Sensitive Prostate Cancer. N Engl J Med. vol. 377, pp. 352-360.
Flippot et al. (2019) Long non-coding RNAs in genitourinary malignancies: a whole new world. Nat Rev Urol. vol. 16, No. 8, pp. 484-504.
Gupta et al. (2010) Long non-coding RNA Hotair reprograms chromatin state to promote cancer metastasis. Nature. vol. 464, pp. 1071-1076.
Hung et al. (2011) Extensive and coordinated transcription of noncoding RNAs within cell-cycle promoters. Nat Genet. vol. 43, No. 7, pp. 621-629.
Hussain et al. (2018) Enzalutamide in Men with Nonmetastatic, Castration-Resistant Prostate Cancer. N Engl J Med. vol. 378, pp. 2465-2474.
Iyer et al. (2015) The landscape of long noncoding RNAs in the human transcriptome. Nat Genet. vol. 47, No. 3, pp. 199-208.

(Continued)

*Primary Examiner* — Richard A Schnizer

(57) ABSTRACT

Among the various aspects of the present disclosure is the provision of a NXTAR-derived oligonucleotides and uses thereof. An aspect of the present disclosure provides for a method of (i) suppressing androgen receptor (AR) expression, (ii) suppressing androgen receptor splice variants (including AR-V7) expression, (iii) treating cancer (e.g., prostate, breast, testis, ovarian, endometrial and skin) (iv) treating skin related diseases, such as androgenetic alopecia and acne vulgaris in a subject comprising administering to the subject a NXTAR-derived oligonucleotide (oligo) (NXTAR is a lncRNA also known as LOC105373241).

6 Claims, 48 Drawing Sheets

Specification includes a Sequence Listing.

(56) References Cited

OTHER PUBLICATIONS

Kapranov et al. (2007) RNA Maps Reveal New RNA Classes and a Possible Function for Pervasive Transcription. Science. vol. 316, No. 5830, pp. 1484-1488.
Karmodiya et al. (2012) H3K9 and H3K14 acetylation co-occur at many gene regulatory elements, while H3K14ac marks a subset of inactive inducible promoters in mouse embryonic stem cells. BMC Genomics. vol. 13, No. 424, 18 pages.
Katayama et al. (2005) Antisense Transcription in the Mammalian Transcriptome. Science. vol. 309, No. 5740, pp. 1564-1566.
Kim et al. (2020) ACK1-AR and AR-HOXB13 signaling axes: epigenetic regulation of lethal prostate cancers. NAR Cancer. vol. 2, No. 3, 13 pages.
Lawrence et al. (2015) Development of novel ACK1/TNK2 inhibitors using a fragment-based approach. J Med Chem. vol. 58, No. 6, pp. 2746-2763.
Lingadahalli et al. (2018) Novel lncRNA LINC00844 Regulates Prostate Cancer Cell Migration and Invasion through AR Signaling. Mol Cancer Res. vol. 16, No. 12, pp. 1865-1878.
Lonergan et al. (2011) Androgen receptor signaling in prostate cancer development and progression. J Carcinog. vol. 10, No. 20, 23 pages.
Lopez et al. (2016) Nuclear Receptor Corepressor Expression and Output Declines with Prostate Cancer Progression. Clin Cancer Res. vol. 22, No. 15, pp. 3937-3949.
Lu et al. (2020) Androgen receptor variant-driven prostate cancer II: advances in laboratory investigations. Prostate Cancer Prostatic Dis. vol. 23, No. 3, pp. 381-397.
Luo et al. (2019) LncRNA-p21 alters the anti-androgen enzalutamide-induced prostate cancer neuroendocrine differentiation via modulating the EZH2/STAT3 signaling. Nature Communications. vol. 10, No. 2571, 17 pages.
Mahajan et al. (2005) Activated tyrosine kinase Ack1 promotes prostate tumorigenesis: role of Ack1 in polyubiquitination of tumor suppressor Wwox. Cancer Res. vol. 65, No. 22, pp. 10514-10523.
Mahajan et al. (2007) Activated Cdc42-associated kinase Ack1 promotes prostate cancer progression via androgen receptor tyrosine phosphorylation. Proc Natl Acad Sci USA. vol. 104, No. 20, pp. 8438-8443.
Mahajan et al. (2010) Shepherding AKT and androgen receptor by Ack1 tyrosine kinase. J Cell Physiol. vol. 224, No. 2, pp. 327-333.
Mahajan et al. (2010) Effect of Ack1 tyrosine kinase inhibitor on ligand-independent androgen receptor activity. Prostate. vol. 70, No. 12, pp. 1274-1285.
Mahajan et al. (2010) Ack1 mediated AKT/PKB tyrosine176 phosphorylation regulates its activation. PLoS One. vol. 5, No. 3, e9646, 17 pages.
Mahajan et al. (2012) PI3K-independent AKT activation in cancers: a treasure trove for novel therapeutics. J Cell Physiol. vol. 227, No. 9, pp. 3178-3184.
Mahajan et al. (2012) Ack1-mediated androgen receptor phosphorylation modulates radiation resistance in castration-resistant prostate cancer. J Biol Chem. vol. 287, No. 26, pp. 22112-22122.
Mahajan et al. (2012) H2B Tyr37 phosphorylation suppresses expression of replication-dependent core histone genes. Nat Struct Mol Biol. vol. 19, No. 9, pp. 930-937.
Mahajan et al. (2015) ACK1/TNK2 tyrosine kinase: molecular signaling and evolving role in cancers. Oncogene. vol. 34, No. 32, pp. 4162-4167.
Mahajan et al. (2017) ACK1/TNK2 Regulates Histone H4 Tyr88-phosphorylation and AR Gene Expression in Castration-Resistant Prostate Cancer. Cancer Cell, vol. 31, No. 6, pp. 790e8-803e8.
Mahajan et al. (2018) Blockade of ACK1/TNK2 To Squelch the Survival of Prostate Cancer Stem-like Cells. Sci Rep. vol. 8, No. 1954, 10 pages.
Mahendrarajah et al. (2016) Histone deacetylase inhibitors induce proteolysis of activated CDC42-associated kinase-1 in leukemic cells. J Cancer Res Clin Oncol. vol. 142, No. 11, pp. 2263-2273.
Mahendrarajah et al. (2017) HSP90 is necessary for the ACK1-dependent phosphorylation of STAT1 and STAT3. Cell Signal. vol. 39, pp. 9-17.
Malik et al. (2014) The lncRNA PCAT29 inhibits oncogenic phenotypes in prostate cancer. Mol Cancer Res. vol. 12, No. 8, pp. 1081-1087.
Margueron et al. (2011) The Polycomb complex PRC2 and its mark in life. Nature. vol. 469, No. 7330, pp. 343-349.
Masumi et al. (1999) The histone acetylase PCAF is a phorbol-ester-inducible coactivator of the IRF family that confers enhanced interferon responsiveness. Mol Cell Biol. vol. 19, No. 3, pp. 1810-1820.
Masumi (2011) Histone acetyltransferases as regulators of nonhistone proteins: the role of interferon regulatory factor acetylation on gene transcription. J Biomed Biotechnol. vol. 2011, No. 640610, 6 pages.
Misawa et al. (2017) Long non-coding RNAs and prostate cancer. Cancer Sci. vol. 108, No. 11, pp. 2107-2114.
Mu et al. (2017) SOX2 promotes lineage plasticity and antiandrogen resistance in TP53- and RB1-deficient prostate cancer. Science. vol. 355, No. 6320, pp. 84-88.
Nagy et al. (2007) Distinct GCN5/PCAF-containing complexes function as coactivators and are involved in transcription factor and global histone acetylation. Oncogene. vol. 26, No. 37, pp. 5341-5357.
Parolia et al. (2015) The long non-coding RNA PCGEM1 is regulated by androgen receptor activity in vivo. Molecular Cancer. vol. 14, No. 46, 7 pages.
Quigley et al. (2018) Genomic Hallmarks and Structural Variation in Metastatic Prostate Cancer. Cell. vol. 174, No. 3, pp. 758-769e9.
Quinn et al. (2016) Unique features of long non-coding RNA biogenesis and function. Nature Reviews Genetics. vol. 17, pp. 47-62.
Ramnarine et al. (2019) The evolution of long noncoding RNA acceptance in prostate cancer initiation, progression, and its clinical utility in disease management. Eur Urol. vol. 76, No. 5, pp. 546-559.
Rossi et al. (2014) LncRNAs: New Players in Apoptosis Control. Int J Cell Biol. vol. 2014, No. 473857, 7 pages.
Sakurai et al. (2015) The lncRNA DRAIC/PCAT29 Locus Constitutes a Tumor-Suppressive Nexus. Mol Cancer Res. vol. 13, No. 5, pp. 828-838.
Scher et al. (2004) Targeting the androgen receptor: improving outcomes for castration-resistant prostate cancer. Endocr Relat Cancer. vol. 11, No. 3, pp. 459-476.
Sharma et al. (2013) The Androgen Receptor Induces a Distinct Transcriptional Program in Castration-Resistant Prostate Cancer in Man. Cancer cell. vol. 23, No. 1, pp. 35-47.
Shih et al. (2015) Non-Coding RNAs in Castration-Resistant Prostate Cancer: Regulation of Androgen Receptor Signaling and Cancer Metabolism. Int J Mol Sci. vol. 16, No. 12, pp. 28943-28978.
Siegel et al. (2020) Cancer statistics, 2020. CA: A Cancer Journal for Clinicians. vol. 70, No. 1, pp. 7-30.
Sweeney et al. (2015) Chemohormonal Therapy in Metastatic Hormone-Sensitive Prostate Cancer. N Engl J Med. vol. 373, pp. 737-746.
Ta et al. (2019) Discovery of a novel long noncoding RNA overlapping the LCK gene that regulates prostate cancer cell growth. Mol Cancer. vol. 18, No. 113, 15 pages.
Takayama et al. (2013) Androgen-responsive long noncoding RNA CTBP1-AS promotes prostate cancer. EMBO J. vol. 32, No. 12, pp. 1665-1680.
Takeda et al. (2018) A Somatically Acquired Enhancer of the Androgen Receptor Is a Noncoding Driver in Advanced Prostate Cancer. Cell. vol. 174, No. 2, pp. 422e13-432e13.
Viswanathan et al. (2018) Structural Alterations Driving Castration-Resistant Prostate Cancer Revealed by Linked-Read Genome Sequencing. Cell. vol. 174, No. 2, pp. 433e19-447e19.
Watson et al. (2015) Emerging mechanisms of resistance to androgen receptor inhibitors in prostate cancer. Nature Reviews Cancer. vol. 15, No. 12, pp. 701-711.
Wu et al. (2017) The non-receptor tyrosine kinase TNK2/ACK1 is a novel therapeutic target in triple negative breast cancer. Oncotarget. vol. 8, No. 2, pp. 2971-2983.

(56) References Cited

OTHER PUBLICATIONS

Xiao et al. (2018) Epigenetic Reprogramming with Antisense Oligonucleotides Enhances the Effectiveness of Androgen Receptor Inhibition in Castration-Resistant Prostate Cancer. Cancer Res. vol. 78, No. 20, pp. 5731-5740.
Yamamoto et al. (2015) Generation 2.5 antisense oligonucleotides targeting the androgen receptor and its splice variants suppress enzalutamide-resistant prostate cancer cell growth. vol. 21, No. 7, pp. 1675-1687.
Yang et al. (2013) IncRNA-dependent mechanisms of androgen-receptorregulated gene activation programs. Nature. vol. 500, No. 7464, pp. 598-602.
Yousefi et al. (2019) Long noncoding RNAs and exosomal IncRNAs: classification, and mechanisms in breast cancer metastasis and drug resistance. Oncogene. vol. 39, No. 5, pp. 953-974.
Yu et al. (2003) A SANT motif in the SMRT corepressor interprets the histone code and promotes histone deacetylation. EMBO J. vol. 22, No. 13, pp. 3403-3410.
Yu et al. (2010) An integrated network of androgen receptor, polycomb, and TMPRSS2-ERG gene fusions in prostate cancer progression. Cancer cell. vol. 17, No. 5, pp. 443-454.
Yuan et al. (2013) Androgen receptor functions in castration-resistant prostate cancer and mechanisms of resistance to new agents targeting the androgen axis. Oncogene. vol. 33, No. 22, pp. 2815-2825.
Zhai et al. (2017) LncRNA-SARCC suppresses renal cell carcinoma (RCC) progression via altering the androgen receptor(AR)/miRNA-143-3p signals. Cell Death Differ. vol. 24, No. 9, pp. 1502-1517.
Zhang et al. (2018) Analysis of the androgen receptor-regulated IncRNA landscape identifies a role for ARLNC1 in prostate cancer progression. Nat Genet. vol. 50, pp. 814-824.
Zhao et al. (2015) Long Noncoding RNAs: A New Regulatory Code in Metabolic Control. Trends Biochem Sci. vol. 40, No. 10, pp. 586-596.
Zhao et al. (2021) Identification of IncRNA-Protein Interactions by CLIP and RNA Pull-Down Assays. Methods Mol Biol., vol. 2021, No. 2348, pp. 231-242.

* cited by examiner

VCaP tumor Xenografts

FIG. 7A
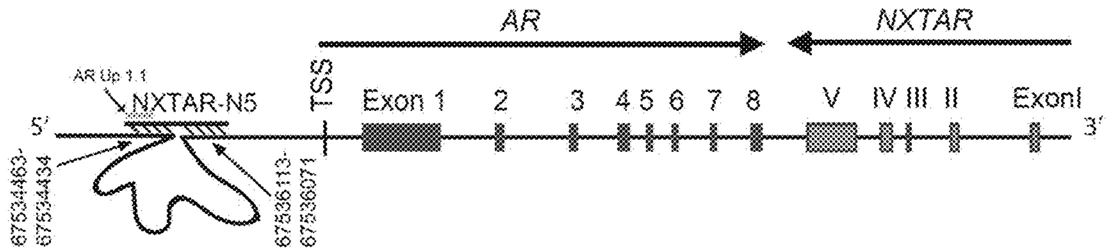
FIG. 7B
```
NXTAR(67783848)   ATTATTATTTTAAATTTACAGAAGGGGAAA  (67783877)
                  ||||||||||| | |||||||| | |||||
AR(67534463)      ATTATTATTTTTATTTTACAGATGAGGAAA  (67534434)

NXTAR(67783865)   ACAGAAGGGGAAACTAAGAATTATAGACATGAAGTGACTCACC  (67783907)
                  |||| || ||||||| || |    | |  | ||||||||||||
AR(67536113)      ACAGGAGAGGAAACTGAGCCTCTGAAAGCTTAAGTGACTCACC  (67536071)
```
FIG. 7C
NXTAR-N5 Oligonucleotide
5′ A*T*T*ATTATTTTAAATTTACAGAAGGGGAAACTAAGAATTATAGACATGAAGTGACTC*A*C*C 3′
FIG. 7D
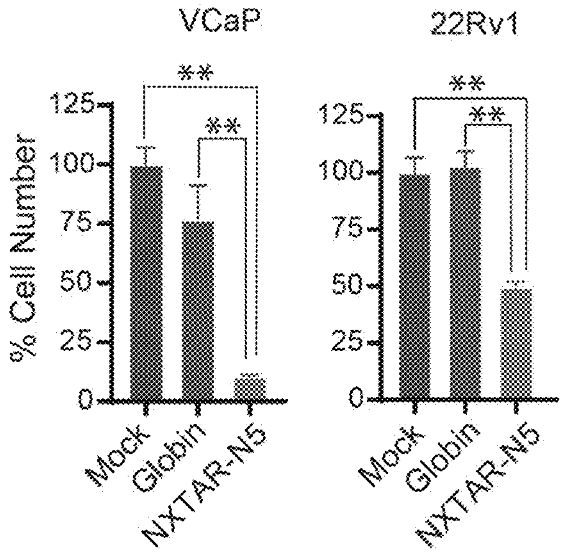

H3K4me3 Histone ChIP-seq of LNCaP clone at -3 kb to +2 kb from AR gene start

H3K4me3 Histone ChIP-seq of LNCaP clone at -3 kb to +2 kb from NXTAR gene start

FIG. 12

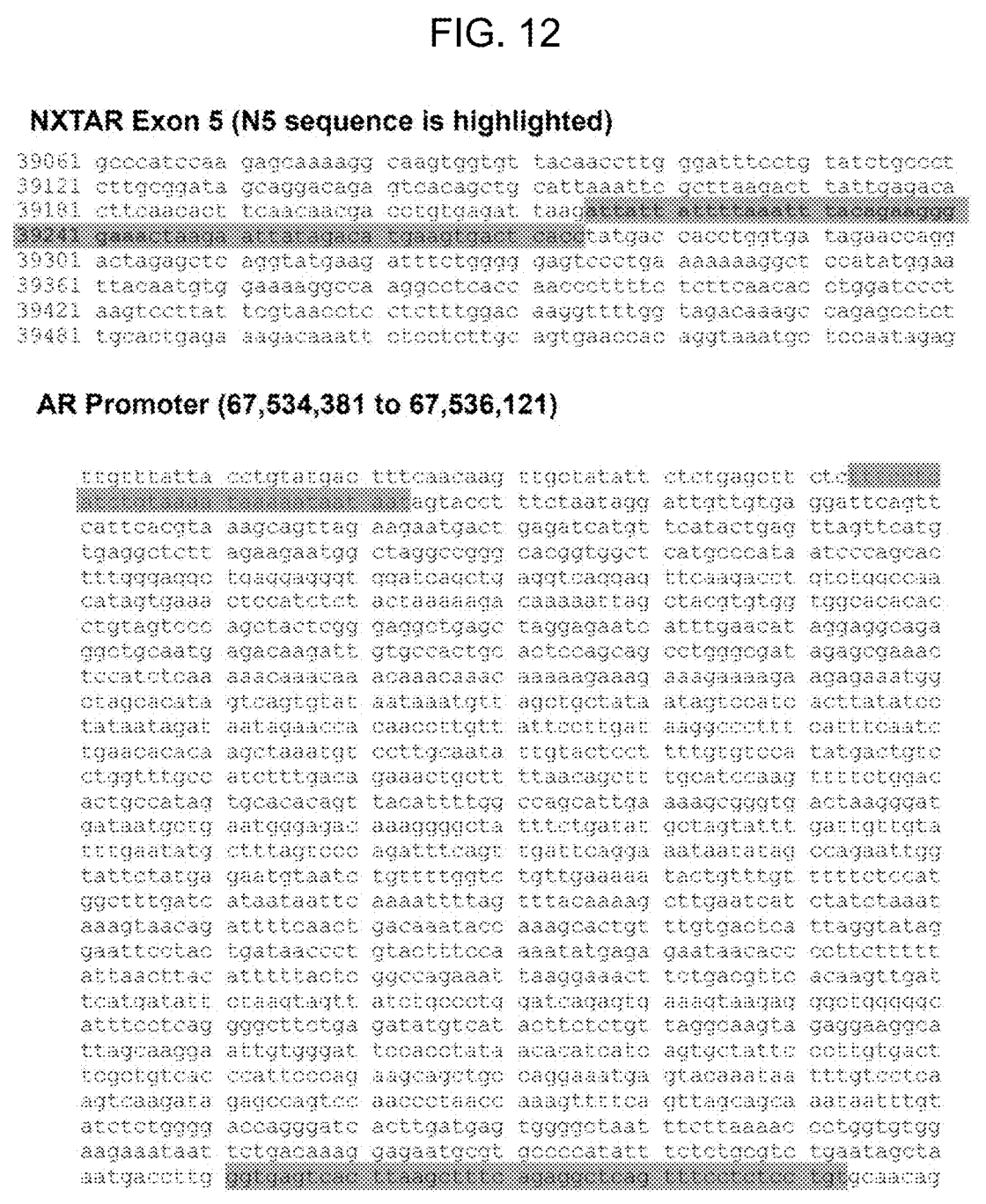

NXTAR Exon 5 (N5 sequence is highlighted)

39061 gcccatccaa gagcaaaagg caagtggtgt tacaaccttg ggatttcctg tatctgccct
39121 cttgcggata gcaggacaga gtcacagctg cattaaattc gcttaagact tattgagaca
39181 cttcaacact tcaacaacga cctgtgagat taag[illegible]
39241 [illegible]tatgac cacctggtga tagaaccagg
39301 actagagctc aggtatgaag atttctgggg gagtccctga aaaaaaggct ccatatggaa
39361 ttacaatgtg gaaaaggcca aggcctcacc aaccctttc tcttcaacac ctggatccct
39421 aagtccttat tcgtaacctc ctctttggac aaggttttgg tagacaaagc cagagcctct
39481 tgcactgaga aagacaaatt ctcctcttgc agtgaaccac aggtaaatgc tccaatagag

AR Promoter (67,534,381 to 67,536,121)

ttgtttatta cctgtatgac tttcaacaag ttgctatatt ctctgagctt ctc[illegible]
[illegible]agtacct ttctaatagg attgttgtga ggattcagtt
cattcacgta aagcagttag aagaatgact gagatcatgt tcatactgag ttagttcatg
tgaggctctt agaagaatgg ctaggccggg cacggtggct catgcccata atcccagcac
tttgggaggc tgaggagggt ggatcagctg aggtcaggag ttcaagacct gtctggccaa
catagtgaaa ctccatctct actaaaaaga caaaaattag ctacgtgtgg tggcacacac
ctgtagtccc agctactcgg gaggctgagc taggagaatc atttgaacat aggaggcaga
ggctgcaatg agacaagatt gtgccactgc actccagcag cctgggcgat agagcgaaac
tccatctcaa aaacaaacaa acaaacaaac aaaaagaaag aaagaaaaga agagaaatgg
ctagcacata gtcagtgtat aataaatgtt agctgctata atagtccatc acttatatcc
tataatagat aatagaacca caacccttgtt attccttgat aaggcccttt catttcaatc
tgaacacaca agctaaatgt ccttgcaata ttgtactcct tttgtgtcca tatgactgtc
ctggtttgcc atctttgaca gaaactgctt ttaacagctt tgcatccaag ttttctggac
actgccatag tgcacacagt tacattttgg ccagcattga aaagcgggtg actaagggat
gataatgctg aatgggagac aaaggggcta tttctgatat gctagtattt gattgttgta
tttgaatatg ctttagtccc agatttcagt tgattcagga aataatatag ccagaattgg
tattctatga gaatgtaatc tgttttggtc tgttgaaaaa tactgtttgt ttttctccat
ggctttgatc ataataattc aaaattttag tttacaaaag cttgaatcat ctatctaaat
aaagtaacag attttcaact gacaaatacc aaagcactgt ttgtgactca ttaggtatag
gaattcctac tgataaccct gtactttcca aaatatgaga gaataacacc ccttcttttt
attaacttac atttttactc ggccagaaat taaggaaact tctgacgttc acaagttgat
tcatgatatt ctaagtagtt atctgccctg gatcagagtg aaagtaagag ggctggggc
atttcctcag gggcttctga gatatgtcat acttctctgt taggcaagta gaggaaggca
ttagcaagga attgtgggat tccacctata acacatcatc agtgctattc ccttgtgact
tcgctgtcac ccattcccag aagcagctgc caggaaatga gtacaaataa tttgtcctca
agtcaagata gagccagtcc aaccctaacc aaagttttca gttagcagca aataatttgt
atctctgggg accagggatc acttgatgag tggggctaat ttcttaaaac cctggtgtgg
aagaaataat tctgacaaag gagaatgcgt gccccatatt tctctgcgtc tgaatagcta
aatgaccttg [illegible]gcaacag

SEQUENCE LISTING

```
<160> NUMBER OF SEQ ID NOS: 60

<210> SEQ ID NO 1
<211> LENGTH: 60
<212> TYPE: DNA
<213> ORGANISM: Artificial Sequence
<220> FEATURE:
<223> OTHER INFORMATION: synthetic oligo NXTAR-N5
<220> FEATURE:
<221> NAME/KEY: modified_base
<222> LOCATION: (1)..(4)
<223> OTHER INFORMATION: phosphorothioate linkage
<220> FEATURE:
<221> NAME/KEY: modified_base
<222> LOCATION: (57)..(60)
<223> OTHER INFORMATION: phosphorothioate linkage

<400> SEQUENCE: 1

attattattt taaatttaca gaaggggaaa ctaagaatta tagacatgaa gtgactcacc     60


<210> SEQ ID NO 2
<211> LENGTH: 30
<212> TYPE: DNA
<213> ORGANISM: Artificial Sequence
<220> FEATURE:
<223> OTHER INFORMATION: synthetic oligo, NXTAR-N7

<400> SEQUENCE: 2

attattattt taaatttaca gaaggggaaa                                      30


<210> SEQ ID NO 3
<211> LENGTH: 43
<212> TYPE: DNA
<213> ORGANISM: Artificial Sequence
<220> FEATURE:
<223> OTHER INFORMATION: synthetic oligo, NXTAR-N8

<400> SEQUENCE: 3

acagaagggg aaactaagaa ttatagacat gaagtgactc acc                       43
```

-continued

<210> SEQ ID NO 4
<211> LENGTH: 33
<212> TYPE: DNA
<213> ORGANISM: Artificial Sequence
<220> FEATURE:
<223> OTHER INFORMATION: synthetic oligo, NXTAR-N9

<400> SEQUENCE: 4
ccaccactag ggtcctggct acaactggcc ctc 33

<210> SEQ ID NO 5
<211> LENGTH: 33
<212> TYPE: DNA
<213> ORGANISM: Artificial Sequence
<220> FEATURE:
<223> OTHER INFORMATION: synthetic oligo, NXTAR-N9 modified
<220> FEATURE:
<221> NAME/KEY: modified_base
<222> LOCATION: (1)..(4)
<223> OTHER INFORMATION: phosphorothioate linkage
<220> FEATURE:
<221> NAME/KEY: modified_base
<222> LOCATION: (30)..(33)
<223> OTHER INFORMATION: phosphorothioate linkage

<400> SEQUENCE: 5
ccaccactag ggtcctggct acaactggcc ctc 33

<210> SEQ ID NO 6
<211> LENGTH: 60
<212> TYPE: DNA
<213> ORGANISM: Artificial Sequence
<220> FEATURE:
<223> OTHER INFORMATION: synthetic oligo, Prancer-N5
<220> FEATURE:
<221> NAME/KEY: modified_base
<222> LOCATION: (1)..(4)
<223> OTHER INFORMATION: phosphorothioate linkage
<220> FEATURE:
<221> NAME/KEY: modified_base
<222> LOCATION: (57)..(60)
<223> OTHER INFORMATION: phosphorothioate linkage

<400> SEQUENCE: 6
attattattt taaatttaca gaaggggaaa ctaagaatta tagacatgaa gtgactcacc 60

<210> SEQ ID NO 7
<211> LENGTH: 60
<212> TYPE: DNA
<213> ORGANISM: Artificial Sequence
<220> FEATURE:
<223> OTHER INFORMATION: synthetic oligo, Prancer-N5-Forward

<400> SEQUENCE: 7
attattattt taaatttaca gaaggggaaa ctaagaatta tagacatgaa gtgactcacc 60

<210> SEQ ID NO 8
<211> LENGTH: 60
<212> TYPE: DNA
<213> ORGANISM: Artificial Sequence
<220> FEATURE:
<223> OTHER INFORMATION: synthetic oligo, Prancer-N5-Reverse

<400> SEQUENCE: 8
ggtgagtcac ttcatgtcta taattcttag tttccccttc tgtaaattta aaataataat 60

<210> SEQ ID NO 9
<211> LENGTH: 30

<212> TYPE: DNA
<213> ORGANISM: Artificial Sequence
<220> FEATURE:
<223> OTHER INFORMATION: synthetic oligo, N7
<220> FEATURE:
<221> NAME/KEY: modified_base
<222> LOCATION: (1)..(4)
<223> OTHER INFORMATION: phosphorothioate linkage
<220> FEATURE:
<221> NAME/KEY: modified_base
<222> LOCATION: (27)..(30)
<223> OTHER INFORMATION: phosphorothioate linkage

<400> SEQUENCE: 9
attattattt taaatttaca gaaggggaaa 30

<210> SEQ ID NO 10
<211> LENGTH: 30
<212> TYPE: RNA
<213> ORGANISM: Artificial Sequence
<220> FEATURE:
<223> OTHER INFORMATION: synthetic oligo, N7 RNA
<220> FEATURE:
<221> NAME/KEY: modified_base
<222> LOCATION: (1)..(4)
<223> OTHER INFORMATION: phosphorothioate linkage
<220> FEATURE:
<221> NAME/KEY: modified_base
<222> LOCATION: (27)..(30)
<223> OTHER INFORMATION: phosphorothioate linkage

<400> SEQUENCE: 10
auuauuauuu uaaauuuaca gaaggggaaa 30

<210> SEQ ID NO 11
<211> LENGTH: 43
<212> TYPE: DNA
<213> ORGANISM: Artificial Sequence
<220> FEATURE:
<223> OTHER INFORMATION: synthetic oligo, N8
<220> FEATURE:
<221> NAME/KEY: modified_base
<222> LOCATION: (1)..(4)
<223> OTHER INFORMATION: phosphorothioate linkage
<220> FEATURE:
<221> NAME/KEY: modified_base
<222> LOCATION: (40)..(43)
<223> OTHER INFORMATION: phosphorothioate linkage

<400> SEQUENCE: 11
acagaagggg aaactaagaa ttatagacat gaagtgactc acc 43

<210> SEQ ID NO 12
<211> LENGTH: 43
<212> TYPE: RNA
<213> ORGANISM: Artificial Sequence
<220> FEATURE:
<223> OTHER INFORMATION: synthetic oligo, N8 RNA
<220> FEATURE:
<221> NAME/KEY: modified_base
<222> LOCATION: (1)..(4)
<223> OTHER INFORMATION: phosphorothioate linkage
<220> FEATURE:
<221> NAME/KEY: modified_base
<222> LOCATION: (40)..(43)
<223> OTHER INFORMATION: phosphorothioate linkage

<400> SEQUENCE: 12
acagaagggg aaacuaagaa uuauagacau gaagugacuc acc 43

<210> SEQ ID NO 13

<211> LENGTH: 25
<212> TYPE: DNA
<213> ORGANISM: Artificial Sequence
<220> FEATURE:
<223> OTHER INFORMATION: synthetic oligo, globin

<400> SEQUENCE: 13
cctcttacct cagttacaat ttata 25

<210> SEQ ID NO 14
<211> LENGTH: 60
<212> TYPE: DNA
<213> ORGANISM: Artificial Sequence
<220> FEATURE:
<223> OTHER INFORMATION: synthetic oligo, Biotin-NXTARN5
<220> FEATURE:
<221> NAME/KEY: modified_base
<222> LOCATION: (1)..(1)
<223> OTHER INFORMATION: biotinylated
<220> FEATURE:
<221> NAME/KEY: modified_base
<222> LOCATION: (1)..(4)
<223> OTHER INFORMATION: phosphorothioate linkage
<220> FEATURE:
<221> NAME/KEY: modified_base
<222> LOCATION: (57)..(60)
<223> OTHER INFORMATION: phosphorothioate linkage

<400> SEQUENCE: 14
attattattt taaatttaca gaaggggaaa ctaagaatta tagacatgaa gtgactcacc 60

<210> SEQ ID NO 15
<211> LENGTH: 25
<212> TYPE: DNA
<213> ORGANISM: Artificial Sequence
<220> FEATURE:
<223> OTHER INFORMATION: synthetic oligo, Biotin-Globin
<220> FEATURE:
<221> NAME/KEY: modified_base
<222> LOCATION: (1)..(1)
<223> OTHER INFORMATION: biotinylated

<400> SEQUENCE: 15
cctcttacct cagttacaat ttata 25

<210> SEQ ID NO 16
<211> LENGTH: 20
<212> TYPE: DNA
<213> ORGANISM: Artificial Sequence
<220> FEATURE:
<223> OTHER INFORMATION: synthetic primer

<400> SEQUENCE: 16
gcaggtggtg gtgtccaatc 20

<210> SEQ ID NO 17
<211> LENGTH: 19
<212> TYPE: DNA
<213> ORGANISM: Artificial Sequence
<220> FEATURE:
<223> OTHER INFORMATION: synthetic primer

<400> SEQUENCE: 17
ccgcaagagg gcagataca 19

<210> SEQ ID NO 18
<211> LENGTH: 22
<212> TYPE: DNA
<213> ORGANISM: Artificial Sequence
<220> FEATURE:
<223> OTHER INFORMATION: synthetic primer

<400> SEQUENCE: 18
ggccctgtaa ttggaatgag tc 22

<210> SEQ ID NO 19
<211> LENGTH: 21
<212> TYPE: DNA
<213> ORGANISM: Artificial Sequence
<220> FEATURE:
<223> OTHER INFORMATION: synthetic primer

<400> SEQUENCE: 19
ccaagatcca actacgagct t 21

<210> SEQ ID NO 20
<211> LENGTH: 22
<212> TYPE: DNA
<213> ORGANISM: Artificial Sequence
<220> FEATURE:
<223> OTHER INFORMATION: synthetic primer

<400> SEQUENCE: 20
atggtgagca gagtgcccta tc 22

<210> SEQ ID NO 21
<211> LENGTH: 22
<212> TYPE: DNA
<213> ORGANISM: Artificial Sequence
<220> FEATURE:
<223> OTHER INFORMATION: synthetic primer

<400> SEQUENCE: 21
atggtccctg gcagtctcca aa 22

<210> SEQ ID NO 22
<211> LENGTH: 20
<212> TYPE: DNA
<213> ORGANISM: Artificial Sequence
<220> FEATURE:
<223> OTHER INFORMATION: synthetic primer

<400> SEQUENCE: 22
cagggatgac tctgggagaa 20

<210> SEQ ID NO 23
<211> LENGTH: 20
<212> TYPE: DNA
<213> ORGANISM: Artificial Sequence
<220> FEATURE:
<223> OTHER INFORMATION: synthetic primer

<400> SEQUENCE: 23
gccctctaga gccctcattt 20

<210> SEQ ID NO 24
<211> LENGTH: 22
<212> TYPE: DNA
<213> ORGANISM: Artificial Sequence
<220> FEATURE:
<223> OTHER INFORMATION: synthetic primer

<400> SEQUENCE: 24
cgcaagttca ccctcagaag gt 22

-continued

<210> SEQ ID NO 25
<211> LENGTH: 23
<212> TYPE: DNA
<213> ORGANISM: Artificial Sequence
<220> FEATURE:
<223> OTHER INFORMATION: synthetic primer

<400> SEQUENCE: 25
gacgtgatac cttgaagcac acc 23

<210> SEQ ID NO 26
<211> LENGTH: 25
<212> TYPE: DNA
<213> ORGANISM: Artificial Sequence
<220> FEATURE:
<223> OTHER INFORMATION: synthetic primer

<400> SEQUENCE: 26
caggagtgta cgggaatgtg atggt 25

<210> SEQ ID NO 27
<211> LENGTH: 24
<212> TYPE: DNA
<213> ORGANISM: Artificial Sequence
<220> FEATURE:
<223> OTHER INFORMATION: synthetic primer

<400> SEQUENCE: 27
gattagccgt ctgccctcat ttgt 24

<210> SEQ ID NO 28
<211> LENGTH: 22
<212> TYPE: DNA
<213> ORGANISM: Artificial Sequence
<220> FEATURE:
<223> OTHER INFORMATION: synthetic primer

<400> SEQUENCE: 28
actttgggct gatgcgagca ct 22

<210> SEQ ID NO 29
<211> LENGTH: 22
<212> TYPE: DNA
<213> ORGANISM: Artificial Sequence
<220> FEATURE:
<223> OTHER INFORMATION: synthetic primer

<400> SEQUENCE: 29
aaggtgcgtg tcttcaggct ct 22

<210> SEQ ID NO 30
<211> LENGTH: 22
<212> TYPE: DNA
<213> ORGANISM: Artificial Sequence
<220> FEATURE:
<223> OTHER INFORMATION: synthetic primer

<400> SEQUENCE: 30
caccattggc aatgagcggt tc 22

<210> SEQ ID NO 31
<211> LENGTH: 22
<212> TYPE: DNA
<213> ORGANISM: Artificial Sequence
<220> FEATURE:
<223> OTHER INFORMATION: synthetic primer -continued

<400> SEQUENCE: 31
aggtctttgc ggatgtccac gt 22

<210> SEQ ID NO 32
<211> LENGTH: 20
<212> TYPE: DNA
<213> ORGANISM: Artificial Sequence
<220> FEATURE:
<223> OTHER INFORMATION: synthetic primer

<400> SEQUENCE: 32
gggtgatttt gcctttgaga 20

<210> SEQ ID NO 33
<211> LENGTH: 20
<212> TYPE: DNA
<213> ORGANISM: Artificial Sequence
<220> FEATURE:
<223> OTHER INFORMATION: synthetic primer

<400> SEQUENCE: 33
ctgcctttct tcctgtctgg 20

<210> SEQ ID NO 34
<211> LENGTH: 18
<212> TYPE: DNA
<213> ORGANISM: Artificial Sequence
<220> FEATURE:
<223> OTHER INFORMATION: synthetic primer

<400> SEQUENCE: 34
gcccgagttt gcagagag 18

<210> SEQ ID NO 35
<211> LENGTH: 17
<212> TYPE: DNA
<213> ORGANISM: Artificial Sequence
<220> FEATURE:
<223> OTHER INFORMATION: synthetic primer

<400> SEQUENCE: 35
agtcgcctgg ctcctaa 17

<210> SEQ ID NO 36
<211> LENGTH: 18
<212> TYPE: DNA
<213> ORGANISM: Artificial Sequence
<220> FEATURE:
<223> OTHER INFORMATION: synthetic primer

<400> SEQUENCE: 36
cacaggctac ctggtcct 18

<210> SEQ ID NO 37
<211> LENGTH: 17
<212> TYPE: DNA
<213> ORGANISM: Artificial Sequence
<220> FEATURE:
<223> OTHER INFORMATION: synthetic primer

<400> SEQUENCE: 37
tctgggacgc aacctct 17

<210> SEQ ID NO 38

-continued

<211> LENGTH: 18
<212> TYPE: DNA
<213> ORGANISM: Artificial Sequence
<220> FEATURE:
<223> OTHER INFORMATION: synthetic primer

<400> SEQUENCE: 38
ttctgggtca ccctcagc 18

<210> SEQ ID NO 39
<211> LENGTH: 17
<212> TYPE: DNA
<213> ORGANISM: Artificial Sequence
<220> FEATURE:
<223> OTHER INFORMATION: synthetic primer

<400> SEQUENCE: 39
caccaccacc acacggt 17

<210> SEQ ID NO 40
<211> LENGTH: 20
<212> TYPE: DNA
<213> ORGANISM: Artificial Sequence
<220> FEATURE:
<223> OTHER INFORMATION: synthetic primer

<400> SEQUENCE: 40
gtagttgctt gggtcggttt 20

<210> SEQ ID NO 41
<211> LENGTH: 22
<212> TYPE: DNA
<213> ORGANISM: Artificial Sequence
<220> FEATURE:
<223> OTHER INFORMATION: synthetic primer

<400> SEQUENCE: 41
ctgatgcaaa cctgaagtag gg 22

<210> SEQ ID NO 42
<211> LENGTH: 20
<212> TYPE: DNA
<213> ORGANISM: Artificial Sequence
<220> FEATURE:
<223> OTHER INFORMATION: synthetic primer

<400> SEQUENCE: 42
acaccaggga attagcaggc 20

<210> SEQ ID NO 43
<211> LENGTH: 40
<212> TYPE: DNA
<213> ORGANISM: Artificial Sequence
<220> FEATURE:
<223> OTHER INFORMATION: synthetic primer

<400> SEQUENCE: 43
acaccaggga attagcaggc gccttccttc tgcagcaatc 40

<210> SEQ ID NO 44
<211> LENGTH: 22
<212> TYPE: DNA
<213> ORGANISM: Artificial Sequence
<220> FEATURE:
<223> OTHER INFORMATION: synthetic primer

<400> SEQUENCE: 44
cctctctggt gtcatatcgc tt 22

<210> SEQ ID NO 45
<211> LENGTH: 24
<212> TYPE: DNA
<213> ORGANISM: Artificial Sequence
<220> FEATURE:
<223> OTHER INFORMATION: synthetic primer

<400> SEQUENCE: 45
gtccttggtg ctagatctgt aagg 24

<210> SEQ ID NO 46
<211> LENGTH: 22
<212> TYPE: DNA
<213> ORGANISM: Artificial Sequence
<220> FEATURE:
<223> OTHER INFORMATION: synthetic primer

<400> SEQUENCE: 46
gtgaggattc agttcattca cg 22

<210> SEQ ID NO 47
<211> LENGTH: 23
<212> TYPE: DNA
<213> ORGANISM: Artificial Sequence
<220> FEATURE:
<223> OTHER INFORMATION: synthetic primer

<400> SEQUENCE: 47
gccattcttc taagagcctc aca 23

<210> SEQ ID NO 48
<211> LENGTH: 20
<212> TYPE: DNA
<213> ORGANISM: Artificial Sequence
<220> FEATURE:
<223> OTHER INFORMATION: synthetic primer

<400> SEQUENCE: 48
ggcatgggcc tcactagaat 20

<210> SEQ ID NO 49
<211> LENGTH: 20
<212> TYPE: DNA
<213> ORGANISM: Artificial Sequence
<220> FEATURE:
<223> OTHER INFORMATION: synthetic primer

<400> SEQUENCE: 49
agccaagctc agaatgtggg 20

<210> SEQ ID NO 50
<211> LENGTH: 20
<212> TYPE: DNA
<213> ORGANISM: Artificial Sequence
<220> FEATURE:
<223> OTHER INFORMATION: synthetic primer

<400> SEQUENCE: 50
acctttcctc caagctccac 20

<210> SEQ ID NO 51
<211> LENGTH: 22
<212> TYPE: DNA

<213> ORGANISM: Artificial Sequence
<220> FEATURE:
<223> OTHER INFORMATION: synthetic primer

<400> SEQUENCE: 51
ttgctgcaga atctaaagtc ct 22

<210> SEQ ID NO 52
<211> LENGTH: 20
<212> TYPE: DNA
<213> ORGANISM: Artificial Sequence
<220> FEATURE:
<223> OTHER INFORMATION: synthetic oligo
<220> FEATURE:
<221> NAME/KEY: modified_base
<222> LOCATION: (20)..(20)
<223> OTHER INFORMATION: biotinylated

<400> SEQUENCE: 52
caaatgccag ttcttctgtg 20

<210> SEQ ID NO 53
<211> LENGTH: 20
<212> TYPE: DNA
<213> ORGANISM: Artificial Sequence
<220> FEATURE:
<223> OTHER INFORMATION: synthetic oligo

<400> SEQUENCE: 53
caggaaatcc caaggttgta 20

<210> SEQ ID NO 54
<211> LENGTH: 20
<212> TYPE: DNA
<213> ORGANISM: Artificial Sequence
<220> FEATURE:
<223> OTHER INFORMATION: synthetic oligo
<220> FEATURE:
<221> NAME/KEY: modified_base
<222> LOCATION: (20)..(20)
<223> OTHER INFORMATION: biotinylated

<400> SEQUENCE: 54
aattccatat ggagcctttt 20

<210> SEQ ID NO 55
<211> LENGTH: 20
<212> TYPE: DNA
<213> ORGANISM: Artificial Sequence
<220> FEATURE:
<223> OTHER INFORMATION: synthetic oligo
<220> FEATURE:
<221> NAME/KEY: modified_base
<222> LOCATION: (20)..(20)
<223> OTHER INFORMATION: biotinylated

<400> SEQUENCE: 55
actatccaac tcagaggtga 20

<210> SEQ ID NO 56
<211> LENGTH: 20
<212> TYPE: DNA
<213> ORGANISM: Artificial Sequence
<220> FEATURE:
<223> OTHER INFORMATION: synthetic oligo
<220> FEATURE:
<221> NAME/KEY: modified_base
<222> LOCATION: (20)..(20)
<223> OTHER INFORMATION: biotinylated

<400> SEQUENCE: 56
gggattttgg cttcaagttt 20

<210> SEQ ID NO 57
<211> LENGTH: 20
<212> TYPE: DNA
<213> ORGANISM: Artificial Sequence
<220> FEATURE:
<223> OTHER INFORMATION: synthetic oligo
<220> FEATURE:
<221> NAME/KEY: modified_base
<222> LOCATION: (20)..(20)
<223> OTHER INFORMATION: biotinylated

<400> SEQUENCE: 57
atagagattc gggatttcgg 20

<210> SEQ ID NO 58
<211> LENGTH: 1476
<212> TYPE: DNA
<213> ORGANISM: Homo sapiens

<400> SEQUENCE: 58
ggaaaaggaa ggctgcacag aagaactggc atttgtgttc tgcctacaaa gctgaaaagg 60
atttcaccca aatcagggaa gatcagcctt atgaggtgga tattattgcc acaataattt 120
tccagatgaa aaatggaggc ccagagatgt taaggaattt gcccaagatc atgaaaagac 180
actctcccct attgagatgt catgcaagga tcagtgctgt gtgaaaatcc acatgaagca 240
ggaaatgcag gtggtggtgt ccaatctgat ttcaagatct gagaagctgt gcactgcctg 300
aaaggtatct atttaaggtg tcaccagact cctgctccac tcctgcccaa ggcccagccc 360
atccaagagc aaaaggcaag tggtgttaca accttgggat ttcctgtatc tgccctcttg 420
cggatagcag gacagagtca cagctgcatt aaattcgctt aagacttatt gagacacttc 480
aacacttcaa caacgacctg tgagattaag attattattt taaatttaca gaaggggaaa 540
ctaagaatta tagacatgaa gtgactcacc tatgaccacc tggtgataga accaggacta 600
gagctcaggt atgaagattt ctgggggagt ccctgaaaaa aaggctccat atggaattac 660
aatgtggaaa aggccaaggc ctcaccaacc cttttctctt caacacctgg atccctaagt 720
ccttattcgt aacctcctct ttggacaagg ttttggtaga caaagccaga gcctcttgca 780
ctgagaaaga caaattctcc tcttgcagtg aaccacaggt aaatgctcca atagagagtc 840
caagccaaac ctccgggtgt tattcatgac ccaggcaagt ctgctttctc attcccccta 900
tctctagacc gttttccatt tgggcttcct tttcttcttt tatcctcaaa gaaacatgtt 960
tccttctagt aggtttggct gccaccacta gggtcctggc tacaactggc cctcaggtaa 1020
ctctctcacc tctgagttgg atagtatcct ctctcgtccc catacacaag tgtttctctt 1080
cccagacacc ttccttacac aatttcccat ttctttctca tctcaccctt gctttaatca 1140
acatagttct ttcccctgag attactcttc agcctttctt gttgaagcac tgcccagtgg 1200
ttctcttggg atttccattt ctctcccctc agctctcttg gtaccaaatt ctgtaagctt 1260
ctctggtttt tggtttctct tccttctttt ccttccaggc aacatttact caatctaggc 1320
ttggatgatc aggtacttct gccagcctgc ccactaggga actctgggct aggaatatgt 1380
ctcaatggca ccattatatt tggaaggacg cttctgtatt tacactgaac acactaaaat 1440
actaaacttg aagccaaaat cccctctctg gctcca 1476

<210> SEQ ID NO 59
<211> LENGTH: 1476
<212> TYPE: RNA
<213> ORGANISM: Homo sapiens

<400> SEQUENCE: 59
ggaaaaggaa ggcugcacag aagaacuggc auuuguguuc ugccuacaaa gcugaaaagg 60
auuucaccca aaucagggaa gaucagccuu augaggugga uauuauugcc acaauaauuu 120
uccagaugaa aaauggaggc ccagagaugu uaaggaauuu gcccaagauc augaaaagac 180
acucuccccu auugagaugu caugcaagga ucagugcugu gugaaaaucc acaugaagca 240
ggaaaugcag guggugugu ccaaucugau uucaagaucu gagaagcugu gcacugccug 300
aaagguaucu auuuaaggug ucaccagacu ccugcuccac uccugcccaa ggcccagccc 360
auccaagagc aaaaggcaag ugguguuaca accuugggau uuccuguauc ugcccucuug 420
cggauagcag gacagaguca cagcugcauu aaauucgcuu aagacuuauu gagacacuuc 480
aacacuucaa caacgaccug ugagauuaag auuauuauuu uaaauuuaca gaaggggaaa 540
cuaagaauua uagacaugaa gugacucacc uaugaccacc uggugauaga accaggacua 600
gagcucaggu augaagauuu cugggggagu cccugaaaaa aaggcuccau auggaauuac 660
aauguggaaa aggccaaggc cucaccaacc cuuuucucuu caacaccugg aucccuaagu 720
ccuuauucgu aaccuccucu uuggacaagg uuuugguaga caaagccaga gccucuugca 780
cugagaaaga caaauucucc ucuugcagug aaccacaggu aaaugcucca auagagaguc 840
caagccaaac cuccgggugu uauucaugac ccaggcaagu cugcuuucuc auuccccua 900 ucucuagacc guuuuccauu ugggcuuccu uuucuucuuu uauccucaaa gaaacauguu 960
uccuucuagu agguuuggcu gccaccacua ggguccuggc uacaacuggc ccucagguaa 1020
cucucucacc ucugaguugg auaguauccu cucucguccc cauacacaag uguuucucuu 1080
cccagacacc uuccuuacac aauuucccau uucuuucuca ucucacccuu gcuuuaauca 1140
acauaguucu uuccccugag auuacucuuc agccuuucuu guugaagcac ugcccagugg 1200
uucucuuggg auuuccauuu cucuccccuc agcucucuug guaccaaauu cuguaagcuu 1260
cucugguuuu ugguuucucu uccuucuuuu ccuuccaggc aacauuuacu caaucuaggc 1320
uuggaugauc agguacuucu gccagccugc ccacuaggga acucugggcu aggaauaugu 1380
cucaauggca ccauuauauu uggaaggacg cuucuguauu uacacugaac acacuaaaau 1440
acuaaacuug aagccaaaau ccccucucug gcucca 1476

<210> SEQ ID NO 60
<211> LENGTH: 1740
<212> TYPE: DNA
<213> ORGANISM: Homo sapiens

<400> SEQUENCE: 60
ttgtttatta cctgtatgac tttcaacaag ttgctatatt ctctgagctt ctctttcctc 60
atctgtaaaa taaaaataat aatagtacct ttctaatagg attgttgtga ggattcagtt 120
cattcacgta aagcagttag aagaatgact gagatcatgt tcatactgag ttagttcatg 180
tgaggctctt agaagaatgg ctaggccggg cacggtggct catgcccata atcccagcac 240
tttgggaggc tgaggagggt ggatcagctg aggtcaggag ttcaagacct gtctggccaa 300
catagtgaaa ctccatctct actaaaaaga caaaaattag ctacgtgtgg tggcacacac 360
ctgtagtccc agctactcgg gaggctgagc taggagaatc atttgaacat aggaggcaga 420

-continued

```
ggctgcaatg agacaagatt gtgccactgc actccagcag cctgggcgat agagcgaaac    480
tccatctcaa aaacaaacaa acaaacaaac aaaaagaaag aaagaaaaga agagaaatgg    540
ctagcacata gtcagtgtat aataaatgtt agctgctata atagtccatc acttatatcc    600
tataatagat aatagaacca caaccttgtt attccttgat aaggcccttt catttcaatc    660
tgaacacaca agctaaatgt ccttgcaata ttgtactcct tttgtgtcca tatgactgtc    720
ctggtttgcc atctttgaca gaaactgctt ttaacagctt tgcatccaag ttttctggac    780
actgccatag tgcacacagt tacattttgg ccagcattga aaagcgggtg actaagggat    840
gataatgctg aatgggagac aaaggggcta tttctgatat gctagtattt gattgttgta    900
tttgaatatg ctttagtccc agatttcagt tgattcagga aataatatag ccagaattgg    960
tattctatga gaatgtaatc tgttttggtc tgttgaaaaa tactgtttgt ttttctccat   1020
ggctttgatc ataataattc aaaattttag tttacaaaag cttgaatcat ctatctaaat   1080
aaagtaacag attttcaact gacaaatacc aaagcactgt ttgtgactca ttaggtatag   1140
gaattcctac tgataaccct gtactttcca aaatatgaga gaataacacc ccttcttttt   1200
attaacttac atttttactc ggccagaaat taaggaaact tctgacgttc acaagttgat   1260
tcatgatatt ctaagtagtt atctgccctg gatcagagtg aaagtaagag ggctgggggc   1320
atttcctcag gggcttctga gatatgtcat acttctctgt taggcaagta gaggaaggca   1380
ttagcaagga attgtgggat tccacctata acacatcatc agtgctattc ccttgtgact   1440
tcgctgtcac ccattcccag aagcagctgc caggaaatga gtacaaataa tttgtcctca   1500
agtcaagata gagccagtcc aaccctaacc aaagttttca gttagcagca aataatttgt   1560
atctctgggg accagggatc acttgatgag tggggctaat ttcttaaaac cctggtgtgg   1620
aagaaataat tctgacaaag gagaatgcgt gccccatatt tctctgcgtc tgaatagcta   1680
aatgaccttg ggtgagtcac ttaagctttc agaggctcag tttcctctcc tgtgcaacag   1740
```

NXTAR-DERIVED OLIGONUCLEOTIDES AND USES THEREOF

CROSS-REFERENCE TO RELATED APPLICATIONS

This application claims priority from U.S. Provisional Application Ser. No. 63/126,916 filed on Dec. 17, 2020, which is incorporated herein by reference in its entirety.

STATEMENT REGARDING FEDERALLY SPONSORED RESEARCH OR DEVELOPMENT

Not applicable.

MATERIAL INCORPORATED-BY-REFERENCE

The Sequence Listing, which is a part of the present disclosure, includes a computer-readable form comprising nucleotide and/or amino acid sequences of the present invention (file name "019605-US-NP_Sequence_Listing.txt" created 16 Dec. 2021; 19,358 bytes). The subject matter of the Sequence Listing is incorporated herein by reference in its entirety.

FIELD OF THE INVENTION

The present disclosure generally relates to NXTAR-derived oligonucleotides.

SUMMARY OF THE INVENTION

Among the various aspects of the present disclosure is the provision of NXTAR-derived oligonucleotides and uses thereof.

An aspect of the present disclosure provides for a method of (i) suppressing androgen receptor (AR) expression, (ii) suppressing androgen receptor splice variants, including AR-V7 expression, (iii) treating cancer (e.g., prostate, breast, testis, ovarian, endometrial and skin), or (iv) treating skin related diseases, such as androgenetic alopecia and acne vulgaris, in a subject comprising administering to the subject a NXTAR-derived oligonucleotide (oligo) (NXTAR is a lncRNA also known as LOC105373241). 1. A method of suppressing androgen receptor (AR) in a subject in need thereof comprising: administering an amount of a NXTAR-derived oligonucleotide sufficient to suppress AR and the NXTAR-derived oligonucleotide has AR-suppressing activity, wherein the subject has or is suspected of having a AR-associated disease, disorder, or condition. Another aspect of the present disclosure provides for a method of treating a subject with NXTAR-derived oligonucleotide therapy comprising: detecting levels of NXTAR and if levels are low (e.g., downregulated NXTAR or low NXTAR transcript levels), treat the subject with NXTAR-derived oligonucleotide. Yet another aspect of the present disclosure provides for a composition comprising an isolated NXTAR-derived oligonucleotide comprising an at least a 60% identical portion of SEQ ID NO: 58 or SEQ ID NO: 59, wherein the isolated NXTAR-derived oligonucleotide is formulated in a pharmaceutically acceptable excipient or carrier, optionally, a nanoparticle or encapsulation by delivery carriers, such as lipids, lipid nanoparticles, polymers, or peptides, having AR-suppressing activity. Yet another aspect of the present disclosure provides for a kit comprising: at least one nucleic acid designed to target AR gene; a pharmaceutical carrier; and instructions for administration. Yet another aspect of the present disclosure provides for a method of treating a subject with a NXTAR-derived oligonucleotide, wherein the subject is suffering from recurrent or AR inhibitor-resistant cancer, the method comprising the steps of: obtaining or having been obtained a biological sample from a patient; performing or having performed an assay to determine if the patient has downregulated NXTAR; and if the patient has low or downregulated NXTAR, then the patient is administered a NXTAR-derived oligonucleotide. Yet another aspect of the present disclosure provides for a method of treating an androgen receptor (AR)-associated disease, disorder, or condition in a subject in need thereof comprising: administering a therapeutically effective amount of a NXTAR-derived oligonucleotide having AR-suppressing activity. Yet another aspect of the present disclosure provides for a pharmaceutical composition comprising an isolated NXTAR-derived oligonucleotide at least 80% identical to a sequence selected from one of (DNA or RNA): SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; or SEQ ID NO: 12. In some embodiments, the pharmaceutical composition has AR or AR-V7 expression reducing activity. In some embodiments, the NXTAR-derived oligonucleotide is derived from a portion of SEQ ID NO: 58 or SEQ ID NO: 59 and comprises a single or double-stranded DNA or RNA. In some embodiments, the NXTAR-derived oligonucleotide is derived from a portion of SEQ ID NO: 58, SEQ ID NO: 59, or SEQ ID NO: 60 and is at least 10 to 20 residues in length. In some embodiments, the NXTAR-derived oligonucleotide is at least 60% to 80% identical to the residues in a portion of SEQ ID NO: 58 or SEQ ID NO: 59 or at least 60% to 80% identical to a complementary strand of a portion of SEQ ID NO: 60. In some embodiments, the NXTAR-derived oligonucleotide comprises at least 80% sequence identity to residues 511 to 570, 511 to 540, 528 to 570, 982 to 1014, or 511 to 570 of SEQ ID NO: 58 or SEQ ID NO: 59. In some embodiments, the NXTAR-derived oligonucleotide comprises at least 80% sequence identity to a portion of SEQ ID NO: 58 or SEQ ID NO: 59. In some embodiments, the NXTAR-derived oligonucleotide comprises at least 80% sequence identity to a reverse, complement, or reverse-complement of a portion SEQ ID NO: 58 or SEQ ID NO: 59. In some embodiments, the NXTAR-derived oligonucleotide is functional and has AR binding activity. In some embodiments, the NXTAR-derived oligonucleotide comprises: an oligonucleotide having at least 60% identity to a portion of NXTAR (SEQ ID NO: 58) or corresponding NXTAR RNA (SEQ ID NO: 59) or reverse, complement, or reverse-complement thereof; or an oligonucleotide having at least 60% identity to a portion of AR promoter region (SEQ ID NO: 60) or corresponding RNA or reverse, complement, or reverse-complement thereof; and/or the NXTAR-derived oligonucleotide is functional and has AR binding activity. In some embodiments, the oligonucleotide has at least 60% identity to a portion of NXTAR (SEQ ID NO: 58) or corresponding NXTAR RNA (SEQ ID NO: 59), reverse, complement, or reverse-complement thereof. In some embodiments, the oligonucleotide has 60% homology to the complementary strand of a portion of the AR promoter (SEQ ID NO: 60) or complementary DNA or corresponding RNA thereof. In some embodiments, the oligonucleotide comprises a portion of or reverse, complement, or reverse-complement to a portion of SEQ ID NO: 58 or SEQ ID NO: 59 having binding affinity to an androgen receptor target. In some embodiments, the oligonucleotide comprises an RNA molecule encoded by a nucleic acid molecule having 80% identity to a portion of SEQ ID NO: 58, or a functional fragment, portion, or variant thereof. In some embodiments, the oligonucleotide comprises an RNA molecule having 80% identity to a portion of SEQ ID NO: 59, or a functional fragment, portion, or variant thereof. In some embodiments, the oligonucleotide comprises an RNA molecule having 80% identity to the complement of a portion of SEQ ID NO: 60, or a functional fragment, portion, or variant thereof. In some embodiments, the NXTAR-derived oligonucleotide has (i) at least 80% identity to a portion of: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; or SEQ ID NO: 12; or (ii) at least 80% identity to a corresponding, reverse, complement, or reverse-complement RNA or DNA nucleotide sequence of a portion of: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; or SEQ ID NO: 12. In some embodiments, the NXTAR-derived oligonucleotide comprises a portion of, variants, deletions, substitutions, insertions, combinations of portions, conservative substitutions, reverse, complement, or reverse-complement of and having at least 80% identity to at least a portion of SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8; SEQ ID NO: 9; SEQ ID NO: 10; SEQ ID NO: 11; or SEQ ID NO: 12. In some embodiments, the NXTAR-derived oligonucleotide comprises one or more phosphodiester or phosphorothioate bond modifications. In some embodiments, the NXTAR-derived oligonucleotide has a phosphodiester or a phosphorothioate bond modification. In some embodiments, the NXTAR-derived oligonucleotide comprises a gain of function variant that increases the binding affinity to AR. In some embodiments, the amount of NXTAR-derived oligonucleotide is an amount sufficient to: negatively regulate AR; suppress, reduce, or inhibit AR expression; suppress, reduce, or inhibit splice variant AR-V7 mRNA expression; or restore, induce, or upregulate NXTAR expression. In some embodiments, the amount of the NXTAR-derived oligonucleotide is an amount sufficient to: suppress, reduce, or inhibit cancer cell proliferation; suppress, reduce, or inhibit growth or proliferation of cancer cells, optionally, prostate cancer cells, breast cancer cells, testicular cancer cells, ovarian cancer cells, endometrial cancer cells, skin cancer cells; or suppress, reduce, or inhibit tumors in treatment-resistant cancer. In some embodiments, the NXTAR-derived oligonucleotide suppresses AR in skin-related diseases, optionally, androgenetic alopecia, or acne vulgaris. In some embodiments, the subject has cancer. In some embodiments, the cancer is an AR-overexpressing or an AR-V7-overexpressing cancer, prostate cancer, breast cancer, testicular cancer, ovarian cancer, endometrial cancer, skin cancer, or any other AR-associated cancer or AR expressing cancer. In some embodiments, the cancer is recurrent prostate cancer or drug-resistant prostate cancer. In some embodiments, the cancer is an AR antagonist-resistant cancer. In some embodiments, the AR antagonist is enzalutamide or abiraterone. In some embodiments, the cancer is prostate cancer resistant to an AR antagonist, wherein the AR antagonist is optionally abiraterone, an androgen biosynthesis inhibitor or enzalutamide, a drug that inhibits AR nuclear translocation. In some embodiments, the cancer is castration-resistant prostate cancer (CRPC) that has developed resistance to second-generation AR antagonists, optionally, enzalutamide. In some embodiments, the subject has a skin-related disease selected from an AR-expressing skin disease, androgenetic alopecia, or acne vulgaris. In some embodiments, the subject has downregulated NXTAR or low NXTAR transcript levels. In some embodiments, administering the NXTAR-derived oligonucleotide is via administration to or transfection into cells or tissues. In some embodiments, the method further comprises administering an ACK1/TNK2 inhibitor to the subject. In some embodiments, the ACK1/TNK2 inhibitor is (R)-9b. In some embodiments, the method further comprises administering an ACK1/TNK2 tyrosine kinase inhibiting agent, optionally (R)-9b, wherein the ACK1/TNK2 tyrosine kinase inhibiting agent prevents AR binding to Ppr3 and 4 and enables GCN5 recruitment following H3K14ac mark deposition; the ACK1/TNK2 tyrosine kinase inhibiting agent treatment enhances EZH2 recruitment and H3K27me3 marks on AR promoter site; and the NXTAR-derived oligonucleotide sensitizes prostate cancer cells to (R)-9b. In some embodiments, the method further comprises administering an anti-cancer treatment selected from abiraterone, an androgen biosynthesis inhibitor or enzalutamide, or a drug that inhibits AR nuclear translocation before, during, or after administration of the NXTAR-derived oligonucleotide.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 7A-FIG. 7I. NXTAR derived oligonucleotide NXTAR-N5 suppresses prostate cancer proliferation. (A) Location of NXTAR-N5 binding region upstream of AR gene shown in a graphical format. (B) BLASTN analysis showing regions of significant homology (complementarity to other strand) in the upstream regions of AR and exon 5 of NXTAR. (C) The NXTAR-N5 oligonucleotide sequence is shown. *Represents a Phosphorothioate bond modifications to avoid degradation by exonucleases. (D) VCaP and 22Rv1 cells were transfected with NXTAR-N5 oligonucleotide and cell proliferation was measured using trypan blue exclusion method. (E) VCaP and 22Rv1 cells were transfected with NXTAR-N5, and RNA was prepared, followed by qRT-PCR for AR and AR-V7 mRNA. (F) Biotin conjugated NXTAR-N5 and Globin oligos were incubated with lysate from fixed VCaP cells and qPCR was performed for AR Up1.1 primers (see e.g., FIG. 7A). (G) VCaP cell lysate was subjected to chromatin pull down using NXTAR-N5 biotin conjugated oligos, followed by immunoblotting for EZH2. Actin was used as loading control. (H) NXTAR-N5 and Globin oligos were incubated with purified EZH2. Pull-down was washed, followed by immunoblotting with EZH2 antibodies. (I) VCaP cells were transfected with Globin and NXTAR-N5 oligos and subjected to ChIP with H3K27me3 antibody followed by qPCR for site upstream of AR TSS (−0.7 kb). Data are represented as mean±SEM. $p<0.01$. $* p<0.001$.

FIG. 12. NXTAR-N5 region derived from exon 5 of NXTAR, complementary to the upstream region of AR gene is shown.

DETAILED DESCRIPTION OF THE INVENTION

Figure 1A:
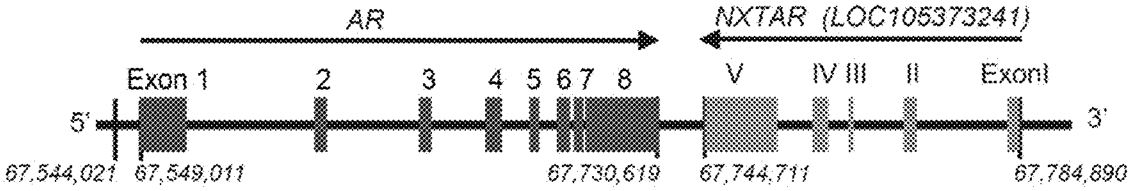
FIG. 1A-FIG. 1M. NXTAR is a novel tumor suppressor lncRNA in human prostate cancer. (A) Location of NXTAR gene with respect to AR gene on chromosome X, shown in a graphical format. The exons 1-5 in NXTAR are shown in Roman numerals (I to V), to distinguish from AR exons. (B-L) Total RNA isolated from paired normal human prostates and tumor samples and subjected to qRT-PCR and relative expression of NXTAR (B and F) and KLK3 (D and H) is shown. Data representing mean of relative NXTAR (C, G and J) and KLK3 (E, I, and K) expression between Normal and Tumor samples is shown. (L) A relative NXTAR expression in various Gleason grades of prostate tumor samples is shown. (M) Total RNA isolated from various cell lines and subjected to qRT-PCR with NXTAR and 18S primers. Data are represented as mean±SEM as in (B-L). * $p<0.001$,  $p<0.01$, * $p\leq0.05$, two-tailed Student's t-test. NS, not significant.

The present disclosure is based, at least in part, on the discovery of a long non coding RNA (LncRNA), named NXTAR (also known as LOC105373241). The inventors uncovered that prostate cancers develop ways to stop this RNA molecule to allow themselves to grow. Studying the stretch of DNA that codes for the androgen receptor, the researchers discovered that a section of the DNA molecule next to the androgen receptor produced a molecule called a long noncoding RNA.

It was discovered that this long noncoding RNA is critical in regulating the androgen receptor. In prostate cancer, the androgen receptor is very clever. As shown herein, AR suppresses its own suppressor; essentially it binds to NXTAR and shuts it down. This means that in all the prostate cancer samples that have been studied, NXTAR is rarely found, because it is suppressed by the heavy presence of the androgen receptor in these types of tumors. NXTAR was discovered by using a drug that the inventors developed that suppresses the androgen receptor. When the androgen receptor is suppressed, NXTAR starts to appear. When this was observed, it was suspected that this lncRNA is a tumor suppressor.

NXTAR-Derived Oligonucleotides

The standard strategy for treating prostate cancer is to block the hormones that drive tumor growth with drugs. This strategy works, but many patients ultimately stop responding. The inventors discovered an alternative strategy—one that exploits an RNA molecule with the power to tamp down prostate tumors.

The inventors discovered the long noncoding RNA when they were studying the part of DNA that produces the androgen receptor (AR). They observed that the androgen receptor can shut off the RNA molecule, which they dubbed NXTAR (next to androgen receptor), by binding to it. This means that in the prostate cancer samples that had been studied, NXTAR was rarely found, because it is suppressed by the heavy presence of the androgen receptor in these types of tumors. When using a drug originally developed to shut off expression of the androgen receptor in prostate tumors, it was found that NXTAR started to appear. In mice implanted with human prostate tumor samples, dialing up NXTAR caused the cancer to shrink. Thus, as shown herein, restoring NXTAR expression causes tumors to shrink as shown using human prostate tumor samples implanted in mice.

In patients that have developed resistance to the front-line treatments, (R)-9b drug and NXTAR can be developed into new therapies for prostate cancer patients. It is envisioned to encapsulate the small molecule drug and a key piece of NXTAR into nanoparticles, perhaps into the same nanoparticle, and shut down the androgen receptor in two different ways. "Inhibitors of ACK1/TNK2 Tyrosine Kinase", U.S. Pat. Nos. 9,850,216 and 10,017,478 are incorporated by reference.

As shown herein, oligonucleotides (oligos), named NXTAR-N series of oligos, can be used as a new therapeutic modality in cancers (e.g., prostate, some breast cancers). These oligos are derived from the newly identified long non coding RNA (LncRNA), named NXTAR (also known as LOC105373241). These oligos, in the form of single or double-stranded DNA or RNA, have the ability to suppress androgen receptor (AR) expression in prostate, breast and other AR expressing cancer cell lines. It may also play important roles in suppressing AR in several skin related diseases, such as androgenetic alopecia and acne vulgaris. NXTAR-N5 was discovered to be effective.

A NXTAR-derived oligonucleotide can be any nucleotide sequence derived from the NXTAR sequence that has AR expression reducing, AR variants such as AR-V7 expression reducing, or cancer-inhibiting activity.

The NXTAR-derived oligonucleotide can be derived from SEQ ID NO: 58 (LOC105373241) or corresponding RNA (SEQ ID NO: 59) or complementary strand thereof:

1 ggaaaaggaa ggctgcacag aagaactggc atttgtgttc tgcctacaaa gctgaaaagg 61 atttcaccca aatcagggaa gatcagcctt atgaggtgga tattattgcc acaataattt 121 tccagatgaa aaatggaggc ccagagatgt taaggaattt gcccaagatc atgaaaagac 181 actctcccct attgagatgt catgcaagga tcagtgctgt gtgaaaatcc acatgaagca 241 ggaaatgcag gtggtggtgt ccaatctgat ttcaagatct gagaagctgt gcactgcctg 301 aaaggtatct atttaaggtg tcaccagact cctgctccac tcctgcccaa ggcccagccc 361 atccaagagc aaaaggcaag tggtgttaca accttgggat ttcctgtatc tgccctcttg 421 cggatagcag gacagagtca cagctgcatt aaattcgctt aagacttatt gagacacttc 481 aacacttcaa caacgacctg tgagattaag attattattt taaatttaca gaaggggaaa

541 ctaagaatta tagacatgaa gtgactcacc tatgaccacc tggtgataga accaggacta 601 gagctcaggt atgaagattt ctgggggagt ccctgaaaaa aaggctccat atggaattac 661 aatgtggaaa aggccaaggc ctcaccaacc cttttctctt caacacctgg atccctaagt 721 ccttattcgt aacctcctct ttggacaagg ttttggtaga caaagccaga gcctcttgca 781 ctgagaaaga caaattctcc tcttgcagtg aaccacaggt aaatgctcca atagagagtc 841 caagccaaac ctccgggtgt tattcatgac ccaggcaagt ctgctttctc attcccccta 901 tctctagacc gttttccatt tgggcttcct tttcttcttt tatcctcaaa gaaacatgtt 961 tccttctagt aggtttggct gccaccacta gggtcctggc tacaactggc cctcaggtaa -continued 1021 ctctctcacc tctgagttgg atagtatcct ctctcgtccc catacacaag tgtttctctt 1081 cccagacacc ttccttacac aatttcccat ttctttctca tctcaccctt gctttaatca 1141 acatagttct ttcccctgag attactcttc agcctttctt gttgaagcac tgcccagtgg 1201 ttctcttggg atttccattt ctctcccctc agctctcttg gtaccaaatt ctgtaagctt 1261 ctctggtttt tggtttctct tccttctttt ccttccaggc aacatttact caatctaggc 1321 ttggatgatc aggtacttct gccagcctgc ccactaggga actctgggct aggaatatgt 1381 ctcaatggca ccattatatt tggaaggacg cttctgtatt tacactgaac acactaaaat 1441 actaaacttg aagccaaaat cccctctctg gctcca The NXTAR-derived oligonucleotide can be derived from SEQ ID NO: 59 (corresponding RNA to SEQ ID NO: 58):

1 ggaaaaggaa ggcugcacag aagaacuggc auuuguguuc ugccuacaaa gcugaaaagg 61 auuucaccca aaucagggaa gaucagccuu augaggugga uauuauugcc acaauaauuu 121 uccagaugaa aaauggaggc ccagagaugu uaaggaauuu gcccaagauc augaaaagac 181 acucuccccu auugagaugu caugcaagga ucagugcugu gugaaaaucc acaugaagca 241 ggaaaugcag gugguggugu ccaaucugau uucaagaucu gagaagcugu gcacugccug 301 aaagguaucu auuuaaggug ucaccagacu ccugcuccac uccugcccaa ggcccagccc 361 auccaagagc aaaaggcaag ugguguuaca accuugggau uuccuguauc ugcccucuug 421 cggauagcag gacagaguca cagcugcauu aaauucgcuu aagacuuauu gagacacuuc 481 aacacuucaa caacgaccug ugagauuaag auuauuauuu uaaauuuaca gaaggggaaa

541 cuaagaauua uagacaugaa gugacucacc uaugaccacc uggugauaga accaggacua 601 gagcucaggu augaagauuu cugggggagu cccugaaaaa aaggcuccau auggaauuac 661 aauguggaaa aggccaaggc cucaccaacc cuuuucucuu caacaccugg aucccuaagu 721 ccuuauucgu aaccuccucu uuggacaagg uuuugguaga caaagccaga gccucuugca 781 cugagaaaga caaauucucc ucuugcagug aaccacaggu aaaugcucca auagagaguc 841 caagccaaac cuccgggugu uauucaugac ccaggcaagu cugcuuucuc auuccccua 901 ucucuagacc guuuuccauu ugggcuuccu uuucuucuuu uauccucaaa gaaacauguu 961 uccuucuagu agguuuggcu gccaccacua ggguccuggc uacaacuggc ccucagguaa 1021 cucucucacc ucugaguugg auaguauccu cucucguccc cauacacaag uguuucucuu 1081 cccagacacc uuccuuacac aauuucccau uucuuucuca ucucacccuu gcuuuaauca 1141 acauaguucu uuccccugag auuacucuuc agccuuucuu guugaagcac ugcccagugg 1201 uucucuuggg auuuccauuu cucuccccuc agcucucuug guaccaaauu cuguaagcuu 1261 cucugguuuu ugguuucucu uccuucuuuu ccuuccaggc aacauuuacu caaucuaggc 1321 uuggaugauc agguacuucu gccagccugc ccacuaggga acucugggcu aggaauaugu 1381 cucaauggca ccauuauauu uggaaggacg cuucuguauu uacacugaac acacuaaaau 1441 acuaaacuug aagccaaaau ccccucucug gcucca NXTAR Exon 5 (N5 sequence is highlighted):

39061 gcccatccaa gagcaaaagg caagtggtgt tacaaccttg ggatttcctg tatctgccct

-continued

```
39121 cttgcggata gcaggacaga gtcacagctg cattaaattc
      gcttaagact tattgagaca
39181 cttcaacact tcaacaacga cctgtgagat taagattatt
      attttaaatt tacagaaggg
39241 gaaactaaga attatagaca tgaagtgact cacctatgac
      cacctggtga tagaaccagg
39301 actagagctc aggtatgaag atttctgggg gagtccctga
      aaaaaaggct ccatatggaa
39361 ttacaatgtg gaaaaggcca aggcctcacc aaccctttc
      tcttcaacac ctggatccct
39421 aagtccttat tcgtaacctc ctctttggac aaggttttgg
      tagacaaagc cagagcctct
39481 tgcactgaga aagacaaatt ctcctcttgc agtgaaccac
      aggtaaatgc tccaatagag
```

AR Promoter (67,534,381 to 67,536,121) (SEQ ID NO: 60):

```
ttgtttatta cctgtatgac tttcaacaag ttgctatatt
ctctgagctt ctctttcctc atctgtaaaa taaaaataat
aatagtacct ttctaatagg attgttgtga ggattcagtt
cattcacgta aagcagttag aagaatgact gagatcatgt
tcatactgag ttagttcatg tgaggctctt agaagaatgg
ctaggccggg cacggtggct catgcccata atcccagcac
tttgggaggc tgaggagggt ggatcagctg aggtcaggag
ttcaagacct gtctggccaa catagtgaaa ctccatctct
actaaaaaga caaaaattag ctacgtgtgg tggcacacac
ctgtagtccc agctactcgg gaggctgagc taggagaatc
atttgaacat aggaggcaga ggctgcaatg agacaagatt
gtgccactgc actccagcag cctgggcgat agagcgaaac
tccatctcaa aaacaaacaa acaaacaaac aaaaagaaag
aaagaaaaga agagaaatgg ctagcacata gtcagtgtat
aataaatgtt agctgctata atagtccatc acttatatcc
tataatagat aatagaacca caaccttgtt attccttgat
aaggcccttt catttcaatc tgaacacaca agctaaatgt
ccttgcaata ttgtactcct tttgtgtcca tatgactgtc
ctggtttgcc atctttgaca gaaactgctt ttaacagctt
tgcatccaag ttttctggac actgccatag tgcacacagt
tacattttgg ccagcattga aaagcgggtg actaagggat
gataatgctg aatgggagac aaaggggcta tttctgatat
gctagtattt gattgttgta tttgaatatg ctttagtccc
agatttcagt tgattcagga aataatatag ccagaattgg
```

-continued

```
tattctatga gaatgtaatc tgttttggtc tgttgaaaaa
tactgtttgt ttttctccat ggctttgatc ataataattc
aaaattttag tttacaaaag cttgaatcat ctatctaaat
aaagtaacag attttcaact gacaaatacc aaagcactgt
ttgtgactca ttaggtatag gaattcctac tgataaccct
gtactttcca aaatatgaga gaataacacc ccttcttttt
attaacttac atttttactc ggccagaaat taaggaaact
tctgacgttc acaagttgat tcatgatatt ctaagtagtt
atctgccctg gatcagagtg aaagtaagag ggctgggggc
atttcctcag gggcttctga gatatgtcat acttctctgt
taggcaagta gaggaaggca ttagcaagga attgtgggat
tccacctata acacatcatc agtgctattc ccttgtgact
tcgctgtcac ccattcccag aagcagctgc caggaaatga
gtacaaataa tttgtcctca agtcaagata gagccagtcc
aaccctaacc aaagttttca gttagcagca aataatttgt
atctctgggg accagggatc acttgatgag tggggctaat
ttcttaaaac cctggtgtgg aagaaataat tctgacaaag
gagaatgcgt gccccatatt tctctgcgtc tgaatagcta
aatgaccttg ggtgagtcac ttaagcttc agaggctcag
tttcctctcc tgtgcaacag
```

As described in the examples, NXTAR-N5 is an oligonucleotide derived from NXTAR exon 5, which has a significant ability to suppress AR and its variant AR-V7 mRNA expression as well as growth of prostate cancer cells.

SEQ ID NO: 58 is the LOC105373241 (NXTAR) and SEQ ID NO: 59 is the corresponding RNA sequence, ncRNA sequence. The NXTAR oligonucleotides can be derived from this as a truncated portion or variant, wherein the derived oligonucleotide can be RNA or DNA encoding RNA.

NXTAR-N5 (SEQ ID NO: 1), 60-mer oligonucleotide sequence, corresponding with nt 511-570 of SEQ ID NO: 58:

```
A*T*T*ATTATTTTAAATTTACAGAAGGGGAAACTAAGAATTATAGACAT
GAAGTGACTC*A*C*C
```

The * represents phosphorothioate bond modifications to avoid degradation by exonucleases.

NXAR-N7 (SEQ ID NO: 2), 30-mer oligonucleotide sequence, corresponding with nt 511-540 of SEQ ID NO: 58:

```
ATTATTATTTTAAATTTACAGAAGGGGAAA
```

NXTAR-N8 (SEQ ID NO: 3), 43-mer oligonucleotide sequence, corresponding with nt 528-570 of SEQ ID NO: 58:

```
ACAGAAGGGGAAACTAAGAATTATAGACATGAAGTGACTCACC
```

NXTAR-N9 (SEQ ID NO: 4), 33-mer oligonucleotide sequence, corresponding with nt 982-1014 of SEQ ID NO: 58:

```
CCACCACTAGGGTCCTGGCTACAACTGGCCCTC
```

NXTAR-N9 (Mod, SEQ ID NO: 5), 33-mer oligonucleotide sequence, corresponding with nt 982-1014 of SEQ ID NO: 58:

```
C*C*A*CCACTAGGGTOCTGGCTACAACTGGCC*C*T*C
```

The * represents a phosphorothioate bond modification to avoid degradation by exonucleases.

Additional derivatives of NXTAR, listed below, have also been synthesized.

Prancer-N5 (SEQ ID NO: 6), 60-mer oligonucleotide sequence, corresponding with 511-570 nt of NXTAR (SEQ ID NO: 58)):

```
5'-A*T*T* ATT ATT TTA AAT TTA CAG AAG GGG AAA CTA
AGA ATT ATA GAC ATG AAG TGA CTC* A*C*C -3'
```

*Represents a phosphorothioate bond modification to avoid degradation by exonucleases.

Prancer-N5-Forward (SEQ ID NO: 7), 60-mer (representing 511-570 nt of NXTAR (SEQ ID NO: 58)), identical to SEQ ID NO: 6 without the phosphorothioate bond modification:

```
5'-ATT ATT ATT TTA AAT TTA CAG AAG GGG AAA CTA AGA
ATT ATA GAC ATG AAG TGA CTC ACC -3'
```

Prancer-N5-Reverse (SEQ ID NO: 8) (reverse complement to SEQ ID NO: 7):

```
5'-GGT GAG TCA CTT CAT GTC TAT AAT TCT TAG TTT CCC
CTT CTG TAA ATT TAA AAT AAT AAT-3'
```

Sequence-N7 (SEQ ID NO: 9), 30-mer oligonucleotide sequence (representing 511-540 nt of NXTAR (SEQ ID NO: 58)), identical to SEQ ID NO: 2 with phosphorothioate bond modifications:

```
5'-A*T*T* ATT ATT TTA AAT TTA CAG AAG GGG* A*A*A-3'
```

The * represents a phosphorothioate bond modification to avoid degradation by exonucleases.

Sequence-N7 (RNA, SEQ ID NO: 10) (corresponding RNA sequence to SEQ ID NO: 9), 30-mer oligonucleotide sequence (representing 511-540 nt of SEQ ID NO: 9):

```
5'-rA*rU*rU* rArUrU rArUrU rUrUrA rArArU rUrUrA
rCrArG rArArG rGrGrG* rA*rA*rA-3'
```

The * represents a phosphorothioate bond modification to avoid degradation by exonucleases.

Sequence-N8 (SEQ ID NO: 11), a 43-mer modified sequence corresponding to nt 528-570 of SEQ ID NO: 58, identical to SEQ ID NO: 3 with phosphorothioate bond modifications:

```
5'-A*C*A* GAA GGG GAA ACT AAG AAT TAT AGA CAT GAA
GTG ACT C*A*C* C-3'
```

The * represents a phosphorothioate bond modification to avoid degradation by exonucleases.

Sequence-N8 (RNA, SEQ ID NO: 12) (corresponding RNA sequence to SEQ ID NO: 11), a 43-mer modified sequence corresponding to nt 528-570 of SEQ ID NO: 59:

```
5'-rA*rC*rA* rGrArA rGrGrG rGrArA rArCrU rArArG
rArArU rUrArU rArGrA rCrArU rGrArA rGrUrG rArCrU
rC*rA*rC* rC-3'
```

The * represents a phosphorothioate bond modification to avoid degradation by exonucleases.

RNA bases are entered with a lower-case "r" preceding the desired base (e.g., rA, rC, rG, rU).

Based on the data (see e.g., Example 2), it was observed that transfection/introduction of these oligos not only suppressed androgen receptor (AR) expression, but also inhibited proliferation of prostate and breast cancer cells. These oligos (DNA and RNA) have potential to be used as therapy in humans.

Prostate cancer (PC) is the second most reported cancer in American men. The limited efficacy of androgen deprivation therapies (ADT) often result in progression of disease to lethal castration resistant prostate cancer (CRPC) in about 1-2 years, with reversion of the androgen receptor (AR) activity. To combat CRPCs, Abiraterone, androgen biosynthesis inhibitor, and Enzalutamide, a drug that inhibits AR nuclear translocation have been widely employed, however, the overall disease-free survival for these two AR-antagonists as a single agent has been modest and the combination has provided a little advantage over single agent. Robust amplification of the AR enhancer region in almost 81% of Enzalutamide-treated patients reinforces the notion that AR signaling is the epicenter of drug-resistance. AR regulating its own expression by epigenetic modification of its own enhancer in Enzalutamide-rich environment has been another mechanism to maintain high AR levels. In addition, many CRPC patients developed resistance by expressing an AR splice variant, AR-V7, that lacks the ligand-binding domain, nullifying the effect of these two AR-antagonists, thus establishing that AR is not only important in the pre-CRPC scenario, but also, retains a dominant role in the post-CRPC stage.

Here is described the identification of a long non-coding RNA (lncRNA), NXTAR (LOC105373241), located convergently to the AR gene, that is not only repressed in human prostate tumors and cell lines, but it was also uncovered that its reinstation promoted its binding upstream of AR promoter, causing significant loss of AR and its splice variant AR-V7 expression.

Based on this observation, multiple oligonucleotides were designed, named NXTAR-N series, derived from NXTAR RNA sequence. Transfection of these oligos (both single and double-stranded RNAs and DNAs) in prostate cancer cells significantly suppressed AR and AR-V7 transcription levels, compromising their proliferation.

These oligos have considerable potential to be a new therapeutic modality, especially overcoming growth of the prostate, breast, testis, endometrial, ovarian, and skin cancers that express AR.

The oligos as described herein can be of any length suitable for suppressing AR expression, signaling, or activity. The oligos as described here can comprise at least about 1 residue; at least about 2 residues; at least about 3 residues; at least about 4 residues; at least about 5 residues; at least about 6 residues; at least about 7 residues; at least about 8 residues; at least about 9 residues; at least about 10 residues; at least about 11 residues; at least about 12 residues; at least about 13 residues; at least about 14 residues; at least about 15 residues; at least about 16 residues; at least about 17 residues; at least about 18 residues; at least about 19 residues; at least about 20 residues; at least about 21 residues; at least about 22 residues; at least about 23 residues; at least about 24 residues; at least about 25 residues; at least about 26 residues; at least about 27 residues; at least about 28 residues; at least about 29 residues; at least about 30 residues; at least about 31 residues; at least about 32 residues; at least about 33 residues; at least about 34 residues; at least about 35 residues; at least about 36 residues; at least about 37 residues; at least about 38 residues; at least about 39 residues; at least about 40 residues; at least about 41 residues; at least about 42 residues; at least about 43 residues; at least about 44 residues; at least about 45 residues; at least about 46 residues; at least about 47 residues; at least about 48 residues; at least about 49 residues; at least about 50 residues; at least about 51 residues; at least about 52 residues; at least about 53 residues; at least about 54 residues; at least about 55 residues; at least about 56 residues; at least about 57 residues; at least about 58 residues; at least about 59 residues; at least about 60 residues; at least about 61 residues; at least about 62 residues; at least about 63 residues; at least about 64 residues; at least about 65 residues; at least about 66 residues; at least about 67 residues; at least about 68 residues; at least about 69 residues; at least about 70 residues; at least about 71 residues; at least about 72 residues; at least about 73 residues; at least about 74 residues; at least about 75 residues; at least about 76 residues; at least about 77 residues; at least about 78 residues; at least about 79 residues; at least about 80 residues; at least about 81 residues; at least about 82 residues; at least about 83 residues; at least about 84 residues; at least about 85 residues; at least about 86 residues; at least about 87 residues; at least about 88 residues; at least about 89 residues; at least about 90 residues; at least about 91 residues; at least about 92 residues; at least about 93 residues; at least about 94 residues; at least about 95 residues; at least about 96 residues; at least about 97 residues; at least about 98 residues; at least about 99 residues; at least about 100 residues; at least about 101 residues; at least about 102 residues; at least about 103 residues; at least about 104 residues; at least about 105 residues; at least about 106 residues; at least about 107 residues; at least about 108 residues; at least about 109 residues; at least about 110 residues; at least about 111 residues; at least about 112 residues; at least about 113 residues; at least about 114 residues; at least about 115 residues; at least about 116 residues; at least about 117 residues; at least about 118 residues; at least about 119 residues; at least about 120 residues; at least about 121 residues; at least about 122 residues; at least about 123 residues; at least about 124 residues; at least about 125 residues; at least about 126 residues; at least about 127 residues; at least about 128 residues; at least about 129 residues; at least about 130 residues; at least about 131 residues; at least about 132 residues; at least about 133 residues; at least about 134 residues; at least about 135 residues; at least about 136 residues; at least about 137 residues; at least about 138 residues; at least about 139 residues; at least about 140 residues; at least about 141 residues; at least about 142 residues; at least about 143 residues; at least about 144 residues; at least about 145 residues; at least about 146 residues; at least about 147 residues; at least about 148 residues; at least about 149 residues; at least about 150 residues; at least about 151 residues; at least about 152 residues; at least about 153 residues; at least about 154 residues; at least about 155 residues; at least about 156 residues; at least about 157 residues; at least about 158 residues; at least about 159 residues; at least about 160 residues; at least about 161 residues; at least about 162 residues; at least about 163 residues; at least about 164 residues; at least about 165 residues; at least about 166 residues; at least about 167 residues; at least about 168 residues; at least about 169 residues; at least about 170 residues; at least about 171 residues; at least about 172 residues; at least about 173 residues; at least about 174 residues; at least about 175 residues; at least about 176 residues; at least about 177 residues; at least about 178 residues; at least about 179 residues; at least about 180 residues; at least about 181 residues; at least about 182 residues; at least about 183 residues; at least about 184 residues; at least about 185 residues; at least about 186 residues; at least about 187 residues; at least about 188 residues; at least about 189 residues; at least about 190 residues; at least about 191 residues; at least about 192 residues; at least about 193 residues; at least about 194 residues; at least about 195 residues; at least about 196 residues; at least about 197 residues; at least about 198 residues; at least about 199 residues; or at least about 200 residues.

The NXTAR-derived oligonucleotides as described herein can have a percent identity to a portion of NXTAR or percent homology to a portion of AR or a portion of the AR promoter region (or reverse strand, complementary strand, or reverse-complementary strand, corresponding DNA or RNA, single- or double-stranded DNA or RNA, thereof) of about 1%; about 2%; about 3%; about 4%; about 5%; about 6%; about 7%; about 8%; about 9%; about 10%; about 11%; about 12%; about 13%; about 14%; about 15%; about 16%;

about 17%; about 18%; about 19%; about 20%; about 21%; about 22%; about 23%; about 24%; about 25%; about 26%; about 27%; about 28%; about 29%; about 30%; about 31%; about 32%; about 33%; about 34%; about 35%; about 36%; about 37%; about 38%; about 39%; about 40%; about 41%; about 42%; about 43%; about 44%; about 45%; about 46%; about 47%; about 48%; about 49%; about 50%; about 51%; about 52%; about 53%; about 54%; about 55%; about 56%; about 57%; about 58%; about 59%; about 60%; about 61%; about 62%; about 63%; about 64%; about 65%; about 66%; about 67%; about 68%; about 69%; about 70%; about 71%; about 72%; about 73%; about 74%; about 75%; about 76%; about 77%; about 78%; about 79%; about 80%; about 81%; about 82%; about 83%; about 84%; about 85%; about 86%; about 87%; about 88%; about 89%; about 90%; about 91%; about 92%; about 93%; about 94%; about 95%; about 96%; about 97%; about 98%; about 99%; or about 100%.

Androgen Receptor-Associated Diseases, Disorders, and Conditions

Androgen receptors (ARs) are expressed on a variety of cell types, and AR signaling plays an important role in tumor development and progression in several cancers. AR-associated cancers can include Prostate Cancer, Breast Cancer, Melanoma, Multiple Myeloma, Pancreatic Cancer, Bladder Cancer, Rhabdomyosarcoma, or any cancer or metastatic cancers having increased AR expression.

Any cancer having increased AR expression, signaling, or activity can be treated with the agents described herein. For example, the cancer can be Acute Lymphoblastic Leukemia (ALL); Acute Myeloid Leukemia (AML); Adrenocortical Carcinoma; AIDS-Related Cancers; Kaposi Sarcoma (Soft Tissue Sarcoma); AIDS-Related Lymphoma (Lymphoma); Primary CNS Lymphoma (Lymphoma); Anal Cancer; Appendix Cancer; Gastrointestinal Carcinoid Tumors; Astrocytomas; Atypical Teratoid/Rhabdoid Tumor, Childhood, Central Nervous System (Brain Cancer); Basal Cell Carcinoma of the Skin; Bile Duct Cancer; Bladder Cancer; Bone Cancer (including Ewing Sarcoma and Osteosarcoma and Malignant Fibrous Histiocytoma); Brain Tumors; Breast Cancer; Bronchial Tumors; Burkitt Lymphoma; Carcinoid Tumor (Gastrointestinal); Childhood Carcinoid Tumors; Cardiac (Heart) Tumors; Central Nervous System cancer; Atypical Teratoid/Rhabdoid Tumor, Childhood (Brain Cancer); Embryonal Tumors, Childhood (Brain Cancer); Germ Cell Tumor, Childhood (Brain Cancer); Primary CNS Lymphoma; Cervical Cancer; Cholangiocarcinoma; Bile Duct Cancer Chordoma; Chronic Lymphocytic Leukemia (CLL); Chronic Myelogenous Leukemia (CML); Chronic Myeloproliferative Neoplasms; Colorectal Cancer; Craniopharyngioma (Brain Cancer); Cutaneous T-Cell; Ductal Carcinoma In Situ (DCIS); Embryonal Tumors, Central Nervous System, Childhood (Brain Cancer); Endometrial Cancer (Uterine Cancer); Ependymoma, Childhood (Brain Cancer); Esophageal Cancer; Esthesioneuroblastoma; Ewing Sarcoma (Bone Cancer); Extracranial Germ Cell Tumor; Extragonadal Germ Cell Tumor; Eye Cancer; Intraocular Melanoma; Intraocular Melanoma; Retinoblastoma; Fallopian Tube Cancer; Fibrous Histiocytoma of Bone, Malignant, or Osteosarcoma; Gallbladder Cancer; Gastric (Stomach) Cancer; Gastrointestinal Carcinoid Tumor; Gastrointestinal Stromal Tumors (GIST) (Soft Tissue Sarcoma); Germ Cell Tumors; Central Nervous System Germ Cell Tumors (Brain Cancer); Childhood Extracranial Germ Cell Tumors; Extragonadal Germ Cell Tumors; Ovarian Germ Cell Tumors; Testicular Cancer; Gestational Trophoblastic Disease; Hairy Cell Leukemia; Head and Neck Cancer; Heart Tumors; Hepatocellular (Liver) Cancer; Histiocytosis, Langerhans Cell; Hodgkin Lymphoma; Hypopharyngeal Cancer; Intraocular Melanoma; Islet Cell Tumors; Pancreatic Neuroendocrine Tumors; Kaposi Sarcoma (Soft Tissue Sarcoma); Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Lymphoma; Male Breast Cancer; Malignant Fibrous Histiocytoma of Bone or Osteosarcoma; Melanoma; Melanoma, Intraocular (Eye); Merkel Cell Carcinoma (Skin Cancer); Mesothelioma, Malignant; Metastatic Cancer; Metastatic Squamous Neck Cancer with Occult Primary; Midline Tract Carcinoma Involving NUT Gene; Mouth Cancer; Multiple Endocrine Neoplasia Syndromes; Multiple Myeloma/Plasma Cell Neoplasms; Mycosis Fungoides (Lymphoma); Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip or Oral Cavity Cancer; Oropharyngeal Cancer; Osteosarcoma and Malignant Fibrous Histiocytoma of Bone; Ovarian Cancer Pancreatic Cancer; Pancreatic Neuroendocrine Tumors (Islet Cell Tumors); Papillomatosis; Paraganglioma; Paranasal Sinus and Nasal Cavity Cancer; Parathyroid Cancer; Penile Cancer; Pharyngeal Cancer; Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer Renal Cell (Kidney) Cancer; Retinoblastoma; Rhabdomyosarcoma, Childhood (Soft Tissue Sarcoma); Salivary Gland Cancer; Sarcoma; Childhood Rhabdomyosarcoma (Soft Tissue Sarcoma); Childhood Vascular Tumors (Soft Tissue Sarcoma); Ewing Sarcoma (Bone Cancer); Kaposi Sarcoma (Soft Tissue Sarcoma); Osteosarcoma (Bone Cancer); Uterine Sarcoma; Sezary Syndrome (Lymphoma); Skin Cancer; Small Cell Lung Cancer; Small Intestine Cancer; Soft Tissue Sarcoma; Squamous Cell Carcinoma of the Skin or oral Squamous Cell Carcinoma; Squamous Neck Cancer with Occult Primary, Metastatic; Stomach (Gastric) Cancer; T-Cell Lymphoma, Cutaneous; Lymphoma; Mycosis Fungoides and Sezary Syndrome; Testicular Cancer; Throat Cancer; Nasopharyngeal Cancer; Oropharyngeal Cancer; Hypopharyngeal Cancer; Thymoma and Thymic Carcinoma; Thyroid Cancer; Thyroid Tumors; Transitional Cell Cancer of the Renal Pelvis and Ureter (Kidney (Renal Cell) Cancer); Ureter and Renal Pelvis; Transitional Cell Cancer (Kidney (Renal Cell) Cancer); Urethral Cancer; Uterine Cancer, Endometrial; Uterine Sarcoma; Vaginal Cancer; Vascular Tumors (Soft Tissue Sarcoma); Vulvar Cancer; or Wilms Tumor. Brain or spinal cord tumors can be acoustic neuroma; astrocytoma, atypical teratoid rhabdoid tumor (ATRT); brain stem glioma, chordoma; chondrosarcoma; choroid plexus; CNS lymphoma; craniopharyngioma; cysts; ependymoma; ganglioglioma; germ cell tumor; glioblastoma (GBM); glioma, hemangioma; juvenile pilocytic astrocytoma (JPA); lipoma; lymphoma; medulloblastoma; meningioma; metastatic brain tumor; neurilemmomas; neurofibroma; neuronal & mixed neuronal-glial tumors; non-Hodgkin lymphoma; oligoastrocytoma; oligodendroglioma; optic nerve glioma, pineal tumor; pituitary tumor; primitive neuroectodermal (PNET); rhabdoid tumor; or schwannoma. An astrocytoma can be grade I pilocytic astrocytoma, grade II-low-grade astrocytoma, grade III anaplastic astrocytoma, or grade IV glioblastoma (GBM), or a juvenile pilocytic astrocytoma. A glioma can be a brain stem glioma, ependymoma, mixed glioma, optic nerve glioma, or subependymoma.

The agents described herein can be used as an antiandrogen agent or in combination with antiandrogens (e.g., androgen antagonists, androgen receptor blockers, testosterone blockers) can be used in the treatment of various conditions and disorders including prostate cancer, precocious puberty in young males, benign prostatic hyperplasia, androgenic alopecia (male-pattern hair loss) and sexual disorders, such as hyper-sexuality, in men. In women, antiandrogens may be used to treat polycystic ovary syndrome, hirsutism (excessive facial or body hair), feminizing therapy, amenorrhea (absence of menstrual periods), acne, and several other conditions, such as AR-expressing skin disease, androgenetic alopecia, or acne vulgaris.

AR-Targeted Drugs

Currently, AR-targeted therapies can be any medicines that counteract the effects of the male sex hormones, testosterone, and dihydrotestosterone. Male sex hormones are also known as androgens; antiandrogens may also be called androgen receptor blockers. Some antiandrogens work by lowering the body's production of androgens while others block androgen receptors, limiting the body's ability to make use of the androgens produced.

Abiraterone, a class of drugs known as anti-androgens (anti-testosterone); Flutamide, an antiandrogen used for locally confined stage B2-C and D-2 metastatic prostate carcinoma; Nilutamide, an antineoplastic hormone used to treat prostate cancer; Bicalutamide, an androgen receptor inhibitor used to treat Stage D2 metastatic carcinoma of the prostate; Enzalutamide, an androgen receptor inhibitor used to treat castration-resistant prostate cancer; Clascoterone, an androgen receptor antagonist used for the topical treatment of acne vulgaris in patients 12 years of age and older; Apalutamide, an androgen receptor inhibitor used to treat non metastatic, castration resistant prostate cancer; or Darolutamide, an androgen receptor antagonist used for castration-resistant, non-metastatic prostate cancer.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The term "transfection," as used herein, refers to the process of introducing nucleic acids into cells by non-viral methods. The term "transduction," as used herein, refers to the process whereby foreign DNA is introduced into another cell via a viral vector.

The terms "heterologous DNA sequence", "exogenous DNA segment", or "heterologous nucleic acid," as used herein, each refers to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling or cloning. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Sequences described herein can also be the reverse, the complement, or the reverse complement of the nucleotide sequences described herein. The RNA goes in the reverse direction compared to the DNA, but its base pairs still match (e.g., G to C). The reverse complementary RNA for a positive strand DNA sequence will be identical to the corresponding negative strand DNA sequence. Reverse complement converts a DNA sequence into its reverse, complement, or reverse-complement counterpart.

| Base | Name | Bases Represented | Complementary Base |
|---|---|---|---|
| A | Adenine | A | T |
| T | Thymidine | T | A |
| U | Uridine (RNA only) | U | A |
| G | Guanidine | G | C |
| C | Cytidine | C | G |
| Y | pYrimidine | C T | R |
| R | puRine | A G | Y |
| S | Strong (3Hbonds) | G C | S* |
| W | Weak (2Hbonds) | A T | W* |
| K | Keto | T/U G | M |
| M | aMino | A C | K |
| B | not A | C G T | V |
| D | not C | A G T | H |
| H | not G | A C T | D |
| V | not T/U | A C G | B |
| N | Unknown | A C G T | N |

Complementarity is a property shared between two nucleic acid sequences (e.g., RNA, DNA), such that when they are aligned antiparallel to each other, the nucleotide bases at each position will be complementary. Two bases are complementary if they form Watson-Crick base pairs.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

An "expression vector", otherwise known as an "expression construct", is generally a plasmid or virus designed for gene expression in cells. The vector is used to introduce a specific gene into a target cell, and can commandeer the cell's mechanism for protein synthesis to produce the protein encoded by the gene. Expression vectors are the basic tools in biotechnology for the production of proteins. The vector is engineered to contain regulatory sequences that act as enhancer and/or promoter regions and lead to efficient transcription of the gene carried on the expression vector. The goal of a well-designed expression vector is the efficient production of protein, and this may be achieved by the production of significant amount of stable messenger RNA, which can then be translated into protein. The expression of a protein may be tightly controlled, and the protein is only produced in significant quantity when necessary through the use of an inducer, in some systems however the protein may be expressed constitutively. As described herein, *Escherichia coli* is used as the host for protein production, but other cell types may also be used.

In molecular biology, an "inducer" is a molecule that regulates gene expression. An inducer can function in two ways, such as:

(i) By disabling repressors. The gene is expressed because an inducer binds to the repressor. The binding of the inducer to the repressor prevents the repressor from binding to the operator. RNA polymerase can then begin to transcribe operon genes.

(ii) By binding to activators. Activators generally bind poorly to activator DNA sequences unless an inducer is present. An activator binds to an inducer and the complex binds to the activation sequence and activates target gene. Removing the inducer stops transcription. Because a small inducer molecule is required, the increased expression of the target gene is called induction.

Repressor proteins bind to the DNA strand and prevent RNA polymerase from being able to attach to the DNA and synthesize mRNA. Inducers bind to repressors, causing them to change shape and preventing them from binding to DNA. Therefore, they allow transcription, and thus gene expression, to take place.

For a gene to be expressed, its DNA sequence must be copied (in a process known as transcription) to make a smaller, mobile molecule called messenger RNA (mRNA), which carries the instructions for making a protein to the site where the protein is manufactured (in a process known as translation). Many different types of proteins can affect the level of gene expression by promoting or preventing transcription. In prokaryotes (such as bacteria), these proteins often act on a portion of DNA known as the operator at the beginning of the gene. The promoter is where RNA polymerase, the enzyme that copies the genetic sequence and synthesizes the mRNA, attaches to the DNA strand.

Some genes are modulated by activators, which have the opposite effect on gene expression as repressors. Inducers can also bind to activator proteins, allowing them to bind to the operator DNA where they promote RNA transcription. Ligands that bind to deactivate activator proteins are not, in the technical sense, classified as inducers, since they have the effect of preventing transcription.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "ribosome binding site", or "ribosomal binding site (RBS)", refers to a sequence of nucleotides upstream of the start codon of an mRNA transcript that is responsible for the recruitment of a ribosome during the initiation of translation. Generally, RBS refers to bacterial sequences, although internal ribosome entry sites (IRES) have been described in mRNAs of eukaryotic cells or viruses that infect eukaryotes. Ribosome recruitment in eukaryotes is generally mediated by the 5' cap present on eukaryotic mRNAs.

A "transcribable nucleic acid molecule" as used herein refers to any nucleic acid molecule capable of being transcribed into an RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A construct of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal, or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above-required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

For example, a NEXTAR-derived oligonucleotide can have a percent identity of about 80%; about 81%; about 82%; about 83%; about 84%; about 85%; about 86%; about 87%; about 88%; about 89%; about 90%; about 91%; about 92%; about 93%; about 94%; about 95%; about 96%; about 97%; about 98%; about 99%; or about 100% of a fragment, segment, or portion of NEXTAR or the identified sequences described herein. The NEXTAR-derived oligonucleotide having at least 80% identity can have NEXTAR-related activity, such as AR suppression.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2, or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y 100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A. For example, the percent identity can be at least 80% or about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

Substitution refers to the replacement of one amino acid with another amino acid in a protein or the replacement of one nucleotide with another in DNA or RNA. Insertion refers to the insertion of one or more amino acids in a protein or the insertion of one or more nucleotides with another in DNA or RNA. Deletion refers to the deletion of one or more amino acids in a protein or the deletion of one or more nucleotides with another in DNA or RNA. Generally, substitutions, insertions, or deletions can be made at any position so long as the required activity is retained.

So-called conservative exchanges can be carried out in which the amino acid which is replaced has a similar property as the original amino acid, for example, the exchange of Glu by Asp, Gln by Asn, Val by Ile, Leu by Ile, and Ser by Thr. For example, amino acids with similar properties can be Aliphatic amino acids (e.g., Glycine, Alanine, Valine, Leucine, Isoleucine), hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. An amino acid sequence can be modulated with the help of art-known computer simulation programs that can produce a polypeptide with, for example, improved activity or altered regulation. On the basis of these artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[$Na^+$])+0.41(fraction G/C content)−

0.63(% formamide)−(600/l). Furthermore, the $T_m$ of a DNA: DNA hybrid is decreased by 1-1.5° C. for every 1% decrease in nucleotide identity (see e.g., Sambrook and Russel, 2006).

Host cells can be transformed using a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Conservative Substitutions I

| Side Chain Characteristic | Amino Acid |
|---|---|
| Aliphatic Non-polar | G A P I L V |
| Polar-uncharged | C S T M N Q |
| Polar-charged | D E K R |
| Aromatic | H F W Y |
| Other | N Q D E |

Conservative Substitutions II

| Side Chain Characteristic | Amino Acid |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met(M) | Leu, Phe, Ile |
| Phe (F) | Leu, Val, Ile, Ala |
| Pro (P) | Gly |
| Ser (S) | Thr |
| Thr (T) | Ser |
| Trp(W) | Tyr, Phe |
| Tyr (Y) | Trp, Phe, Tur, Ser |
| Val (V) | Ile, Leu, Met, Phe, Ala |

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA that is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides (ASOs), protein aptamers, nucleotide aptamers, and RNA interference (RNAi) (e.g., small interfering RNAs (siRNA), short hairpin RNA (shRNA), single guide RNA (sgRNA), micro RNAs (miRNA) (see e.g., Rinaldi and Wood (2017) Nature Reviews Neurology 14, describing ASO therapies; Fanning and Symonds (2006) Handb Exp Pharmacol. 173, 289-303G, describing hammerhead ribozymes and small hairpin RNA; Helene, et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Genome Editing

As described herein, androgen receptor (AR) or NXTAR signals can be modulated (e.g., reduced, eliminated, or enhanced) using genome editing. Processes for genome editing are well known; see e.g. Aldi 2018 Nature Communications 9(1911). Except as otherwise noted herein, therefore, the process of the present disclosure can be carried out in accordance with such processes.

For example, genome editing can comprise CRISPR/Cas9, CRISPR-Cpf1, TALEN, or ZNFs. Adequate blockage of AR or enhancement of NXTAR by genome editing can result in protection from proliferative diseases, such as cancer or other AR-associated diseases, disorders, or conditions.

As an example, clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a $(N)_{20}NGG$ target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, genomic editing, for example, using CRISPR/Cas systems could be useful tools for therapeutic applications for treating cancer to target cells by the removal or addition of AR or NXTAR signals (e.g., activate (e.g., CRISPRa), upregulate, overexpress, downregulate AR or NXTAR).

For example, the methods as described herein can comprise a method for altering a target polynucleotide sequence in a cell comprising contacting the polynucleotide sequence with a clustered regularly interspaced short palindromic repeats-associated (Cas) protein.

Gene Therapy and Genome Editing

Gene therapies can include inserting a functional gene with a viral vector. Gene therapies for treatment or prevention of cancer are rapidly advancing.

There has recently been an improved landscape for gene therapies. For example, in the first quarter of 2019, there were 372 ongoing gene therapy clinical trials (*Alliance for Regenerative Medicine,* 5/9/19).

Any vector known in the art can be used. For example, the vector can be a viral vector selected from retrovirus, lentivirus, herpes, adenovirus, adeno-associated virus (AAV), rabies, Ebola, lentivirus, or hybrids thereof.

Gene therapy strategies.

| | Strategy | Associated experimental models |
|---|---|---|
| **Viral Vectors** | | |
| Retroviruses | Retroviruses are RNA viruses transcribing their single-stranded genome into a double-stranded DNA copy, which can integrate into host chromosome | Murine model of MPS VII<br>Canine model of MPS VII |
| Adenoviruses (Ad) | Ad can transfect a variety of quiescent and proliferating cell types from various species and can mediate robust gene expression | Murine model of Pompe, Fabry, Walman diseases, aspartylglucosaminuria and MPS VII |
| Adeno-associated Viruses (AAV) | Recombinant AAV vectors contain no viral DNA and can carry ~4.7 kb of foreign transgenic material. They are replication defective and can replicate only while coinfecting with a helper virus | Murine models of Pompe, Fabry diseases, Aspartylglucosaminuria, Krabbe disease, Metachromatic leukodystrophy, MPS I, MPSII, MPSIIIA, MPSIIIB, MPSIV, MPSVI, MPS VII, CLN1, CLN2, CLN3, CLN5, CLN6 |
| **Non-viral vectors** | | |
| plasmid DNA (pDNA) | pDNA has many desired characteristics as a gene therapy vector; there are no limits on the size or genetic constitution of DNA, it is relatively inexpensive to supply, and unlike viruses, antibodies are not generated against DNA in normal individuals | Mouse model of Fabry disease |

-continued

| Gene therapy strategies. | | |
|---|---|---|
| | Strategy | Associated experimental models |
| RNAi | RNAi is a powerful tool for gene specific silencing that could be useful as an enzyme reduction therapy or means to promote read-through of a premature stop codon | Transgenic mouse strain<br>Mouse models of acute liver failure<br>Mice with hepatitis B virus<br>Fabry mouse |

Gene therapy can allow for the constant delivery of the enzyme directly to target organs and eliminates the need for weekly infusions. Also, correction of a few cells could lead to the enzyme being secreted into the circulation and taken up by their neighboring cells (cross-correction), resulting in widespread correction of the biochemical defects. As such, the number of cells that must be modified with a gene transfer vector is relatively low.

Genetic modification can be performed either ex vivo or in vivo. The ex vivo strategy is based on the modification of cells in culture and transplantation of the modified cell into a patient. Cells that are most commonly considered therapeutic targets for monogenic diseases are stem cells. Advances in the collection and isolation of these cells from a variety of sources have promoted autologous gene therapy as a viable option.

The use of endonucleases for targeted genome editing can solve the limitations presented by the usual gene therapy protocols. These enzymes are custom molecular scissors, allowing cutting DNA into well-defined, perfectly specified pieces, in virtually all cell types. Moreover, they can be delivered to the cells by plasmids that transiently express the nucleases, or by transcribed RNA, avoiding the use of viruses.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutically active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic, or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating, preventing, or reversing cancer in a subject in need of administration of a therapeutically effective amount of a NXTAR-derived oligonucleotide, so as to suppress AR, suppress AR variants including AR-V7, inhibit proliferation of cancer cells (e.g., breast, prostate, testis, ovarian, endometrial, skin), treat AR-related diseases, treat AR-related skin diseases (e.g., androgenetic alopecia, acne vulgaris). It may play important roles in suppressing AR activity in several skin related diseases, such as androgenetic alopecia or acne vulgaris.

Methods described herein are generally performed on a subject in need thereof. A subject in need of the therapeutic methods described herein can be a subject having, diagnosed with, suspected of having, or at risk for developing cancer or other AR-related diseases. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of a NXTAR-derived oligonucleotide is, for example, an amount that would cause the desired therapeutic effect in a subject while minimizing undesired side effects. In various embodiments, an effective amount of a NXTAR-derived oligonucleotide described herein can substantially inhibit or suppress expression of AR or AR-V7 (e.g., in AR-related diseases), slow the progress of cancer, or limit the development of cancer, such as cancers associated with AR- or AR-V7 overexpression. In various embodiments, an effective amount of a NXTAR-derived oligonucleotide described herein can substantially inhibit or suppress expression of AR and slow the progress of skin related diseases, such as androgenetic alopecia and acne vulgaris.

According to the methods described herein, administration can be parenteral, pulmonary, oral, topical, intradermal, intramuscular, intraperitoneal, intravenous, intratumoral, intrathecal, intracranial, intracerebroventricular, subcutaneous, intranasal, epidural, ophthalmic, buccal, or rectal administration.

When used in the treatments described herein, a therapeutically effective amount of a NXTAR-derived oligonucleotide can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to substantially inhibit or suppress expression of AR or AR-V7 (e.g., in AR-related diseases), slow the progress of cancer, or limit the development of cancer, such as cancers associated with AR- or AR-V7 overexpression.

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing, reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or a physician.

Administration of a NXTAR-derived oligonucleotide can occur as a single event or over a time course of treatment. For example, a NXTAR-derived oligonucleotide can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to or before, concurrent with, or after conventional treatment modalities for cancer.

A NXTAR-derived oligonucleotide can be administered simultaneously or sequentially with another agent or therapy, such as an anti-cancer agent, an antibiotic, an anti-inflammatory, or another agent, such as an ACK1/TNK2 tyrosine kinase inhibiting agent (e.g., (R)-9b). For example, a NXTAR-derived oligonucleotide can be administered simultaneously with another agent or therapy, such as an anti-cancer agent, an ACK1/TNK2 tyrosine kinase inhibiting agent, an antibiotic, or an anti-inflammatory. Simultaneous administration can occur through administration of separate compositions, each containing one or more of a NXTAR-derived oligonucleotide, an anti-cancer agent, an ACK1/TNK2 tyrosine kinase inhibiting agent, an antibiotic, an anti-inflammatory, or another agent. Simultaneous administration can occur through administration of one composition containing two or more of a NXTAR-derived oligonucleotide, an anti-cancer agent, an ACK1/TNK2 tyrosine kinase inhibiting agent, an antibiotic, an anti-inflammatory, or another agent. A NXTAR-derived oligonucleotide can be administered sequentially with an anti-cancer agent, an ACK1/TNK2 tyrosine kinase inhibiting agent, an antibiotic, an anti-inflammatory, or another agent. For example, a NXTAR-derived oligonucleotide can be administered before or after administration of an anti-cancer agent, an ACK1/TNK2 tyrosine kinase inhibiting agent, an antibiotic, an anti-inflammatory, or another agent.

Active compounds are administered at a therapeutically effective dosage sufficient to treat a condition associated with a condition in a patient. For example, the efficacy of a compound can be evaluated in an animal model system that may be predictive of efficacy in treating the disease in a human or another animal, such as the model systems shown in the examples and drawings.

An effective dose range of a therapeutic can be extrapolated from effective doses determined in animal studies for a variety of different animals. In general, a human equivalent dose (HED) in mg/kg can be calculated in accordance with the following formula (see e.g., Reagan-Shaw et al., *FASEB J.,* 22(3):659-661, 2008, which is incorporated herein by reference):

$$\text{HED (mg/kg)}=\text{Animal dose (mg/kg)}\times(\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 $m^2$) is 37, whereas a 20 kg child (BSA 0.8 $m^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment, and the potency, stability, and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

Cell Therapy

Cells generated according to the methods described herein can be used in cell therapy. Cell therapy (also called cellular therapy, cell transplantation, or cytotherapy) can be a therapy in which viable cells are injected, grafted, or implanted into a patient in order to effectuate a medicinal effect or therapeutic benefit. For example, transplanting T-cells capable of fighting cancer cells via cell-mediated immunity can be used in the course of immunotherapy, grafting stem cells can be used to regenerate diseased tissues, or transplanting beta cells can be used to treat diabetes.

Stem cell and cell transplantation has gained significant interest by researchers as a potential new therapeutic strategy for a wide range of diseases, in particular for degenerative and immunogenic pathologies.

Allogeneic cell therapy or allogenic transplantation uses donor cells from a different subject than the recipient of the cells. A benefit of an allogeneic strategy is that unmatched allogenic cell therapies can form the basis of “off the shelf” products.

Autologous cell therapy or autologous transplantation uses cells that are derived from the subject’s own tissues. It could also involve the isolation of matured cells from diseased tissues, to be later re-implanted at the same or neighboring tissues. A benefit of an autologous strategy is that there is limited concern for immunogenic responses or transplant rejection.

Xenogeneic cell therapies or xenotransplantation uses cells from another species. For example, pig derived cells can be transplanted into humans. Xenogeneic cell therapies can involve human cell transplantation into experimental animal models for assessment of efficacy and safety or enable xenogeneic strategies to humans as well.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency; improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to NXTAR-derived oligonucleotides and optionally pharmaceutical carriers or reagents. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, or sterile saline each of which has been packaged under a neutral non-reacting gas, such as nitrogen. Ampules may consist of any suitable material, such as glass, organic polymers, such as polycarbonate, polystyrene, ceramic, metal, or any other material typically employed to hold reagents. Other examples of suitable containers include bottles that may be fabricated from similar substances as ampules and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or another substrate, and/or may be supplied as an electronic-readable medium or video. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: NXTAR-N Series, a New Cancer Therapeutic Oligonucleotide

New oligos, dubbed NXTAR-N series of oligos, were developed as a new therapeutic modality for cancer such as prostate and some breast cancers. These oligos are derived from a newly identified long non-coding RNA (lncRNA) that was named NXTAR (also known as LOC105373241). NXTAR is located convergent to the androgen receptor (AR) gene, which is not only repressed in human prostate tumors and cell lines, but it was also uncovered that its reinstation promoted its binding upstream of AR promoter, causing significant loss of AR and its splice variant AR-V7 expression.

These oligos, in the form of single or double stranded DNA or RNA, suppress AR expression in prostate and other cancer cell lines. In particular, oligonucleotide NXTAR-N5 is highly effective (see e.g., Example 2).

Described herein is an oligonucleotide, NXTAR-N5 which has significant ability to suppress AR and its variant AR-V7 mRNA expression as well as growth of prostate cancer cells. This 60-mer oligonucleotide sequence is as follows.

```
NXTAR-N5
                                        (SEQ ID NO: 1)
A*T*T*ATTATTTTAAATTTACAGAAGGGGAAACTAAGAATTATAGACAT

GAAGTGACTC*A*C*C
```

The * represents phosphorothioate bond modifications to avoid degradation by exonucleases.

```
NXTAR-N7 (SEQ ID NO: 2):
ATTATTATTTTAAATTTACAGAAGGGGAAA

NXTAR-N8 (SEQ ID NO: 3):
ACAGAAGGGGAAACTAAGAATTATAGACATGAAGTGACTCACC
```

The 33-mer oligonucleotide sequence (representing 982-1014 nt of NXTAR mRNA) is as follows:

```
NXTAR-N9 (Reg, SEQ ID NO: 4):
CCA CCA CTA GGG TCC TGG CTA CAA CTG GCC CTC

NXTAR-N9 (Mod, SEQ ID NO: 5):
C*C*A*CCACTAGGGTCCTGGCTACAACTGGCC*C*T*C
```

Multiple additional derivatives of NXTAR, listed below, have also been synthesized.

```
Prancer-N5 (SEQ ID NO: 6):
5'-A*T*T* ATT ATT TTA AAT TTA CAG AAG GGG AAA CTA

AGA ATT ATA GAC ATG AAG TGA CTC* A*C*C-3'
```

*Represents a phosphorothioate bond modification to avoid degradation by exonucleases.

```
Prancer-N5-Forward (SEQ ID NO: 7):
5'-ATT ATT ATT TTA AAT TTA CAG AAG GGG AAA CTA

AGA ATT ATA GAC ATG AAG TGA CTC ACC-3'

Prancer-N5-Reverse (SEQ ID NO: 8):
5'-GGT GAG TCA CTT CAT GTC TAT AAT TCT TAG TTT

CCC CTT CTG TAA ATT TAA AAT AAT AAT-3'

Sequence-N7 (SEQ ID NO: 9):
5'-A*T*T* ATT ATT TTA AAT TTA CAG AAG GGG* A*A*A-3'

Sequence-N7 (RNA, SEQ ID NO: 10):
5'-rA*rU*rU* rArUrU rArUrU rUrUrA rArArU rUrUrA

rCrArG rArArG rGrGrG* rA*rA*rA-3'

Sequence-N8 (SEQ ID NO: 11):
5'-A*C*A* GAA GGG GAA ACT AAG AAT TAT AGA CAT GAA

GTG ACT C*A*C* C-3'

Sequence-N8 (RNA, SEQ ID NO: 12):
5'-rA*rC*rA* rGrArA rGrGrG rGrArA rArCrU rArArG

rArArU rUrArU rArGrA rCrArU rGrArA rGrUrG rArCrU

rC*rA*rC* rC-3'
```

Example 2: Loss of Long Non-Coding RNA NXTAR in Prostate Cancer Augments Androgen Receptor Expression and Enzalutamide Resistance This example identifies NXTAR as a tumor suppressive lncRNA that can epigenetically downregulate AR/AR-V7 expression and provides a therapeutic strategy to reinstate NXTAR expression for treating recurrent CRPC. It was discovered here that truncated portions of the lncRNA and corresponding single or double stranded DNA or RNA can be used to suppress AR. As such, this example describes the application of an oligonucleotide derived from NXTAR exon 5 (NXTARN5) suppressed AR/AR-V7 expression and prostate cancer cell proliferation, indicating the translational relevance of the negative regulation of AR. This example further describes the pharmacological restoration of NXTAR using (R)-9b abrogated enzalutamide-resistant prostate xenograft tumor growth.

Overall, this study uncovers a positive feedback loop, wherein NXTAR acts as a novel prostate tumor-suppressing lncRNA by inhibiting AR/AR-V7 expression, which in turn upregulates NXTAR levels, compromising enzalutamide-resistant prostate cancer. The restoration of NXTAR could serve as a new therapeutic modality for patients who have acquired resistance to second-generation AR antagonists.

Abstract

Androgen receptor (AR) signaling continues to play a dominant role in all stages of prostate cancer (PC), including castration-resistant prostate cancers (CRPC) that have developed resistance to second-generation AR antagonists such as enzalutamide. Described herein is the identification of a long non-coding RNA (lncRNA), NXTAR (LOC105373241), that is located convergent with the AR gene and is repressed in human prostate tumors and cell lines. NXTAR bound upstream of the AR promoter and promoted EZH2 recruitment, causing significant loss of AR (and AR-V7) expression. Paradoxically, AR bound the NXTAR promoter, and inhibition of AR by the ACK1/TNK2 small molecule inhibitor (R)-9b excluded AR from the NXTAR promoter. The histone acetyltransferase GCN5 bound and deposited H3K14 acetylation marks, enhancing NXTAR expression. Application of an oligonucleotide derived from NXTAR exon 5 (NXTARN5) suppressed AR/AR-V7 expression and prostate cancer cell proliferation, indicating the translational relevance of the negative regulation of AR. In addition, pharmacological restoration of NXTAR using (R)-9b abrogated enzalutamide-resistant prostate xenograft tumor growth. Overall, this study uncovers a positive feedback loop, wherein NXTAR acts as a novel prostate tumor-suppressing lncRNA by inhibiting AR/AR-V7 expression, which in turn upregulates NXTAR levels, compromising enzalutamide-resistant prostate cancer. The restoration of NXTAR could serve as a new therapeutic modality for patients who have acquired resistance to second-generation AR antagonists.

Significance

Described herein is the discovery of NXTAR as a tumor-suppressive lncRNA that can epigenetically downregulate AR/AR-V7 expression and provides a therapeutic strategy to reinstate NXTAR expression for treating recurrent CRPC.

Introduction

Prostate cancer (PC) is the second most reported cancer in American men. The limited efficacy of androgen deprivation therapies often results in progression of the disease to lethal castration-resistant prostate cancer (CRPC) in 1 to 2 years, with reversion of androgen receptor (AR) activity. To combat CRPCs, abiraterone, an androgen biosynthesis inhibitor, and enzalutamide, a drug that inhibits AR nuclear translocation, have been widely used; however, the overall disease-free survival for these two AR antagonists as single agents has been modest and their combination has provided little advantage. Robust amplification of the AR enhancer region in almost 81% of enzalutamide-treated patients reinforces the notion that AR signaling is the epicenter of drug resistance. The bypassing of AR signaling by increased expression of glucocorticoid receptor (GR) is thought to be one of the early mechanisms of enzalutamide resistance. A pluripotency transcription factor, SOX2, was later shown to be required for the lineage plasticity and enzalutamide resistance through the loss of TP53 and RB1. AR regulating its own expression by epigenetic modification (phospho-Tyr88-H4) of its enhancer in an enzalutamide-rich environment has emerged as another mechanism to maintain high AR levels and thus confer resistance. In addition, many CRPC patients develop resistance by expressing an AR splice variant called AR-V7 that lacks the ligand-binding domain, nullifying the effects of these two AR antagonists. Collectively, these data have firmly established that AR is not only important in the pre-CRPC scenario, but also retains a dominant role in the post-CRPC stage, including in the drug-resistant state.

The identification of a large number of noncoding RNAs (ncRNAs) has firmly established the much-awaited paradigm that the human genome is pervasively transcribed, regardless of the protein coding abilities of the resultant RNAs, with ncRNAs comprising almost 90% of the transcribed genome. Long noncoding RNAs (lncRNAs), typically >200 nt long, with mostly no evident open reading frames (ORFs) but sometimes with a polyadenylated tail, form a large portion of these ncRNAs. The surge in studying these lncRNAs has revealed their important contribution in myriad biological processes, including cell proliferation, drug resistance, metabolism, apoptosis, and senescence. LncRNAs often participate in these processes by orchestrating enzymatic protein regulation or degradation or by fine-tuning different chromatin states, indicating that deregulation of certain lncRNAs could lead to the development of a disease.

Because AR activity is paramount to all stages of PC, the importance of PC-specific or PC-regulating lncRNAs has long been speculated. Studies have revealed that successive binding of AR to two overexpressed lncRNAs in PC, PRNCR1 and PCGEM1, enhances its binding to androgen response elements (AREs) so as to induce AR-mediated gene expression in androgen-dependent or CRPC tumors. ARLNC1 (AR-regulated long non-coding RNA 1) was not only induced by the AR protein, but it also stabilized the AR transcript via RNA-RNA interaction. Overall, several studies have revealed the significance of lncRNA in AR signaling; however, direct negative regulation of AR and AR-V7 transcription by lncRNA has not yet been reported. Described herein is the discovery of a novel tumor-suppressor lncRNA, NXTAR, that not only suppressed AR and AR-V7 transcription, but also when NXTAR expression was reinstated, it inhibited the proliferation of enzalutamide-resistant PC cells and tumor development in prostate models. Herein is presented key data to demonstrate the importance of the NXTAR lncRNA and its potential therapeutic utility using a therapeutic oligonucleotide derived from this lncRNA.

Materials and Methods

Cell Lines, Plasmids, Retroviral Constructs, and siRNAs

RWPE-1 (normal human prostate cell line; CRL-11609, RRID:CVCL_3791), 22Rv1 (CRL-2505; RRID: CVCL_1045), LNCaP (CRL-1740, RRID:CVCL_1379), VCaP (CRL-2876; RRID:CVCL_2235), and PC3 (CRL-1435; RRID:CVCL_0035) cells were obtained from the American Type Culture Collection. LAPC4 and C4-2B cells were grown as described earlier (see e.g., Mahajan et al. (2017) Cancer Cell). Cells were grown in 5% charcoal-stripped FBS (Gibco, Cat #12676029) containing medium (CSM), mimicking androgen deprivation, or serum-free medium (SFM) for experimental purposes. All the cell lines were routinely tested for *Mycoplasma* (ATCC, Cat #30-1012K). Small interfering (si)RNAs for AR and ACK1 are as described previously (see e.g., Mahajan et al. (2017) Cancer Cell). NCOR1 siRNA was purchased from Horizon. pBABE-puro retroviral expression plasmids were used for NXTAR expression.

Human Subjects

Patients provided written informed consent and the study was conducted under Washington University in St. Louis institutional review board approved genitourinary banking protocol (HRPO #:201411135). Human prostate tumor and adjacent normal samples were obtained from the written consented prostate cancer patients following radical prostatectomy at the Washington University School of Medicine in St. Louis, Urologic surgery. The specimens were de-identified before processing in the laboratory. The normal (far from the tumor site) and tumor (center core of cancerous lesion) tissues were dissected by a board-certified genitourinary pathologist based on MRI imaging and pathology reports of the biopsies from each patient. About 2 mm of the collected tissue was H&E stained and reviewed again by a pathologist, who assigned a Gleason score. All the tumor samples had Gleason score of 7-9. The specimens were washed in PBS and RNA was prepared (Qiagen).

RNA Pull-Down Assay

A set of 5 DNA oligonucleotide probes complementary to NXTAR RNA was synthesized, with biotin labels at their 3' end (IDT). Nonspecific oligonucleotide recognizing lacZ RNA was synthesized as controls. The sequences are shown in TABLE 1.

TABLE 1

Oligonucleotide sequences.

| | |
|---|---|
| **NXTAR-derived Oligo sequence** | |
| NXTAR-N5 (SEQ ID NO: 1) | A*T*T*ATTATTTTAAATTTACAGA AGGGGAAACTAAGAATTATAGACAT GAAGTGACTC*A*C*C |
| Globin (SEQ ID NO: 13) | CCTCTTACCTCAGTTACAATTTATA |
| Biotin-NXTARN5 (SEQ ID NO: 14) | Biotin-A*T*T*ATTATTTTAAAT TTACAGAAGGGGAAACTAAGAATTA TAGACATGAAGTGACTC*A*C*C |
| Biotin-Globin (SEQ ID NO: 15) | Biotin-CCTCTTACCTCAGTTACA ATTTATA |
| **NXTAR Pull Down Oligos** | |
| NXTAR Forward Primer (Primer IV) (SEQ ID NO: 16) | GCAGGTGGTGGTGTCCAATC |
| NXTAR Reverse Primer (Primer IV) (SEQ ID NO: 17) | CCGCAAGAGGGCAGATACA |
| 18S Forward Primer (SEQ ID NO: 18) | GGCCCTGTAATTGGAATGAGTC |
| 18S Reverse Primer (SEQ ID NO: 19) | CCAAGATCCAACTACGAGCTT |
| AR Forward Primer (SEQ ID NO: 20) | ATGGTGAGCAGAGTGCCCTATC |
| AR Reverse Primer (SEQ ID NO: 21) | ATGGTCCCTGGCAGTCTCCAAA |
| AR-V7 Forward Primer (SEQ ID NO: 22) | CAGGGATGACTCTGGGAGAA |
| AR-V7 Reverse Primer (SEQ ID NO: 23) | GCCCTCTAGAGCCCTCATTT |
| KLK3 Forward Primer (SEQ ID NO: 24) | CGCAAGTTCACCCTCAGAAGGT |
| KLK3 Reverse Primer (SEQ ID NO: 25) | GACGTGATACCTTGAAGCACACC |
| TMPRSS2 Forward Primer (SEQ ID NO: 26) | CAGGAGTGTACGGGAATGTGATGGT |
| TMPRSS2 Reverse Primer (SEQ ID NO: 27) | GATTAGCCGTCTGCCCTCATTTGT |
| ACK1 Forward Primer (SEQ ID NO: 28) | ACTTTGGGCTGATGCGAGCACT |
| ACK1 Reverse Primer (SEQ ID NO: 29) | AAGGTGCGTGTCTTCAGGCTCT |
| Actin Forward Primer (SEQ ID NO: 30) | CACCATTGGCAATGAGCGGTTC |
| Actin Reverse Primer (SEQ ID NO: 31) | AGGTCTTTGCGGATGTCCACGT |
| **ChIP Primers** | |
| AR TSS -0.7 pF1 (SEQ ID NO: 32) | GGGTGATTTTGCCTTTGAGA |
| AR TSS -0.7 pR1 (SEQ ID NO: 33) | CTGCCTTTCTTCCTGTCTGG |
| AR TSS +0.5 pF1 (SEQ ID NO: 34) | GCCCGAGTTTGCAGAGAG |
| AR TSS +0.5 pR1 (SEQ ID NO: 35) | AGTCGCCTGGCTCCTAA |

TABLE 1-continued

| Oligonucleotide sequences. | |
|---|---|
| AR TSS +1.4 pF1 (SEQ ID NO: 36) | CACAGGCTACCTGGTCCT |
| AR TSS +1.4 pR1 (SEQ ID NO: 37) | TCTGGGACGCAACCTCT |
| AR TSS +2.6 pF1 (SEQ ID NO: 38) | TTCTGGGTCACCCTCAGC |
| AR TSS +2.6 pR1 (SEQ ID NO: 39) | CACCACCACCACACGGT |
| AR TSS +3.3 pF1 (SEQ ID NO: 40) | GTAGTTGCTTGGGTCGGTTT |
| AR TSS +3.3 pR1 (SEQ ID NO: 41) | CTGATGCAAACCTGAAGTAGGG |
| PPr3 Forward primer (SEQ ID NO: 42) | ACACCAGGGAATTAGCAGGC |
| PPr3 Reverse primer (SEQ ID NO: 43) | GCCTTCCTTCTGCAGCAATC |
| PPr4 Forward primer (SEQ ID NO: 44) | CCTCTCTGGTGTCATATCGCTT |
| PPr4 Reverse primer (SEQ ID NO: 45) | GTCCTTGGTGCTAGATCTGTAAGG |
| ChIRP Primers | |
| AR Up 1.1 FP (SEQ ID NO: 46) | GTGAGGATTCAGTTCATTCACG |
| AR Up 1.1 RP (SEQ ID NO: 47) | GCCATTCTTCTAAGAGCCTCACA |
| NXTAR Enhancer FP (SEQ ID NO: 48) | GGCATGGGCCTCACTAGAAT |
| NXTAR Enhancer RP (SEQ ID NO: 49) | AGCCAAGCTCAGAATGTGGG |
| IRF8 Binding Site FP (SEQ ID NO: 50) | ACCTTTCCTCCAAGCTCCAC |
| IRF8 Binding Site RP (SEQ ID NO: 51) | TTGCTGCAGAATCTAAAGTCCT |
| NXTAR Pull Down Oligos | |
| NXTAR -1 (SEQ ID NO: 52) | 5'-caaatgccagttcttctgtg-biotin |
| NXTAR -2 (SEQ ID NO: 53) | 5'-caggaaatcccaaggttgta-biotin |
| NXTAR -3 (SEQ ID NO: 54) | 5'-aattccatatggagcctttt-biotin |
| NXTAR -4 (SEQ ID NO: 55) | 5'-actatccaactcagaggtga-biotin |
| NXTAR -5 (SEQ ID NO: 56) | 5'-gggattttggcttcaagttt-biotin |
| lacZ (SEQ ID NO: 57) | 5'-atagagattcgggatttcgg-biotin |

The biotinylated oligonucleotides were incubated with lysates (2 h), and the lysates were incubated with streptavidin magnetic beads overnight. Beads attached to RNAs were divided equally and processed for either RNA isolation or western blotting. For RNA isolation, beads were washed three times and then separated using proteinase K treatment. RNA was then isolated and purified, and DNA was digested in the process. The real-time quantitative RT-PCR was performed on isolated RNA to check the efficiency of pull-down of NXTAR RNA. The remaining beads were heated at 80° C. for 5 min in loading buffer, followed by western blotting. The blots were probed with EZH2 (CST, 5246S; RRID:AB_10694683) antibody and Actin (SCBT, sc-47778; RRID:AB_2714189) was used as the loading control.

Chromatin Isolation by RNA Purification (ChIRP) Assay and NXTAR-EZH2 Binding to AR Promoter Biotin-labeled NXTAR-N5 (complementary to the AR promoter) and globin oligos were synthesized (IDT) (see e.g., TABLE 1). ChIRP was performed using lysate from formaldehyde-fixed VCaP cells and oligos that were immobilized to streptavidin beads, as described earlier (see e.g., Chu and Chang (2016) *Methods Mol Bio*). The amount of the chromatin DNA was determined by real-time PCR. For detection of NXTAR-N5/EZH2 binding, biotin-labeled NXTAR-N5 oligo and control globin oligo were incubated with VCaP cell lysates and were subjected to chromatin pull-down, followed by immunoblotting with EZH2 antibodies.

NXTAR-N5 Transfection

NXTAR-N5 oligonucleotide was synthesized by IDT, and the oligonucleotide sequence is provided in TABLE 1 and FIG. 7C (* represents phosphorothioate bond modifications to avoid degradation by exonucleases). Equal numbers of VCaP and 22Rv1 cells were transfected with NXTAR-N5 or globin-derived oligonucleotide using X-tremeGENE360 (Sigma-Aldrich, Cat #08724121001), and the number of live cells was counted 96 h post-transfection using trypan blue exclusion method (Sigma, Cat #T8154). RNA was prepared from these cells, and qRT-PCR [SYBR PremixEx Taq II (Tli RNase H Plus)ROX, Clontech Takara, Cat #RR82LR] for AR and AR-V7 was performed as described earlier (see e.g., Mahajan et al. (2017) Cancer Cell).

Chromatin Immunoprecipitation

Chromatin immunoprecipitation (ChIP), quantitative RT-PCR, and ChIP-qPCR were performed as described earlier (see e.g., Mahajan et al. (2017) *Cancer Cell*; Mahajan et al. (2012) *J Biol Chem*; and Mahajan et al. (2012) *Nat Struct Mol Bio*). Briefly, cells were either transfected, infected or treated with various inhibitors (R)-9b; CPTH2 (Sigma, Cat #C9873)], fixed in formaldehyde, lysed and ChIP was performed with antibodies recognizing AR (SCBT, sc-7305; RRID:AB_626671), GCN5 (SCBT, SC-365321; RRID: AB_10846182), H3K14ac (CST, 7627S; RRID: AB_10839410), H3K27me3 (CST, 9733S; RRID:AB 2616029), NCOR1 (Bethyl Laboratories, Cat #A301-145A; RRID:AB_873085), EZH2 (CST, 5246S; RRID: AB_10694683), or IgG (Abcam, ab2410; RRID: AB_303052), immobilized on Protein A magnetic beads (Biorad, Cat #161-4013). The complexes were washed with ChIP buffers, eluted with elution buffer (Active Motif, Cat #53008), and subjected to reverse crosslinking, followed by RNase and proteinase K treatments. A part of soluble chromatin was processed separately at the same time and designated as input DNA. Treated ChIP DNA and input DNAs were purified using PCR-DNA purification columns (Qiagen, Cat #28106). The amount of immunoprecipitated DNA was determined by real-time PCR.

Quantitative RT-PCR

Cells were transfected, infected or treated [(R)-9b; EPZ6438, TargetMol, Cat #T1788] accordingly. RNA was used for cDNA preparation using High-Capacity cDNA Reverse Transcription Kit (Thermo Scientific Cat #4368814). Resulting cDNA was then analyzed by qPCR using an Applied Biosystems 7900 Real-Time PCR System (Thermo Scientific) and SYBR Green PCR Master Mix [SYBR PremixEx Taq II (Tli RNase H Plus) ROX, Clontech Takara, Cat #RR82LR] according to the manufacturers' instructions. Dissociation curves were generated for each plate to verify the integrity of the primers. The relative expression of RNAs was calculated using the comparative Ct or standard curve method. 18S rRNA or actin were used as internal controls. The primers used are shown in TABLE 1.

Xenograft Studies

All animal experiments were performed using the standards for humane care in accordance with the National Institutes of Health *Guide for the Care and Use of Laboratory Animals*. Mice breeding and colony maintenance were performed according to IACUC protocols approved by Washington University in St. Louis. 1.5×106 VCaP cells were suspended in 200 μL of PBS with 50% Matrigel (Corning, Cat #354428) and implanted subcutaneously into the dorsal flank of castrated 6-week-old male SCID mice (Charles River, Strain code: 236). Once the tumors reached approximately 100 $mm^3$, mice were randomized and injected subcutaneously with (R)-9b mesylate salt suspended in 6% Captisol (Cydex Pharmaceuticals). Tumor volumes were measured twice weekly using calipers. At the end of the study, all mice were humanely euthanized and tumors were extracted and weighed. To assess the role of NXTAR in tumor growth, 1.5×106 VCaP cells that were either infected with pBABE vector or NXTAR and selected with puromycin (Gibco, Cat #A1113803), implanted and growth of tumors was recorded. The personnel taking tumor volume measurement were blinded for the treatment groups.

Proliferation Assay

The 22Rv1, VCaP, or LNCaP cells were retrovirally infected with control or NXTAR vectors and selected in puromycin medium containing 5% charcoal-stripped serum. Equal numbers of selected cells were seeded in 6-well plates followed by treatment with either (R)-9b, enzalutamide (Selleck Chemicals, Cat #S1250), or abiraterone (Selleck Chemicals, Cat #52246), and the number of viable cells was counted by trypan blue exclusion assay.

Antibodies and Western Blot Analysis

Cells were harvested, lysed by sonication in receptor lysis buffer (see e.g., Mahajan et al. (2010) *PLoS One*) and 20-50 μg of protein lysates were fractionated by SDS-PAGE, and transferred onto a PVDF membrane (Immobilon, Cat #IPVH00010). After blocking in 5% nonfat dry milk (RPI, Cat #M17200) (or 3% BSA, Goldbio, Cat #A-420-500), membranes were incubated with the following monoclonal antibodies: AR (SCBT, Cat #sc-7305; RRID:AB 626671), pY276-AR (29), ACK1 (SCBT, sc-28336; RRID:AB 626629), pACK1 (Upstate, 09-142; RRID:AB 612088), EZH2, and Actin. The signals were visualized by using the enhanced chemiluminescence (ECL; Pierce, 32106) system.

6×His Tagged-EZH2 Purification 1 mg of lysate prepared from HEK293 cells transfected with 6λHis-tagged-EZH2 plasmid was incubated with Ni-NTA agarose beads (Qiagene) overnight at 4° C. Beads were washed three times using wash buffer (20 mM Tris/HCl, 200 mM NaCl, 5 mM imidazole; pH 7.5) and purified EZH2 was eluted using elution buffer (20 mM Tris/HCl, 200 mM NaCl, 200 mM imidazole; pH 7.5).

EZH2 Pull-Down Assay

LncRNA-Protein binding study was performed as described earlier (see e.g., Zhao, Wang, and Hu (2021) Methods Mol Bio). Briefly, 10 pmol Biotinylated NXTAR-N5 oligo or Biotinylated Globin oligos were diluted in 40 ul RNA structure buffer, heated at 90° C. for 2 min, immediately transferred onto ice for 2 min and then kept at RT for further 20 mins. 10 uM of purified EZH2 protein was added to these biotinylated oligos with 500 ul of NETN buffer and the tubes were placed at 4° C. for 2 hrs. Post washing with cold NETN buffer, streptavidin magnetic beads (60 ul) were added into prepared oligo-protein mix and incubated at 4° C. overnight. Beads were washed 3 times with NETN buffer, followed by western blot analysis. For NXTAR-EZH2 binding studies, 10 pmol biotinylated oligos complementary to NXTAR or lacZ oligos were incubated with 1 μM RNA prepared from NXTAR overexpressing VCaP cells in hybridization buffer (50 mM Tris-HCl pH 7.0, 750 mM NaCl, 1 mM EDTA, 1% SDS, 15% Formamide), along with pre-washed streptavidin magnetic beads at RT for 4 h. 10 uM of purified EZH2 protein was added and after incubation for 2 hrs magnetic beads were washed 3 times with NETN buffer, followed by western blot analysis.

Statistical Analysis

Data were summarized by descriptive statistics. Data between two groups were analyzed with unpaired Student's t-tests using Graphpad Prism (Graphpad Software Inc., RRID:SCR_002798). The qRT-PCR gene expression in tumor normalized to matched samples of a gene was tested against one (indicating equality to matched normal samples) by one sample Wilcoxon test. All tests were 2-sided and a p-value of 0.05 was considered significant.

Results

AR Negatively Regulates the Tumor-Suppressor lncRNA NXTAR

Figure 9A:
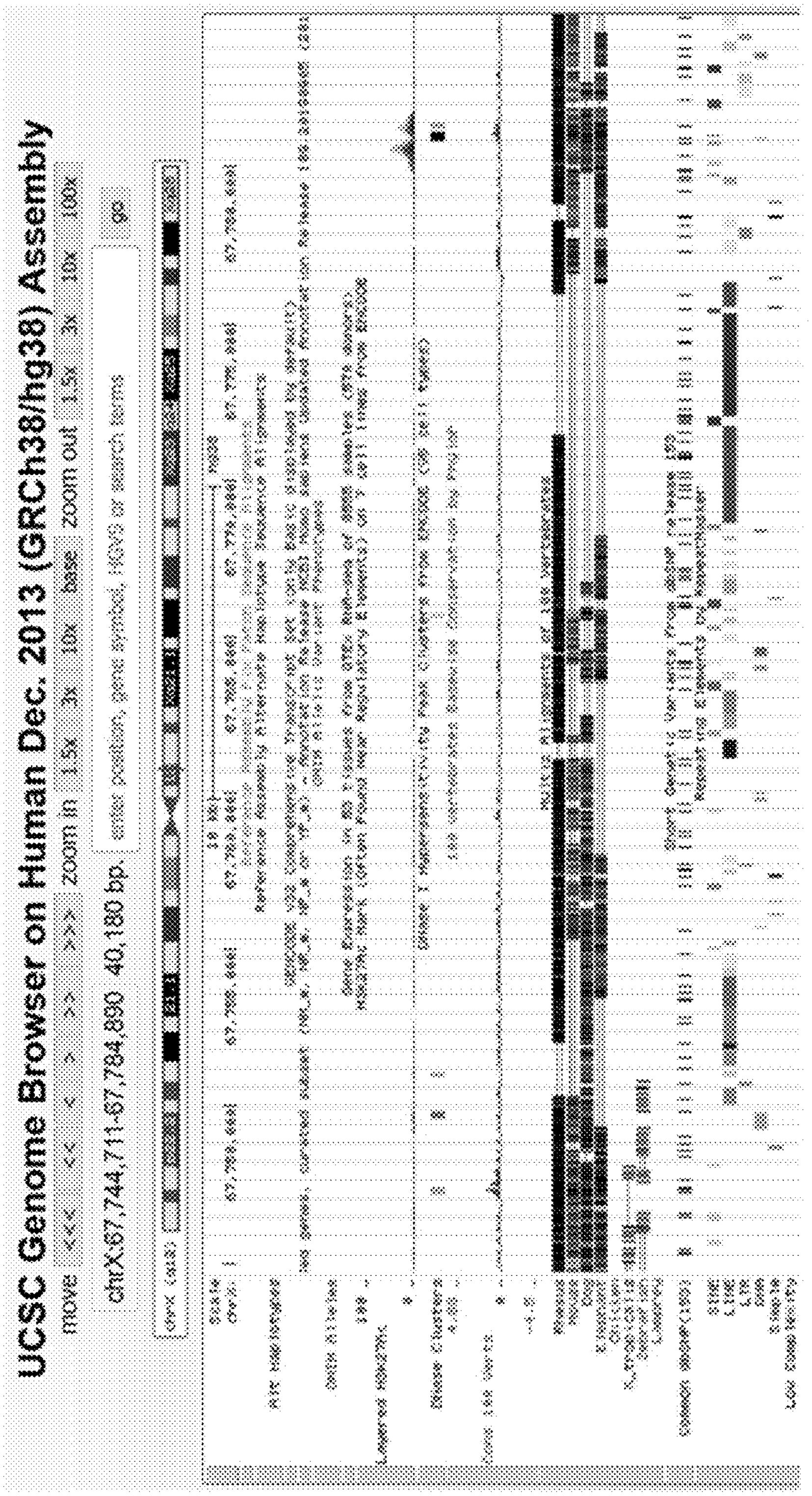
FIG. 9A-FIG. 9E. NXTAR gene shares homology with other mammals. (A) UCSC genome browser showing NXTAR gene sequences in other vertebrates as placed next to each other. (B, C) LNCaP and 22Rv1 cells were grown in CS-FBS containing media (lacking androgen) or media lacking total FBS (Growth factors+Androgen), followed by RNA isolation. qRT-PCR was performed using primers corresponding to NXTAR and 18S. Data are represented as mean±SEM as in (B, C). * $p<0.001$, $p<0.01$, *$p\leq0.05$, two-tailed Student's t-test. NS, not significant. (D) Agarose gel electrophoresis showing NXTAR expression in various cancer cell lines. (E) Expression of AR and NXTAR in TCGA PRAD cohort (N=43 patients with matched normal/tumor). P-values shown are paired Wilcoxon test.

Identified herein is a convergent lncRNA (LOC105373241) positioned next to the AR gene, which was named NXTAR (see e.g., FIG. 1A and FIG. 9A). The gene is 40,180 nt long (67,784,890 to 67,744,711 nt position), encoding a 1476-nt transcript (SEQ ID NO: 58) with 5 exons of 81, 94, 39, 103, and 1159 nt, respectively (see e.g., FIG. 1A). NXTAR exhibited overall homology with rhesus monkey, mouse, dog, and elephant sequences, but not with chicken, *Xenopus* frog, zebrafish, or lamprey (see e.g., FIG. 9A). Although exon 5 showed a small stretch of homologous sequence with *Xenopus*, NXTAR appears to be a mammalian lncRNA, and its regions of conservation with other mammals are shown in TABLE 2.

TABLE 2

Homologous regions in NXTAR lncRNAs of mammals.

| Species | Nucleotide position | Length of sequence | Percent Identity |
|---|---|---|---|
| *Macaca mulatta* | 614-1468 | 855 | 94.15 |
| *Macaca mulatta* | 316-464 | 149 | 94.63 |
| *Canis lupus* | 1274-1459 | 187 | 82.89 |
| *Canis lupus* | 345-461 | 117 | 82.91 |
| *Canis lupus* | 689-796 | 110 | 82.73 |
| *Canis lupus* | 948-1008 | 61 | 83.61 |
| *Loxodonta africana* | 1118-1252 | 137 | 86.13 |
| *Loxodonta africana* | 732-817 | 87 | 82.76 |
| *Mus musculus* | 1437-1456 | 20 | 100.0 |

Figure 9B:
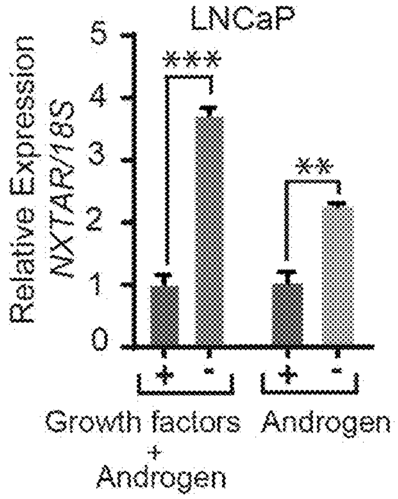
Figure 9C:
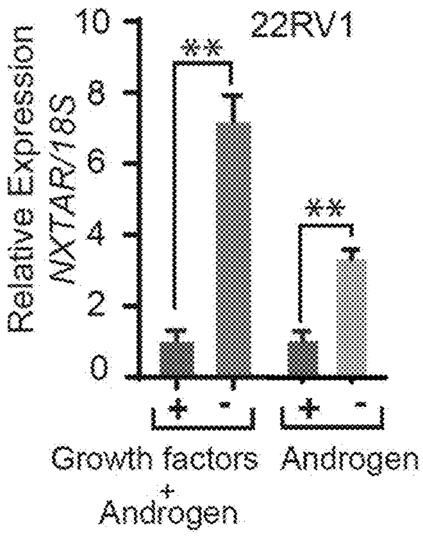

Given its genomic position and convergent location (see e.g., FIG. 1A), NXTAR may influence AR expression or might be affected by it (or both). PC cell lines were deprived of androgen, the ligand for AR, by growing them in CSM, followed by assessment of NXTAR RNA expression by qRT-PCR. LNCaP and 22Rv1 cells exhibited NXTAR upregulation upon androgen deprivation (see e.g., FIG. 9B and FIG. 9C). This increase in NXTAR was further enhanced upon removal of growth factors by growing cells in serum-free conditions (see e.g., FIG. 9B and FIG. 9C), suggesting that loss of AR activity could augment NXTAR levels.

Figure 10A:
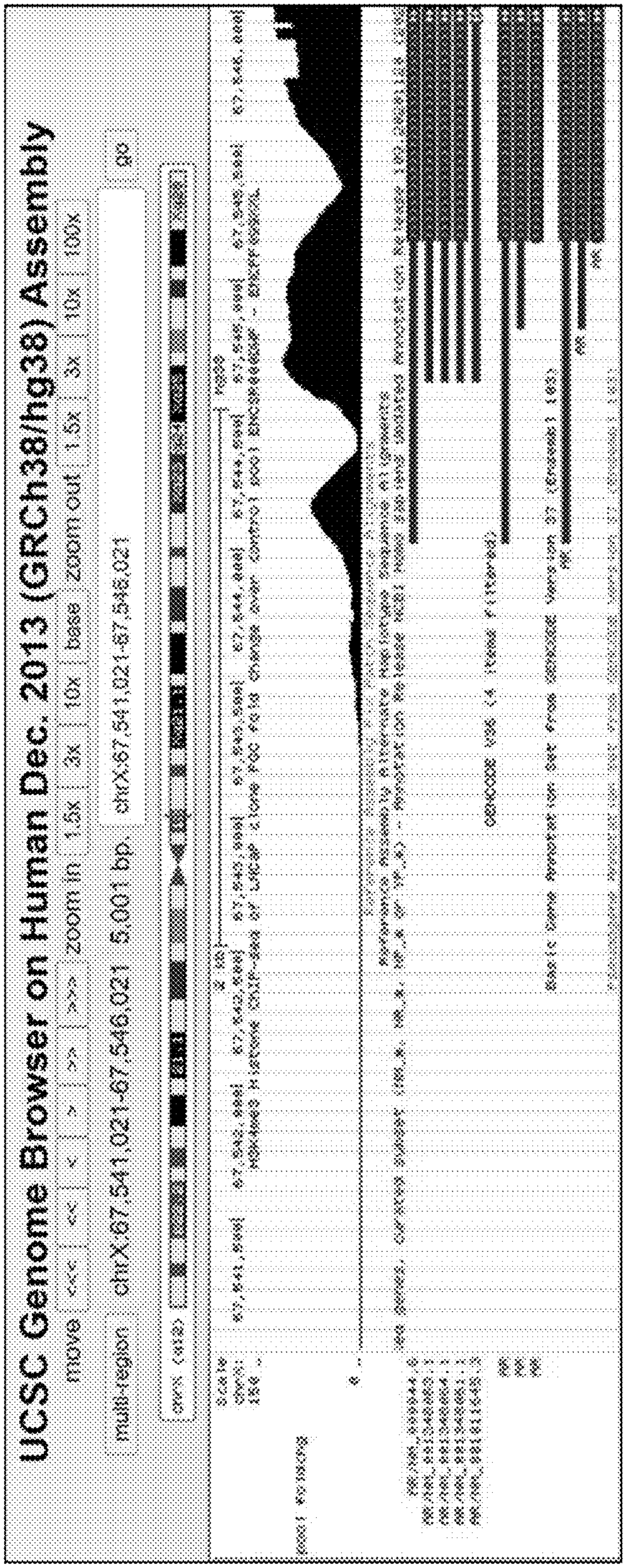
FIG. 10A-FIG. 10B. UCSC genome browser showing H3K4me3 Histone ChIP-seq in regions −3 kb to +2 kb downstream of (A) AR and (B) NXTAR gene in LNCaP cells.
Figure 10B:
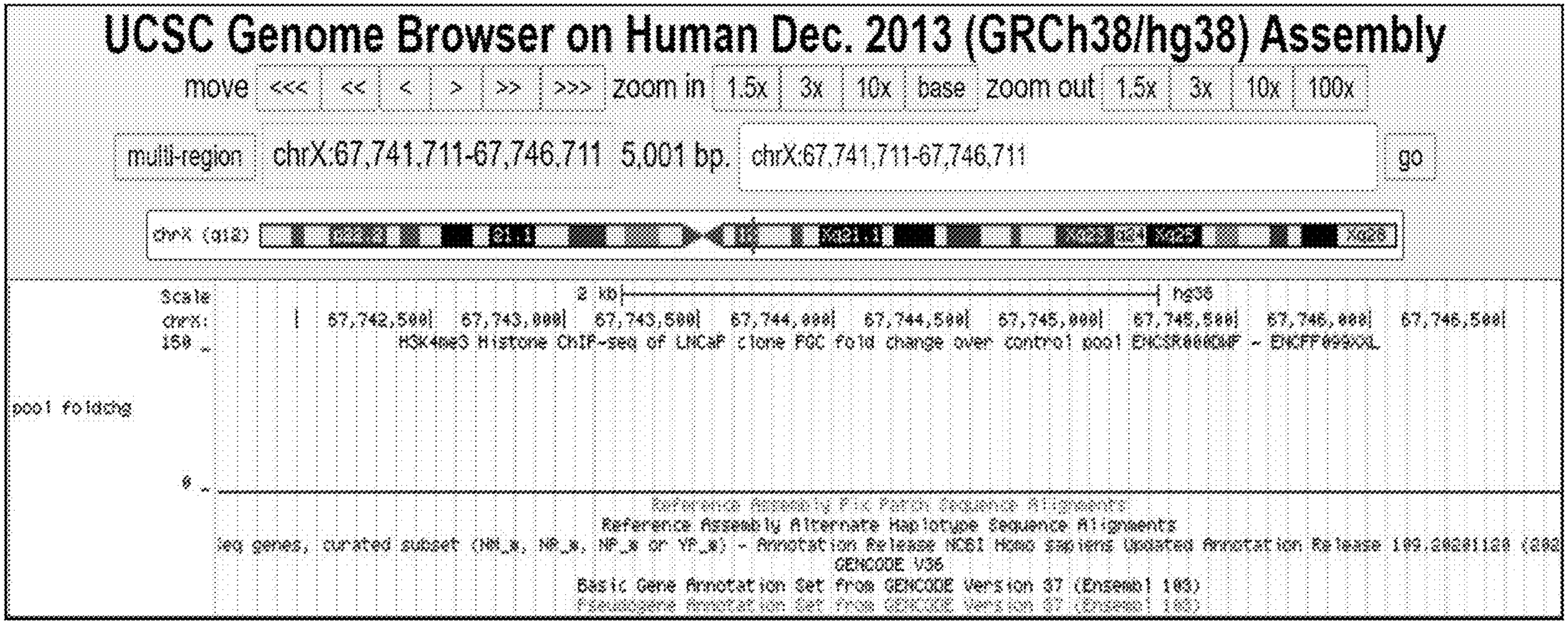

Methylation of the fourth amino acid residue from the N-terminus of histone H3, H3K4me3, is a histone modification associated with the promoters and transcription start sites (TSS) of actively transcribed genes. Although the AR promoter is enriched for H3K4me3 in most cancer samples, including CRPCs and AR-positive LNCaP cells (see e.g., FIG. 10A), H3K4me3 deposition on the NXTAR promoter was found to be lacking in LNCaP cells (GEO:GSM945240, see e.g., FIG. 10B). These data open the possibility of an inverse correlation between AR and NXTAR expression in PC.

Figure 1B:
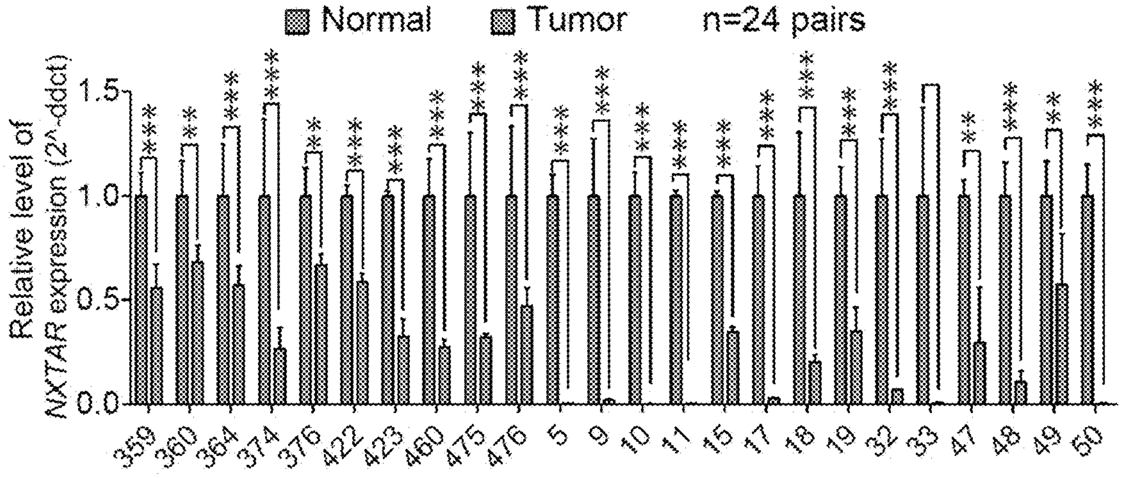
Figure 1C:
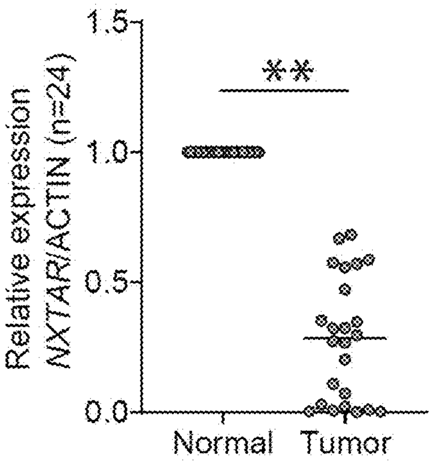
Figure 1D:
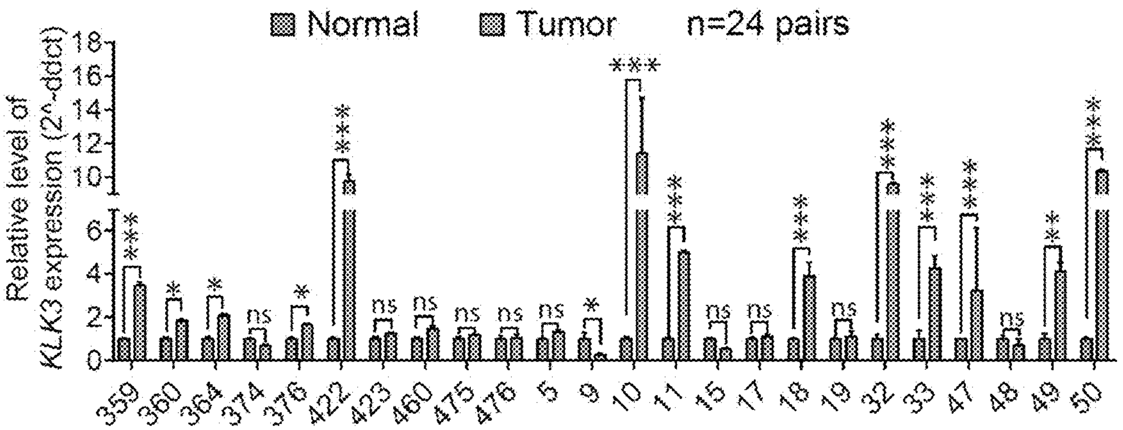
Figure 1E:
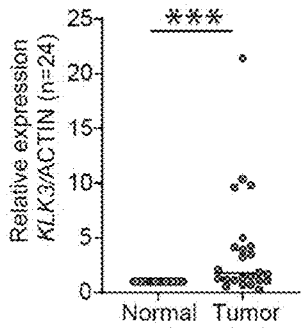
Figure 1F:
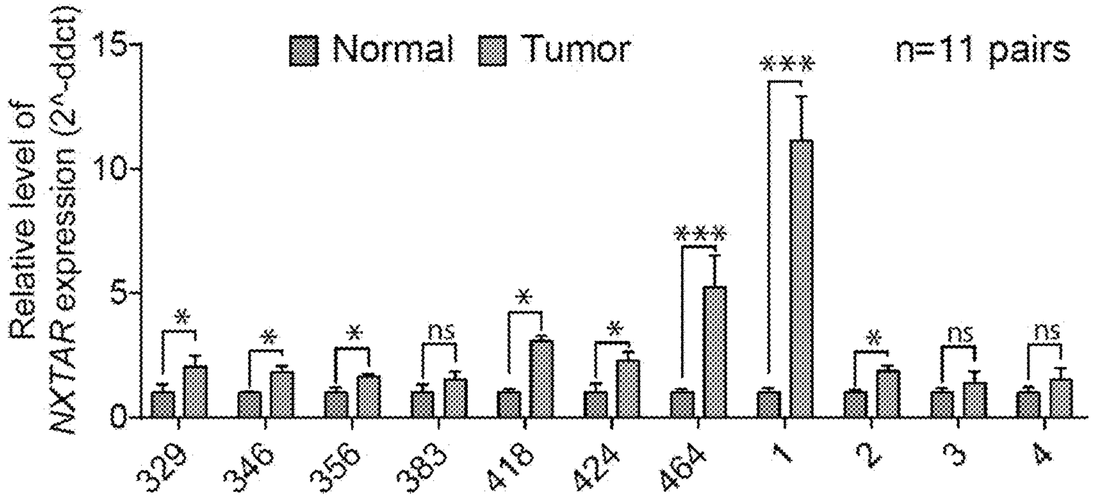
Figure 1G:
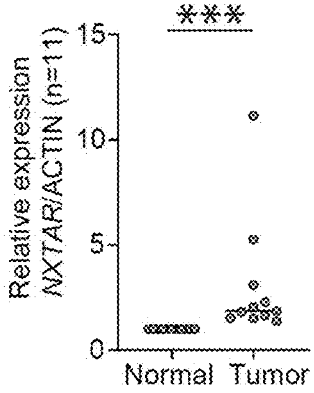
Figure 1H:
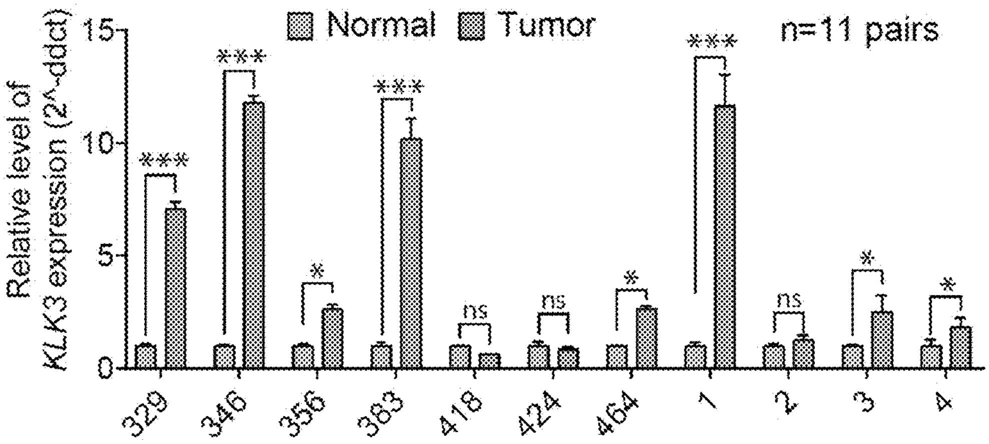
Figure 1I:
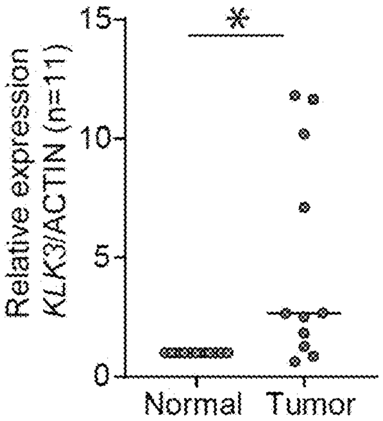
Figure 1J:
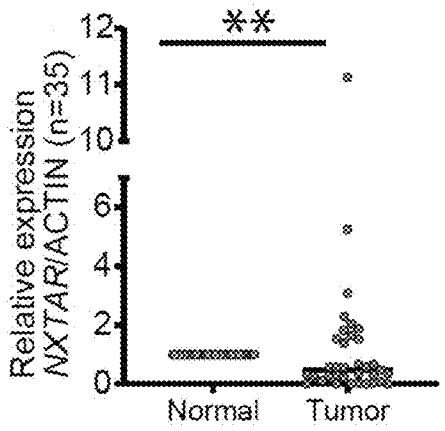
Figure 1K:
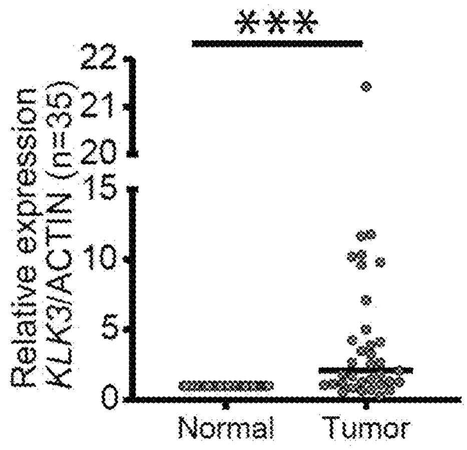
Figure 1L:
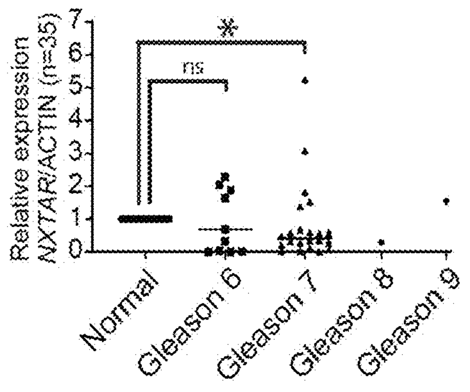

To test this hypothesis, a primer pair was designed that amplified the 177-bp region spanning exons IV and V of NXTAR and qRT-PCR of 35 human prostate cancer and paired normal prostate-derived RNAs was performed, which revealed 2 distinct scenarios. Type I: 24 out of 35 prostate cancer patients (68%) exhibited a significant decrease in NXTAR expression in tumors, compared to normal tissues (see e.g., FIG. 1B and FIG. 1C). Among these samples, the PSA/KLK3 expression was significantly up-regulated relative to normal (see e.g., FIG. 1D and FIG. 1E). Three out of these 10 patients (#376, 422 and 460) were treated with androgen deprivation therapy in past and were considered as CRPCs. Type II: In 11 out of 35 prostate cancer patients, NXTAR levels were either higher than normal or not significantly altered (see e.g., FIG. 1F and FIG. 1G). The KLK3 levels in these patients are also shown (see e.g., FIG. 1H and FIG. 1I). Data representing mean of relative NXTAR and KLK3 expression between normal and tumor samples are shown (see e.g., FIG. 1J and FIG. 1K). In addition, NXTAR levels in various grades of prostate cancer were also assessed, and it was observed that in low-grade cancer (Gleason grade 6) there was no statistically significant change, however, NXTAR levels were significantly down-regulated in Gleason grade 7 or medium-grade cancers (see e.g., FIG. 1L).

Figure 1M:
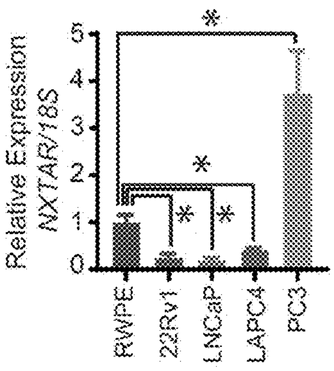
Figure 9D:
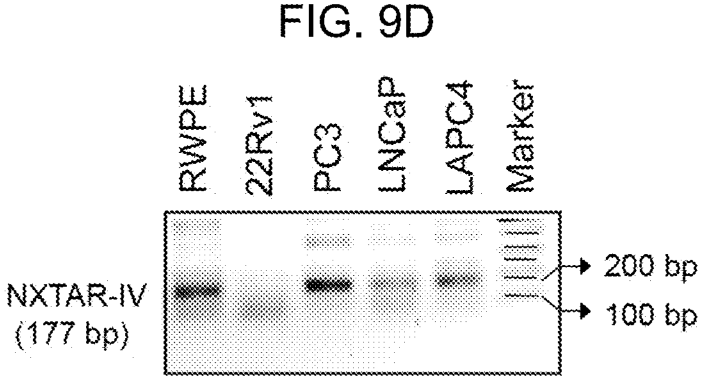

Furthermore, NXTAR expression was under-expressed in various AR-positive PC cell lines, including 22Rv1, LNCaP, and LAPC4. In contrast, "normal" prostate cells (RWPE) exhibited detectable NXTAR transcript levels (see e.g., FIG. 1M). The highest relative expression of NXTAR was observed in PC3 cells that have no detectable AR expression (see e.g., FIG. 1M). A semi-quantitative PCR using the same set of primers showed a pattern of NXTAR expression similar to that seen in qRT-PCR of different cell lines, with the highest expression in PC3 cells (see e.g., FIG. 9D).

Figure 2A:
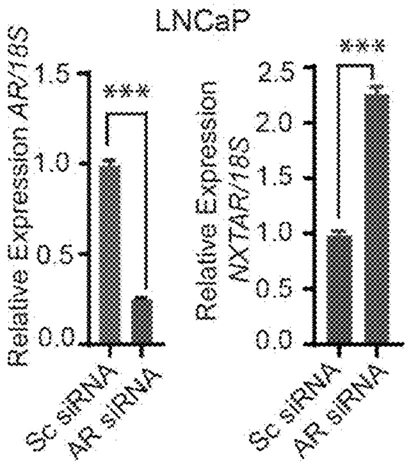
FIG. 2A-FIG. 2I. AR and ACK1 negatively regulate NXTAR expression in prostate cancer cell lines. (A-D) Androgen-deprived LNCaP, C4-2B, 22Rv1 and VCaP cells were transfected with scrambled (Sc) or AR siRNA. Total RNA was isolated, followed by qRT-PCR with AR, NXTAR and 18S rRNA primers. (E, F) Androgen-deprived (E) LNCaP and (F) 22Rv1 cells were treated with vehicle or (R)-9b (3.5 and 5 μM) for 48 hrs. Total RNA was isolated, followed by qRT-PCR with NXTAR and 18S rRNA primers. (G) qRT-PCR was performed to assess suppression of ACK1 expression in 22Rv1 cells upon transfection with two different sets of (set I and II) ACK1 siRNA. (H, I) Total RNA isolated from (H) LNCaP or (I) 22Rv1 cells in which ACK1 expression was downregulated using two different sets of siRNAs at the indicated time points and subjected to qRT-PCR. Data are represented as mean±SEM. * $p<0.001$,  $p<0.01$, *p two-tailed Student's t-test. NS, not significant.
Figure 2B:
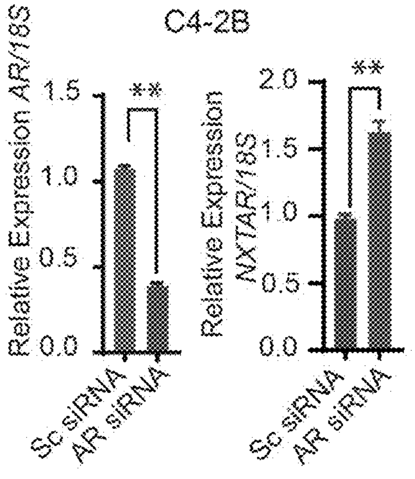
Figure 2C:
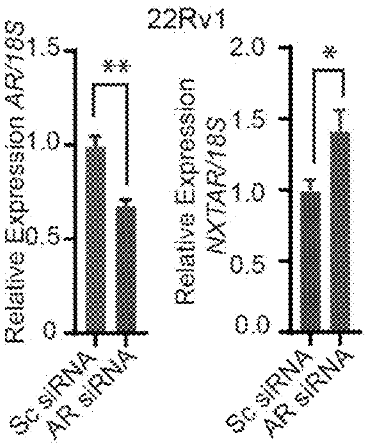
Figure 2D:
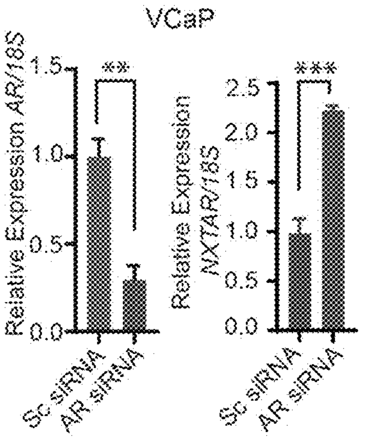
Figure 2E:
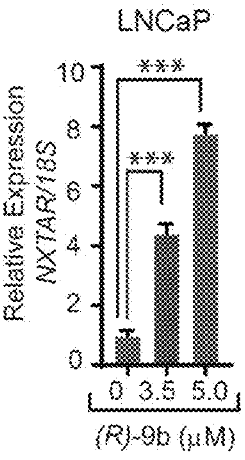
Figure 2F:
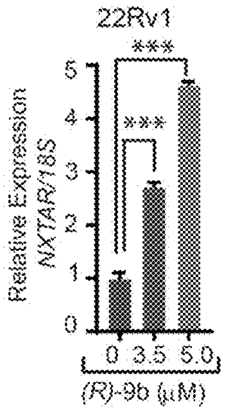
Figure 2G:
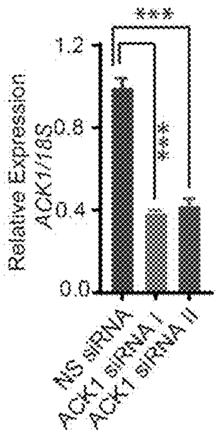
Figure 2H:
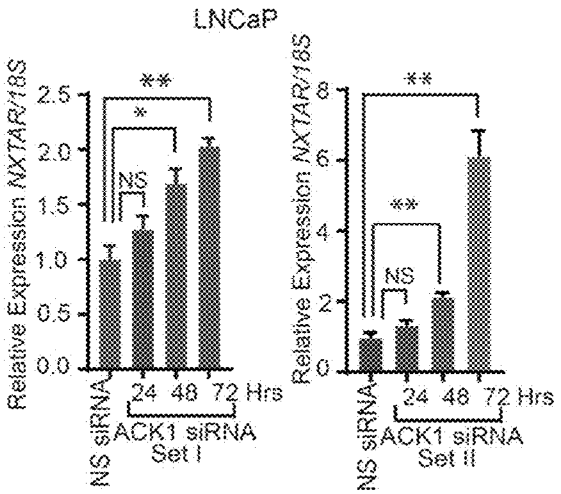
Figure 2I:
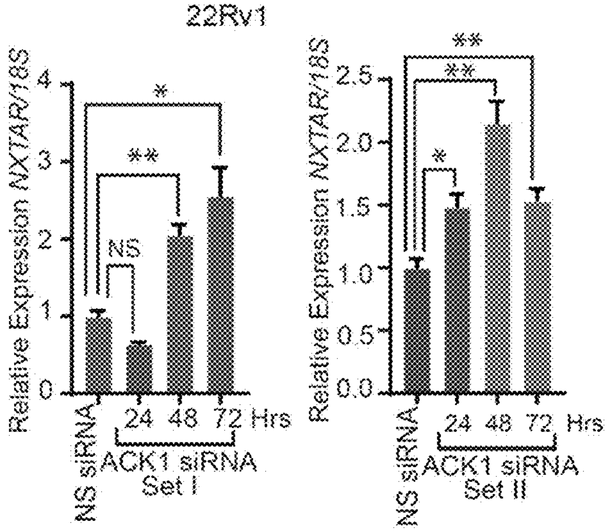
Figure 11A:
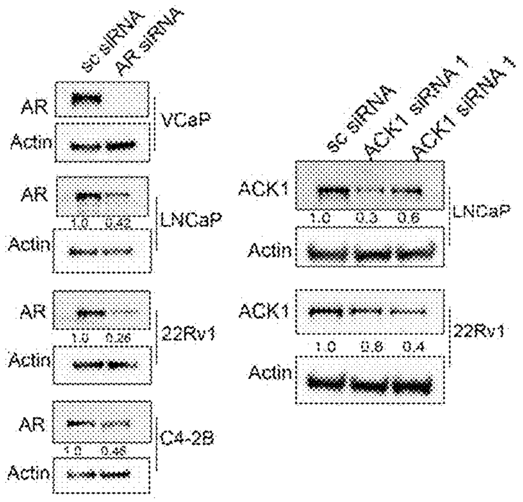
FIG. 11A-FIG. 11G. ACK1 inhibitor treatment compromises AR binding to NXTAR promoter and enables GCN5 recruitment. (A) Western blot representing AR and ACK1 silencing in prostate cancer cells. (B, C) Lysates from LNCaP cells treated with either vehicle, (R)-9b and (R)-9b with CPTH2 were subjected to ChIP using H3K14ac antibody followed by qPCR for Ppr3 (B) and Ppr4 (C) primers. (D, E) 22RV1 cells were treated with (R)-9b and the lysates were subjected to ChIP with GCN5 antibody, followed by qPCR for Ppr3 (D) and Ppr4 (E) sites. (F, G) 22RV1 cells were treated either vehicle or (R)-9b in the presence or absence of growth factors and the lysates were subjected to ChIP with AR antibody followed by qPCR for Ppr3 (F) and Ppr4 (G) sites. Data are represented as mean±SEM. *$p\leq0.05$;  $p<0.01$; *$p<0.001$, two-tailed Student's t-test.
Figure 11B:
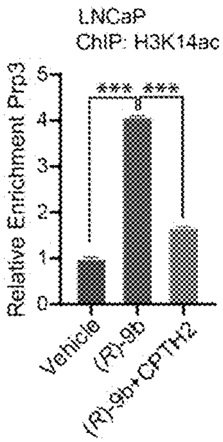
Figure 11C:
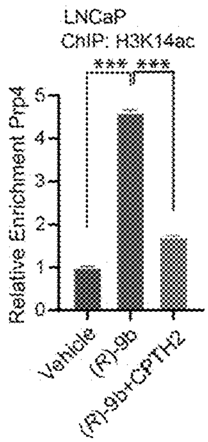
Figure 11D:
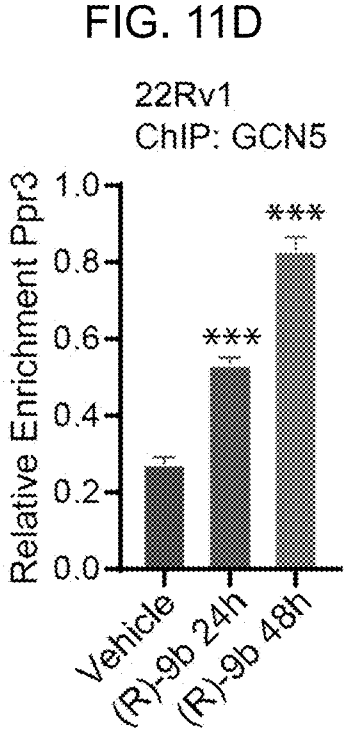
Figure 11E:
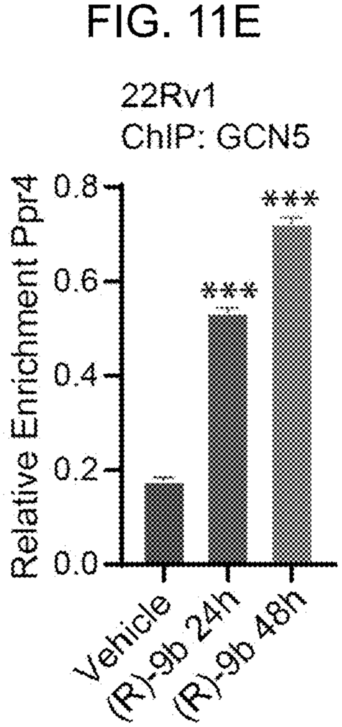
Figure 11F:
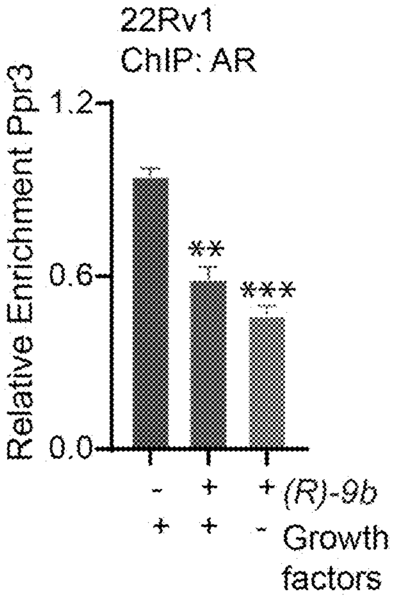
Figure 11G:
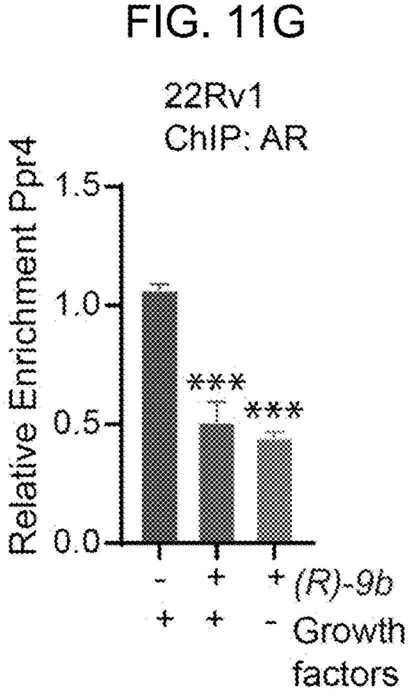
Figure 13A:
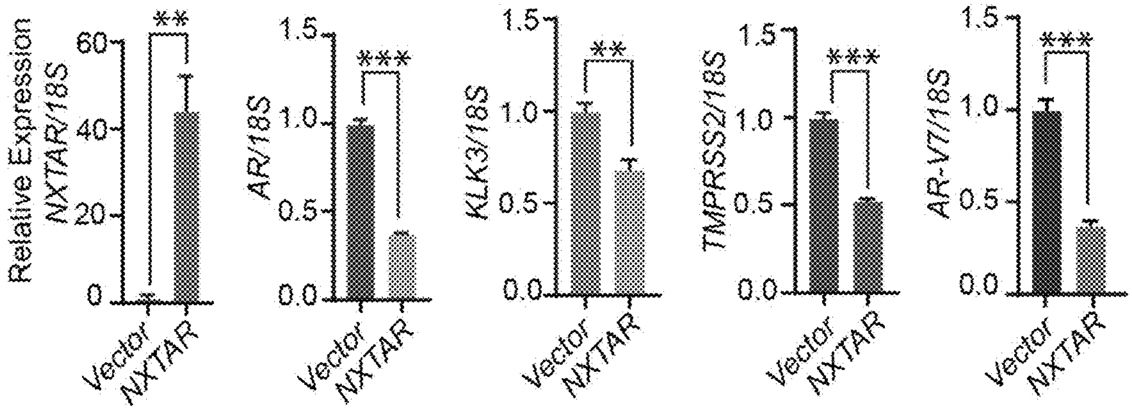
FIG. 13A-FIG. 13F. NXTAR suppresses AR levels and compromises AR signaling. (A, B) 22Rv1 (A) and VCaP (B) cells were infected with empty pBabe vector or NXTAR expressing constructs. RNA was isolated and qRT-PCR was performed to check NXTAR, AR, AR-V7, KLK3 and TMPRSS2 expression. Androgen-starved (C) LNCaP and (D) 22Rv1 cells were transfected with either pcDNA vector or NXTAR expressing plasmids for 24, 48 and 72 hrs followed by immunoblotting. Relative levels of AR expression are shown below top panels. (E, F) Androgen-deprived 22Rv1 cells were transfected with (E) pcDNA vector or (F) NXTAR expressing construct in increasing amounts (0.25-2 μg). After 48 hrs cells were harvested and processed for immunoblotting. Relative levels of AR expression are shown below top panels. (C, F) Representative immunoblots of two independent experiments are shown. Data (A, B) are represented as mean±SEM. *$p\leq0.05$;  $p<0.01$; *$p<0.001$, two-tailed Student's t-test. NS, not significant.
Figure 13B:
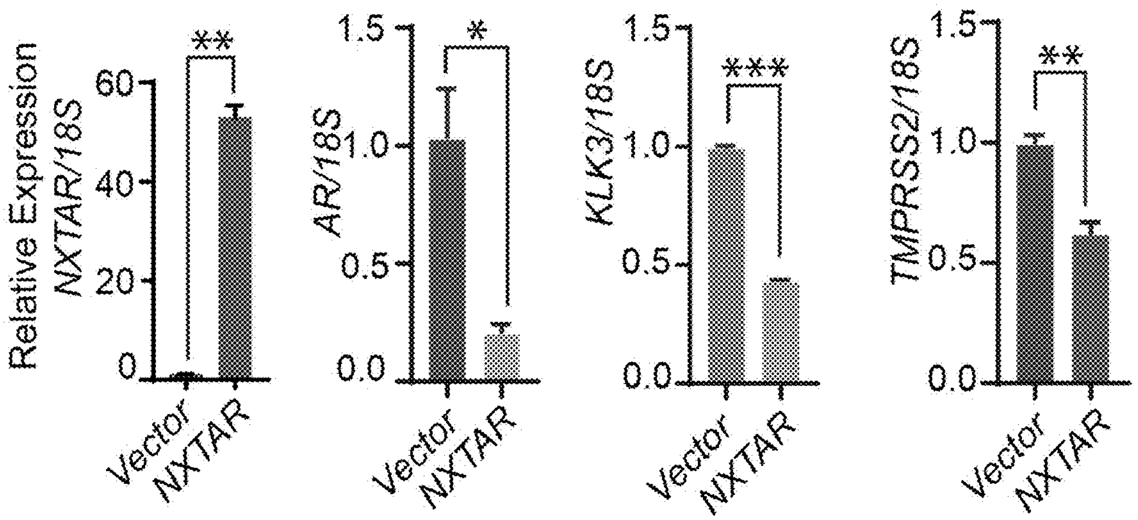
Figure 13C:
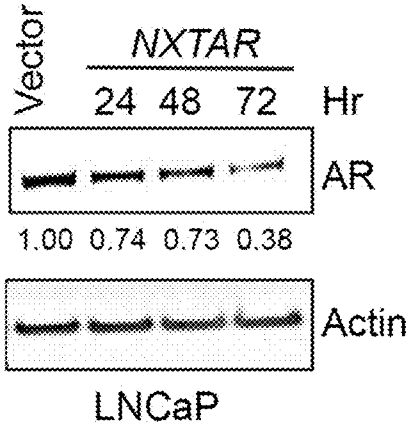
Figure 13D:
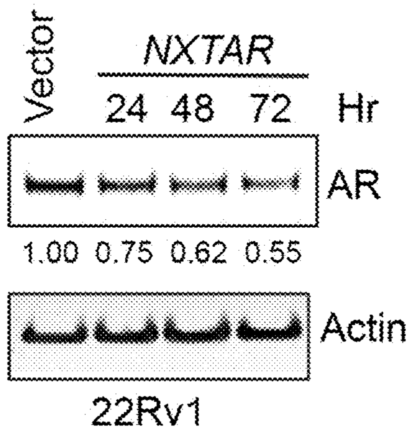
Figure 13E:
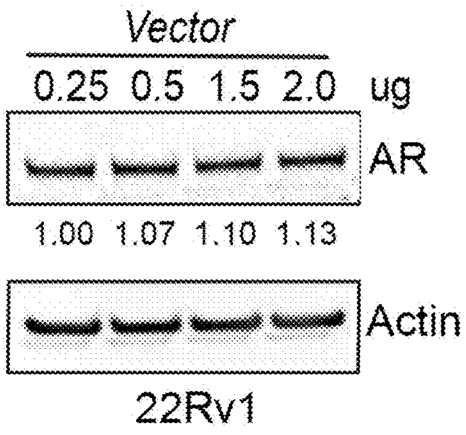
Figure 13F:
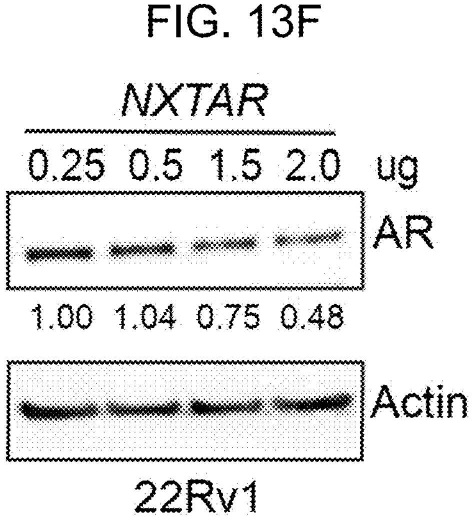
Figure 14A:
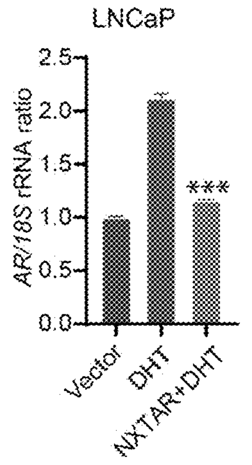
FIG. 14A-FIG. 14F. NXTAR lncRNA negatively modulates AR expression in PC cells. (A-D) LNCaP cells (A and B) and 22Rv1 cells (C and D) were retrovirally infected with pBabe vector or NXTAR and treated with DHT (10 nM) overnight, followed by qRT-PCR for AR (A, C) and KLK3 (B, D). 18S rRNA was used as loading control. (E) VCaP cells were retro-virally infected with either Vector, NXTAR or NXTAR with caACK1 (constitutively active) constructs and the mRNA was subjected to qRT-PCR for AR gene. (F) VCaP cells were retrovirally infected with either vector or NXTAR construct and treated for 96 h with either vehicle (DMSO) or 7 μM enzalutamide. The RNA was subjected to qRT-PCR for NXTAR and AR transcripts. 18S rRNA was used as loading control. Data are represented as mean±SEM. *$p\leq0.05$;  $p<0.01$; *$p<0.001$, two-tailed Student's t-test.
Figure 14B:
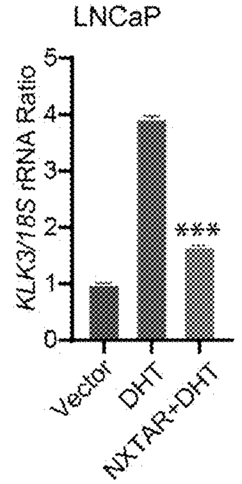
Figure 14C:
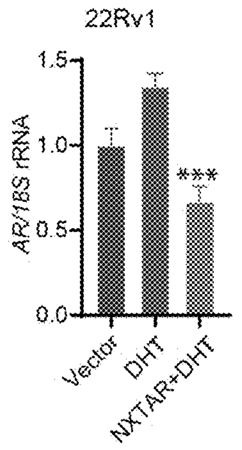
Figure 14D:
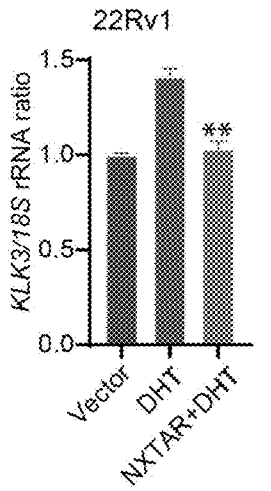
Figure 14E:
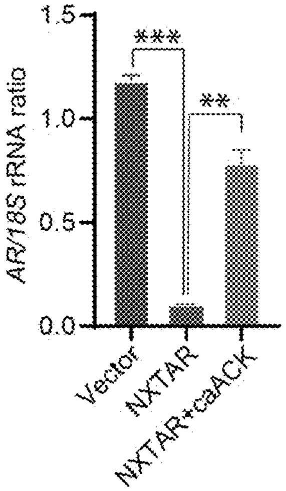
Figure 14F:
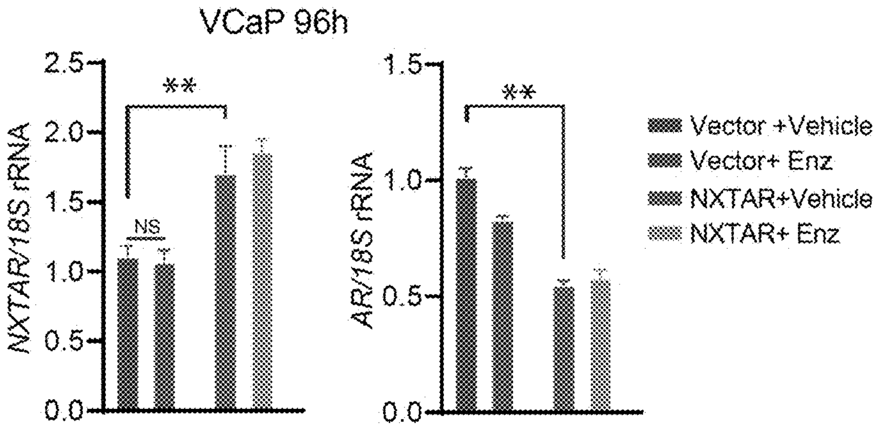
Figure 15A:
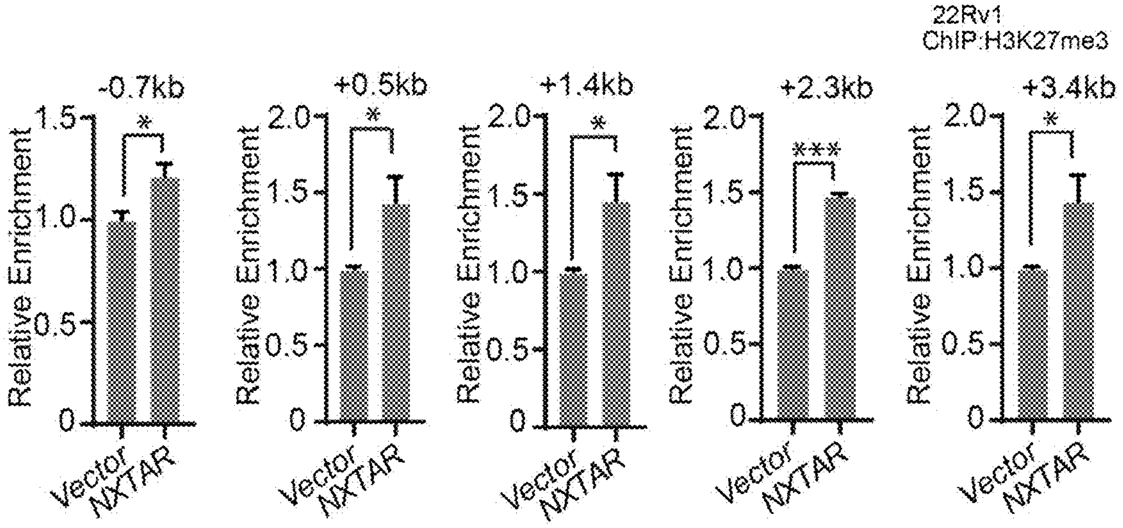
FIG. 15A-FIG. 15I. NXTAR overexpression and (R)-9b treatment enhances EZH2 recruitment and H3K27me3 marks on AR promoter site. (A) 22Rv1 cells were infected with either pBabe control vector or NXTAR expressing constructs and grown in androgen-free medium for 48 hrs. ChIP was performed using H3K27me3 antibody or IgG (see e.g., FIG. 17G-FIG. 17K and FIG. 17L-FIG. 17O), followed by qPCR with using primers spanning regions upstream and downstream of AR TSS (−0.7 kb to +3.4 kb) as shown in FIG. 5A. (B-E) VCaP cells were retro-virally infected as described above. ChIP was performed using EZH2 (B) and (C) H3K27me3 antibody, followed by qPCR for −0.7 kb downstream of AR TSS. VCaP cells were treated with vehicle control or (R)-9b overnight in androgen-free media and ChIP was performed using (D) EZH2 and (E) H3K27me3 antibody, followed by qPCR for −0.7 kb downstream of AR TSS. (F-H) 22Rv1 cells overexpressing either vector or NXTAR constructs were treated with either vehicle or (R)-9b overnight followed by ChIP using EZH2 antibody and qPCR for AR TSS (−0.7 Kb, F; 0.5 Kb, G; 1.4 Kb, H). (I) Relative NXTAR enrichment by RNA pull-down in NXTAR overexpressing cells. lacZ is used as negative control. Data are represented as mean±SEM. *$p\leq0.05$; $p<0.01$, *$p<0.001$, two-tailed Student's t-test.
Figure 15B:
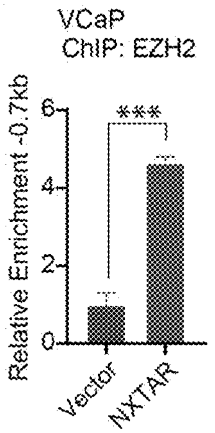
Figure 15C:
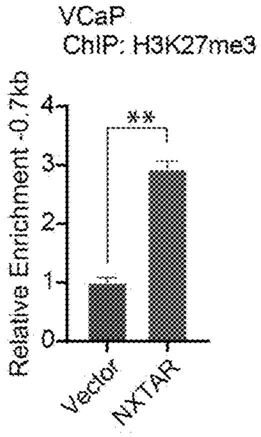
Figure 15D:
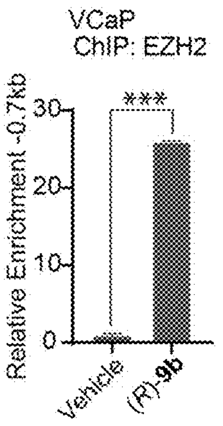
Figure 15E:
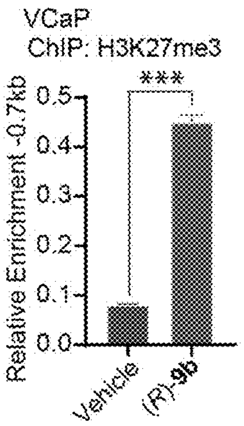
Figure 15F:
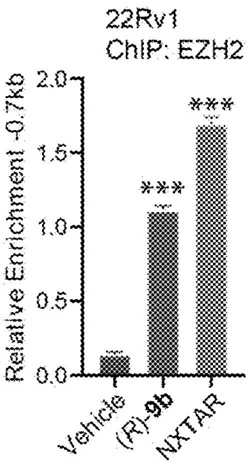
Figure 15G:
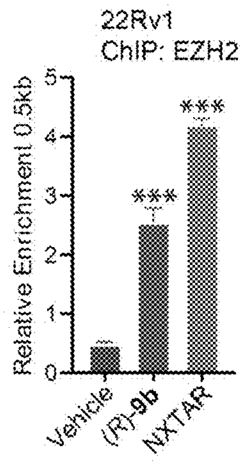
Figure 15H:
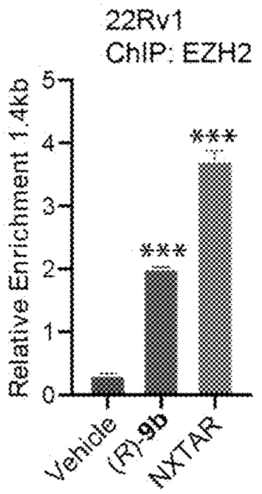
Figure 15I:
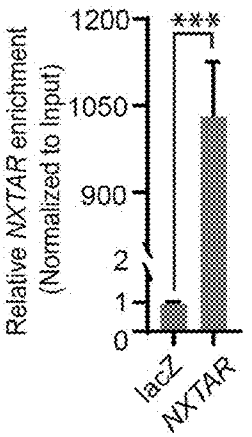
Figure 16A:
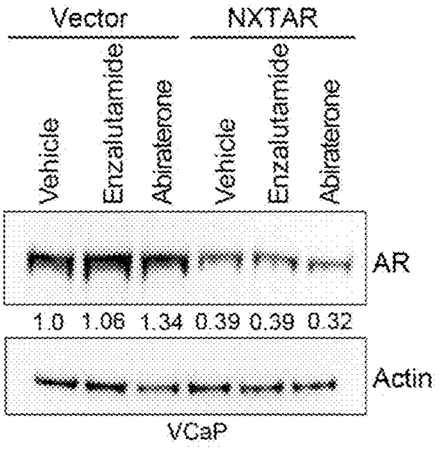
FIG. 16A-FIG. 16D. NXTAR restoration sensitizes prostate cancer cells. (A, B) VCaP (A) and 22Rv1 cells (B) were infected with either control vector or NXTAR expressing construct, subjected to puromycin selection, treated with either vehicle, enzalutamide or abiraterone for 96 h and the cell lysates were subjected to immunoblotting using AR antibody. (C, D) VCaP (C) and 22Rv1 cells (D) were infected with either control vector or NXTAR expressing construct, subjected to puromycin selection. Equal number of cells were seeded in androgen deprived media, and were either treated with vehicle (10% DMSO) or (R)-9b/enzalutamide for 9 days (VCaP) or 1-5 days (22Rv1). Cells were trypsinized and the number of viable cells were counted by trypan blue exclusion assay. Data are represented as mean±SEM. *$p\leq0.05$;  $p<0.01$; *$p<0.001$, two-tailed Student's t-test. NS, not significant.
Figure 16B:
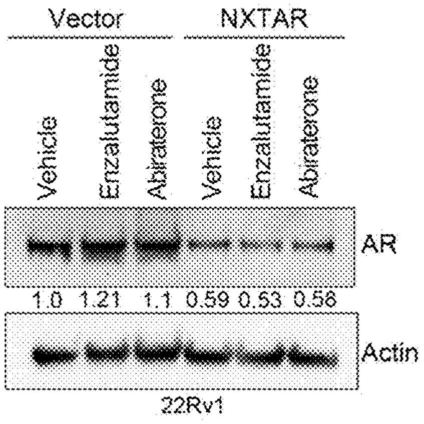
Figure 16C:
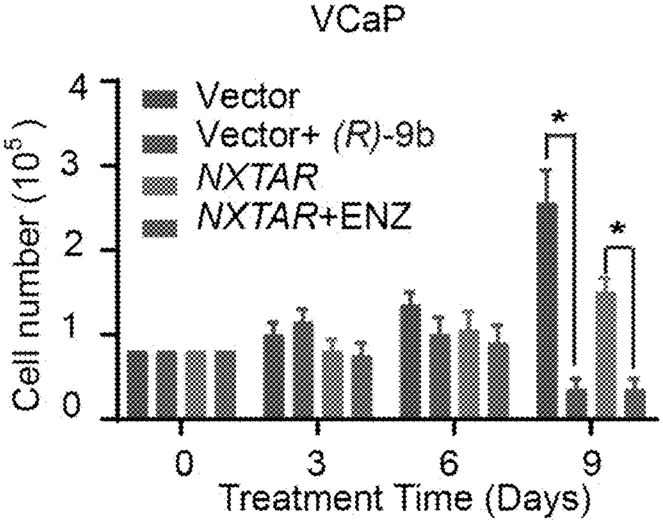
Figure 16D:
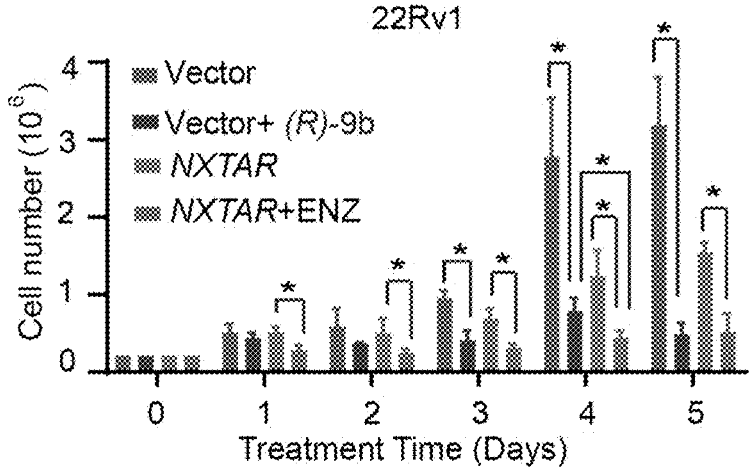
Figure 17A:
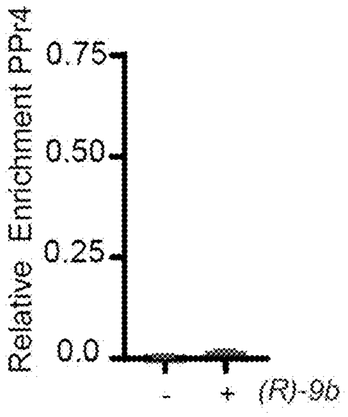
FIG. 17A-FIG. 17R. ChIP with IgG antibody was performed in respective samples as shown in FIG. 4A-FIG. 4M and FIG. 5A-FIG. 5E. Graphs represent ChIP qPCR with respective primer sets in cell lysates treated with different inhibitors or over-expression vectors and incubated with IgG antibody as mentioned in FIG. 4A-FIG. 4M and FIG. 5A-FIG. 5E. (A, B) 22Rv1 cells were treated with either vehicle or (R)-9b alone or in combination with CPTH2 and ChIP was performed using IgG antibodies. (C, D) LNCaP cells treated with (R)-9b alone or in combination with CPTH2 were subjected to ChIP using IgG. (E, F) LNCaP cells were treated with either (R)-9b alone or in combination with CPTH2 were harvested and processed for ChIP using antibody against IgG. (G-K and L-O) LNCaP cells were infected with either pBabe control vector or NXTAR expressing constructs and grown in androgen-free medium for 48 hrs. ChIP was performed using IgG. (P-R) LNCaP cells infected with pBabe or NXTAR expressing constructs and grown in androgen free medium for 48 hrs and ChIP was performed using IgG antibodies. Data are represented as mean±SEM. *$p\leq0.05$;  $p<0.01$; *$p<0.001$, two-tailed Student's t-test. NS, not significant.
Figure 17B:
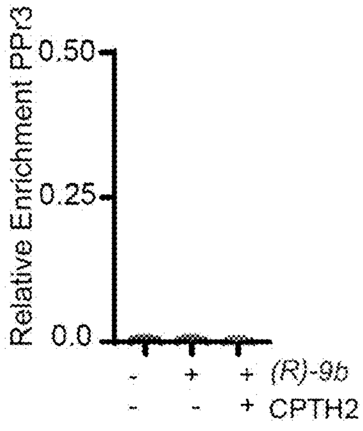
Figure 17C:
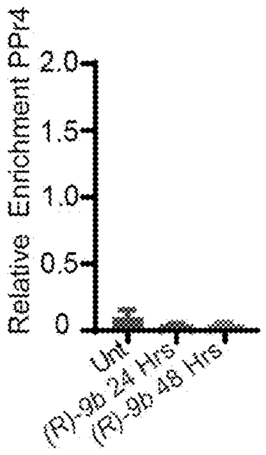
Figure 17D:
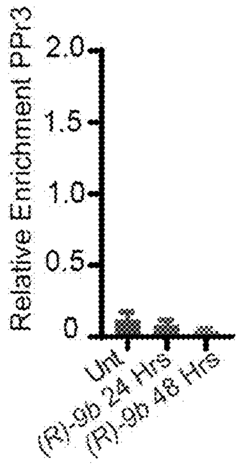
Figure 17E:
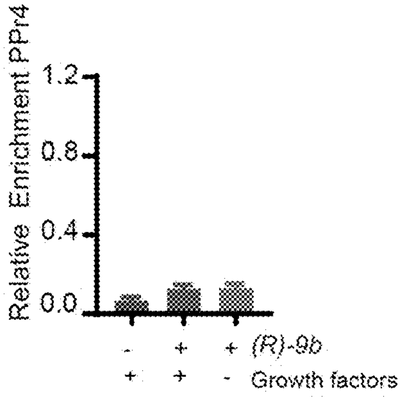
Figure 17F:
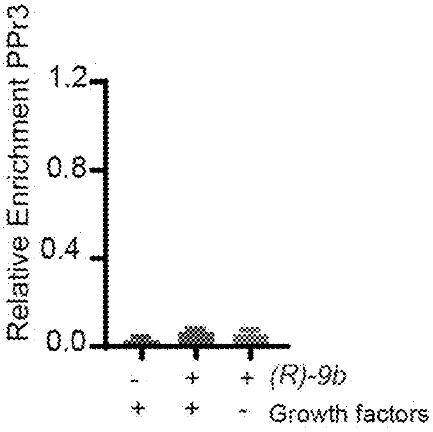
Figure 17G:
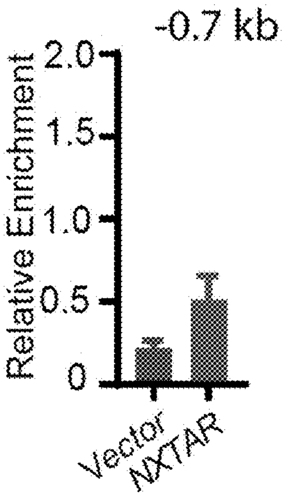
Figure 17H:
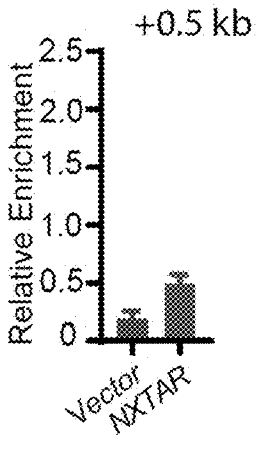
Figure 17I:
Figure 17J:
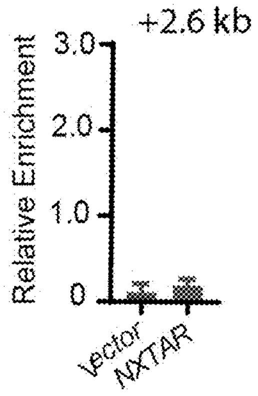
Figure 17K:
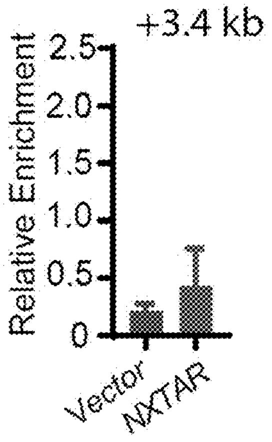
Figure 17L:
Figure 17M:
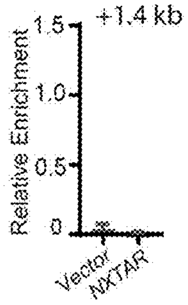
Figure 17N:
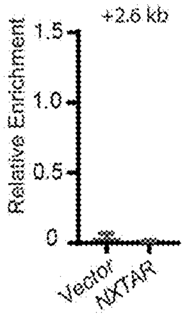
Figure 17O:
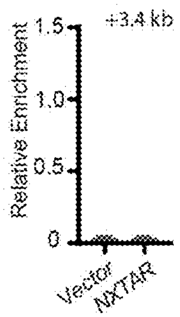
Figure 17P:
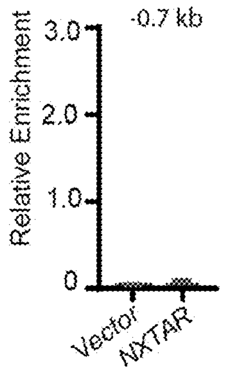
Figure 17Q:
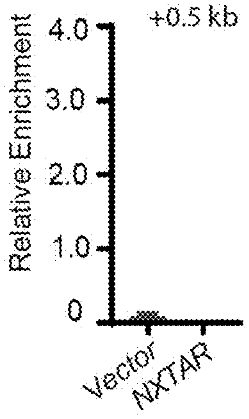
Figure 17R:
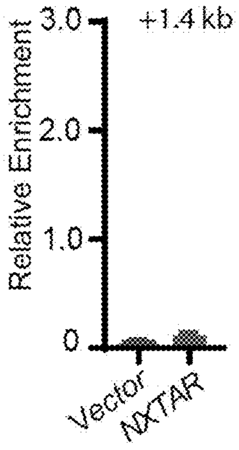
Figures 18A, 18B, 18C:
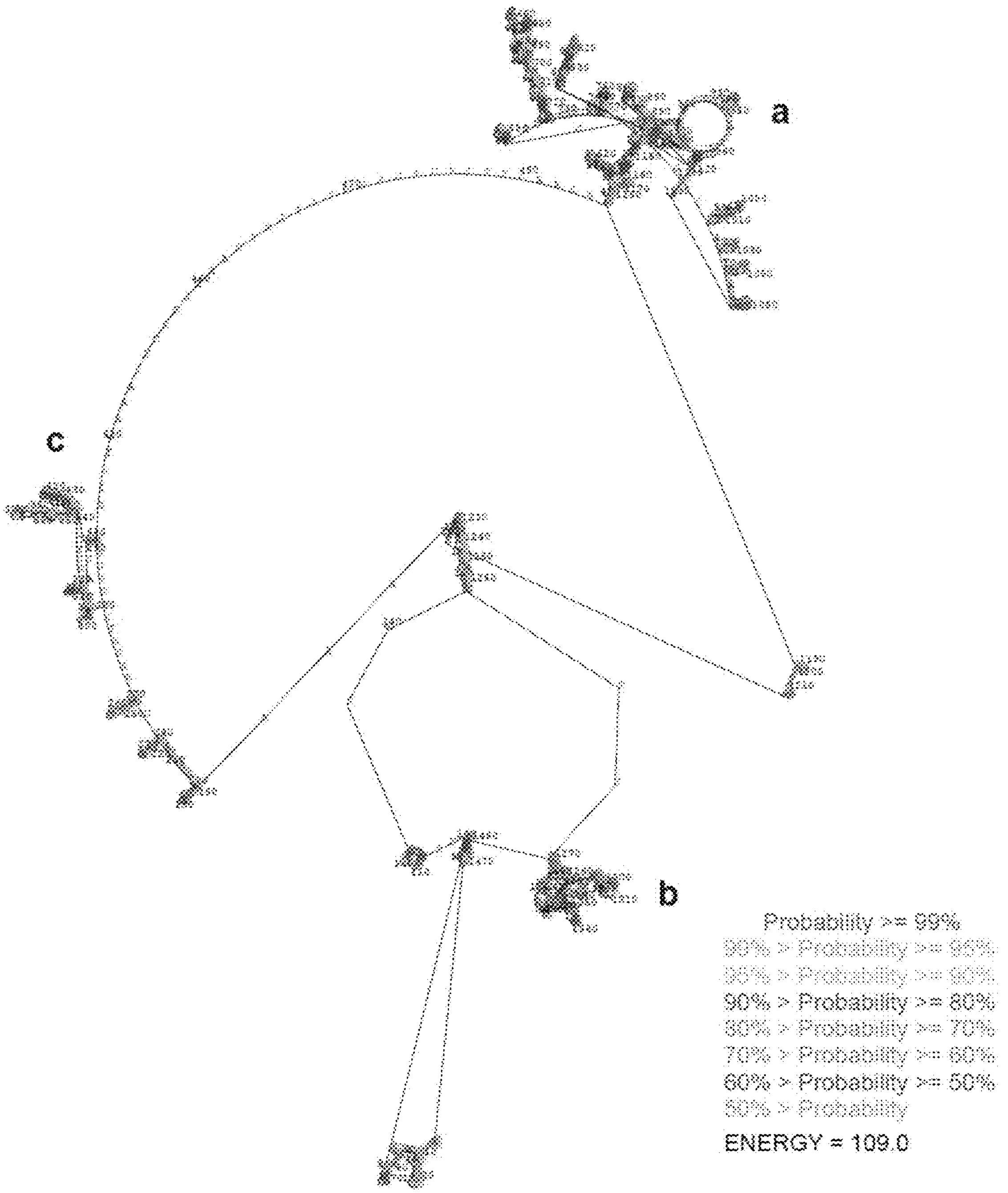
FIG. 18A-FIG. 18C. NXTAR secondary RNA structure. 'RNAstructure' MaxExpect generated high fidelity NXTAR RNA secondary structure composed of (A) 490-1180 nt, (B) 1270-1450 nt and (C) 290-440 nt regions that form distinct secondary structures with high probability of base pairing.

Inhibition of ACK1/AR Signaling Restores NXTAR Expression, Suppressing Prostate Tumor Growth To validate the role of AR, NXTAR expression levels were measured after depletion of AR levels in LNCaP, C4-2B, 22Rv1, and VCaP cell lines using AR siRNA (see e.g., FIG. 11A). A significant increase in NXTAR levels was seen in all PC cell lines after AR depletion (see e.g., FIG. 2A-FIG. 2D). Because withdrawal of growth factors also enhanced NXTAR upregulation, growth factor-regulated tyrosine kinase signaling may suppress NXTAR expression. To determine the role of a growth factor-regulated tyrosine kinase in suppressing NXTAR expression, ACK1 was focused on because of its regulation by multiple receptor tyrosine kinases (RTKs) such as insulin receptor, HER2, PDGFR, MERTK, and EGFR. ACK1, also known as TNK2, is a non-receptor tyrosine kinase whose protein levels (by SIAH-mediated ubiquitinylation) and activation are precisely regulated; a significant increase in its activation occurs as hormone-sensitive prostate cancer progresses to CRPC. Kinase screen revealed that Prostate cancer stem-like cells (PCSCs) depend on ACK1 for their survival. Recently, it was demonstrated that ACK1 regulates AR expression by epigenetically modifying the AR enhancer with a novel epigenetic mark: histone H4 Tyr88-phosphorylation. Recognizing the significance of ACK1/AR signaling, the ACK1 small molecule inhibitor (R)-9b was developed, which not only inhibited ACK1 kinase activity but also suppressed AR expression (see e.g., Mahajan et al. (2017) Cancer Cell and Lawrence et al. (2015) J Med Chem). LNCaP and 22Rv1 cells treated with (R)-9b exhibited robust increases in NXTAR levels in a dose-dependent manner (see e.g., FIG. 2E and FIG. 2F). Efficient knockdown of ACK1 was obtained using two distinct sets of siRNAs (see e.g., FIG. 2G). Knocking down ACK1 also led to significant induction of NXTAR levels in a time-dependent manner in LNCaP (see e.g., FIG. 2H) and 22Rv1 (see e.g., FIG. 2I) cells.

Figure 3A:
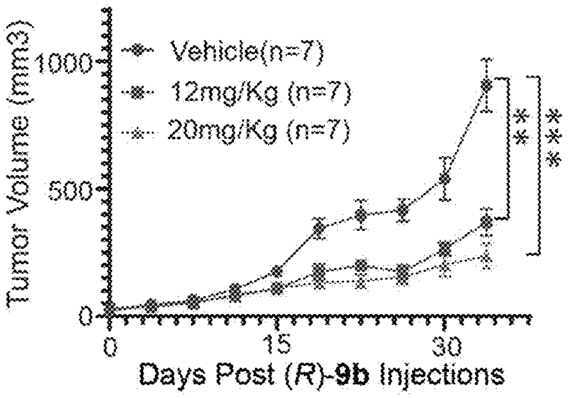
FIG. 3A-FIG. 3K. (R)-9b inhibits Enzalutamide-resistant CRPC xenograft tumor growth in vivo and induces NXTAR expression. (A) Enzalutamide-resistant VCaP cells were injected subcutaneously in castrated male SCID mice. Once the tumors were palpable the mice were treated with either Vehicle (Captisol; n=7) or (R)-9b at 12 mg/Kg (n=7) or 20 mg/Kg (n=7) subcutaneously, five times a week. (B, C) Tumor weights were recorded (B) and a photograph was taken (C). (D) Graph represents weights of the vehicle and (R)-9b treated mice. (E, F) Prostates (E) and brains (F) of the mice were harvested, RNA prepared, followed by qRT-PCR to determine the levels of the AR mRNA (n=4 each). (G-J) Tumors were harvested, RNA prepared, followed by qRT-PCR to determine the levels of the (G) AR, (H) KLK3, (I) TMPRSS2 mRNAs and (J) NXTAR (n=4 each). For (G-J) (n=4 each, 3 replicates). (K) Tumor lysates (n=3 tumors in each arm) were immunoblotted by AR, pAR, pACK1, ACK1 and Actin antibodies, as shown. Data (A, B and D-J) are represented as mean±SEM. $*p \leq 0.05$; $ p<0.01$; $*p<0.001$, two-tailed Student's t-test. NS, not significant.
Figure 3B:
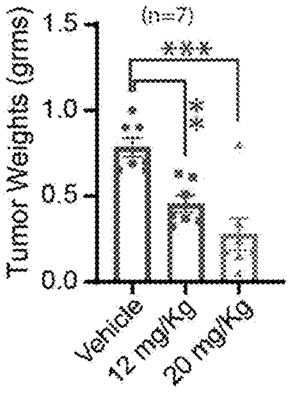
Figure 3C:
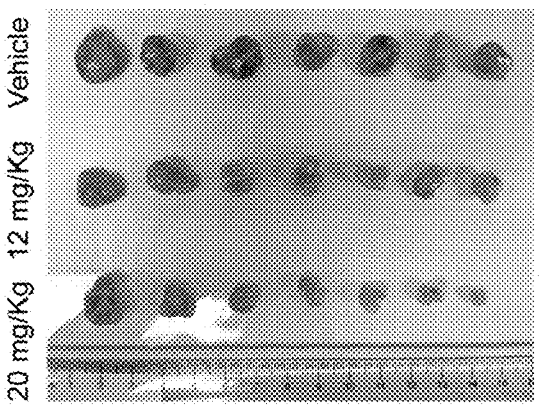
Figure 3D:
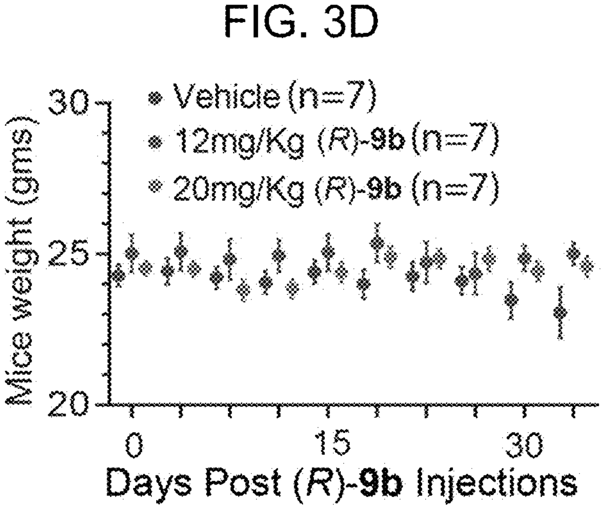
Figure 3E:
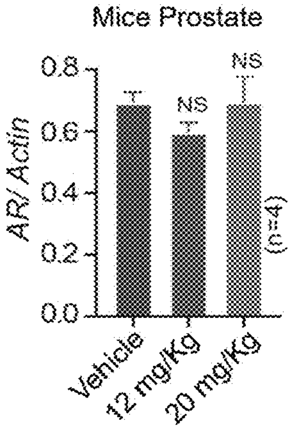
Figure 3F:
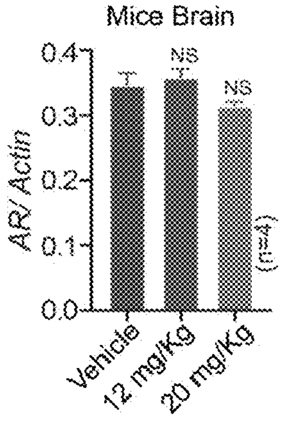
Figure 3G:
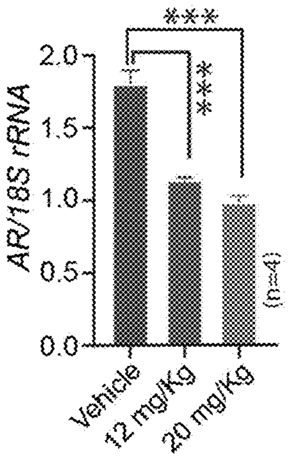
Figure 3H:
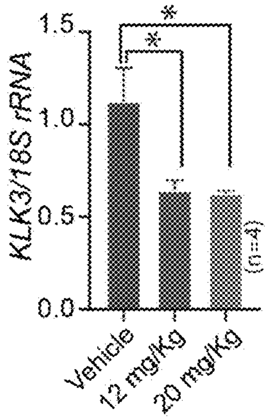
Figure 3I:
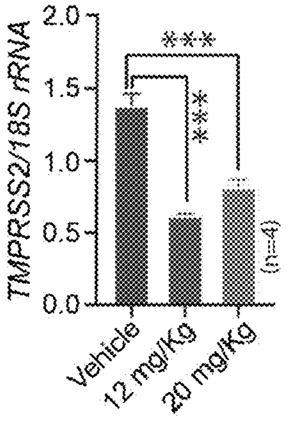
Figure 3J:
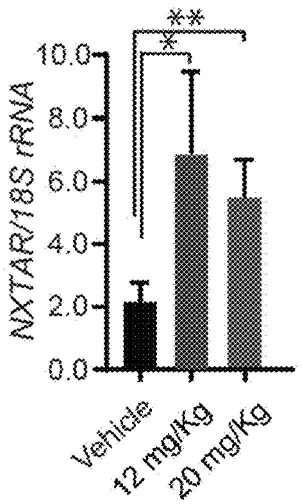
Figure 3K:
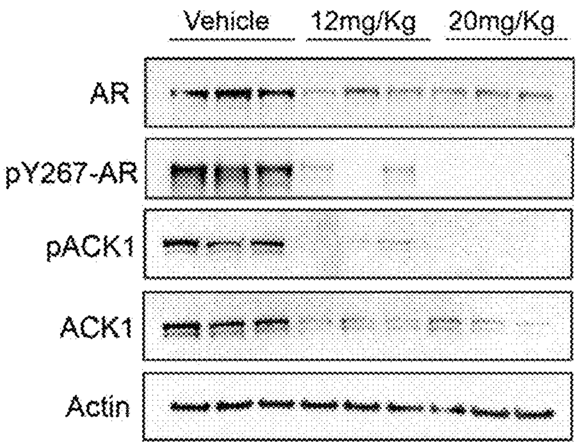

To assess whether restoration of NXTAR levels affected prostate tumor growth, enzalutamide-resistant VCaP cells were implanted subcutaneously in male severe combined immunodeficiency (SCID) mice. Once tumors became palpable, the mice were injected with either the vehicle (6% Captisol in PBS) or (R)-9b (12 or 20 mg/kg of body weight), five times a week. (R)-9b treatment significantly decreased tumor growth (see e.g., FIG. 3A-FIG. 3C). Further, no significant decrease in body weight was observed in (R)-9b-treated mice (see e.g., FIG. 3D) and no significant decreases in AR levels were noted in mice prostates or brain (see e.g., FIG. 3E and FIG. 3F). These data suggest that (R)-9b treatment does not have off-target effects in normal tissues and may not pass the blood-brain barrier. However, the xenograft tumors exhibited a significant reduction in AR and in mRNA levels of its target genes, KLK3 and TMPRSS2 (see e.g., FIG. 3G-FIG. 31). In contrast, a significant increase in NXTAR levels was observed in (R)-9b-treated tumors (see e.g., FIG. 3J). The immunoblotting of tumor lysates further confirmed loss of ACK1, phospho-ACK1, AR, and phospho-AR protein levels upon (R)-9b treatment (see e.g., FIG. 3K). Together, these data suggest that one possible mechanism underlying the significant loss of tumor growth upon overcoming ACK1/AR signaling is the restoration of the tumor-suppressor lncRNA NXTAR.

Increased H3K14 Acetylation on NXTAR Promoter Augments its Expression Upon ACK1 Inhibition H3K14ac is a hallmark of gene activation and is also present on bivalent promoters that are usually inactive but primed for activation if stimulus is presented. Levels of H3K14ac correlate with the CpG content of the promoters. Several families of histone acetyltransferase (HAT) have been reported to mediate acetylation of Lys14 of H3, including GCN5. To determine whether an increase in NXTAR upon ACK1 inhibition was due to an increase of H3K14ac deposition at its putative promoter, 22Rv1 and LNCaP cells were treated with (R)-9b alone or in combination with CPTH2, a selective GCN5 inhibitor. The significant increase in NXTAR levels observed following (R)-9b treatment was severely compromised by GCN5 inhibition in 22Rv1 and LNCaP cells (see e.g., FIG. 4A-FIG. 4C). It was tested whether this increase in NXTAR coincided with an increase in H3K14ac status in the NXTAR promoter region by designing primers for this region (designated Ppr3 and Ppr4) (see e.g., FIG. 4A). ChIP revealed a significant increase in H3K14ac mark deposition at these sites in (R)-9b-treated 22Rv1 and LNCaP cells, an increase that was abrogated when (R)-9b was combined with CPTH2 (see e.g., FIG. 4D, FIG. 4E, FIG. 11B, FIG. 11C, and FIG. 17A-17D). To further validate the role of GCN5 in deposition of H3K14ac marks, ChIP was performed using GCN5 antibodies, which revealed significant binding of GCN5 to the putative NXTAR promoter in (R)-9b-treated samples (see e.g., FIG. 4F, FIG. 4G, FIG. 11D, FIG. 11E).

Androgen deprivation or suppression of AR by siRNA or (R)-9b resulted in robust transcriptional activation of NXTAR (see e.g., FIG. 1A-FIG. 1M and FIG. 2A-FIG. 2I). Together with the significant GCN5 binding in (R)-9b-treated samples, AR and GCN5 may be competing for binding the same location in the NXTAR promoter. The binding of AR at Ppr3 and Ppr4 was compromised in cells that were deprived of the growth factors or subjected to (R)-9b treatment (see e.g., FIG. 4H, FIG. 4I, FIG. 11F, FIG. 11G, FIG. 17E, and FIG. 17F). These data indicate that a decrease in AR levels or activity could promote GCN5 occupation of the NXTAR promoter, upregulating its expression by deposition of H3K14ac marks.

Figure 4A:
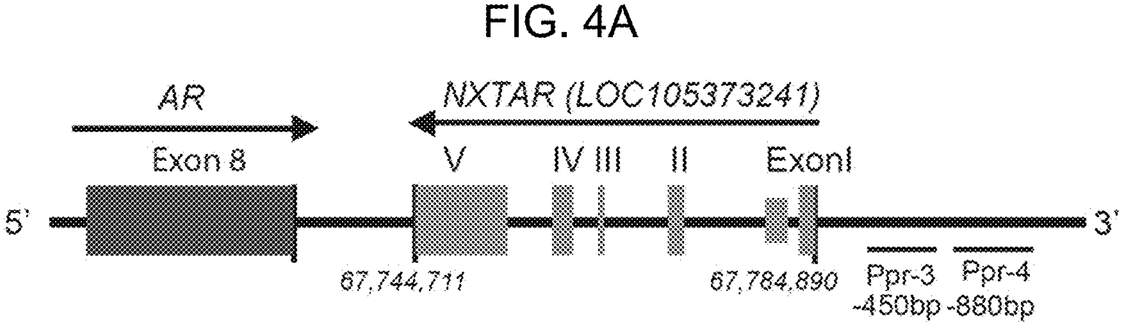
FIG. 4A-FIG. 4M. ACK1 inhibition induces NXTAR expression by increasing acetylation of H3K14 at NXTAR promoter. (A) Graphical representation of primers (Ppr3 and Ppr4) upstream of the NXTAR transcription start site. The numbers indicate nucleotide position. (B, C) 22Rv1 (B) and LNCaP (C) cells treated with either vehicle or (R)-9b alone or in combination with a GCN5 inhibitor, CPTH2 were processed for total RNA extraction and qRT-PCR was performed with primers for NXTAR and 18S rRNA. (D-E) 22Rv1 cells were treated with either vehicle or (R)-9b alone or in combination with CPTH2 and ChIP was performed using H3K14ac antibody or IgG (see e.g., FIG. 17A and FIG. 17B), followed by qPCR using (D) PPr4 and (E) PPr3 primers. (F, G) LNCaP cells treated with (R)-9b alone or in combination with CPTH2 were subjected to ChIP using GCN5 antibody or IgG (see e.g., FIG. 17C and FIG. 17D), followed by qPCR using (F) Ppr4 and (G) Ppr3 primers. (H, I) LNCaP cells were treated with either (R)-9b alone or in combination with CPTH2 were harvested and processed for ChIP using antibody against AR or IgG (see e.g., 17E and FIG. 17F), followed by qPCR using (H) PPr4 and (I) PPr3 primers. (J) 22Rv1 cells were treated with either vehicle or (R)-9b, subjected to ChIP using GCN5 antibody, followed by qPCR using IRF8 binding site primers. (K) VCaP cells were treated with either vehicle or (R)-9b, subjected to ChIP using NCOR1 antibody, followed by qPCR using NXTAR enhancer primers. (L) VCaP cells were transfected with control siRNA and three sets of NCOR1 specific siRNAs (1, 2, 3 and pool) and the cell lysate was subjected to immunoblotting. (M) RNA isolated processed from these cells was subjected to qRT-PCR using NXTAR and 18S rRNA specific primers. Data are represented as mean±SEM. $*p \leq 0.05$; $ p<0.01$; $*p<0.001$, two-tailed Student's t-test. NS, not significant.
Figure 4B:
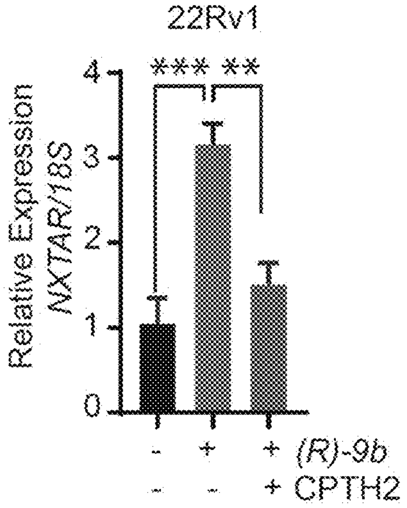
Figure 4C:
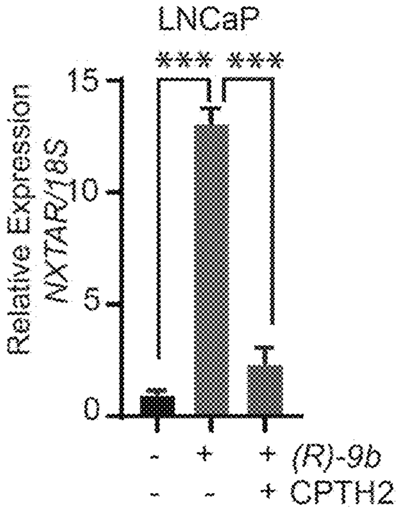
Figure 4D:
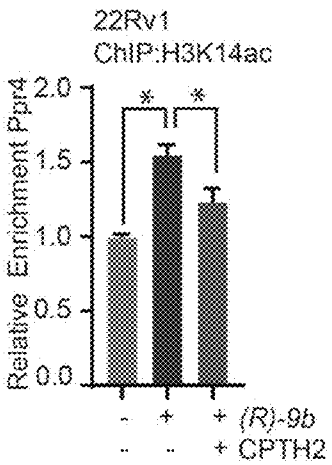
Figure 4E:
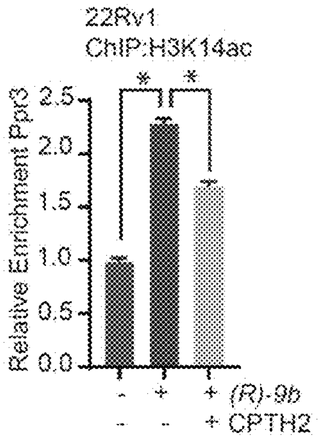
Figure 4F:
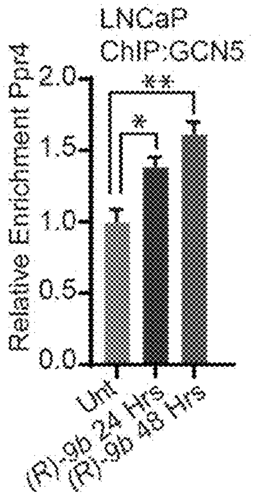
Figure 4G:
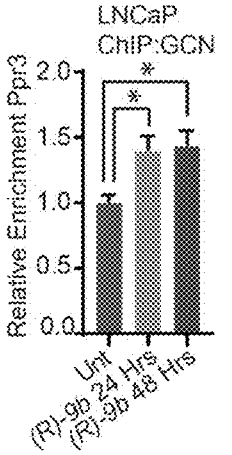
Figure 4H:
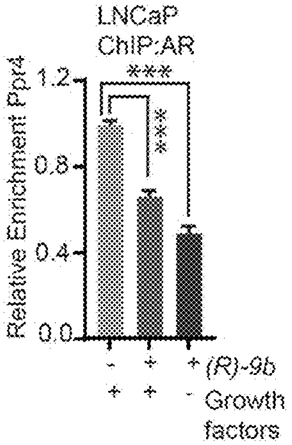
Figure 4I:
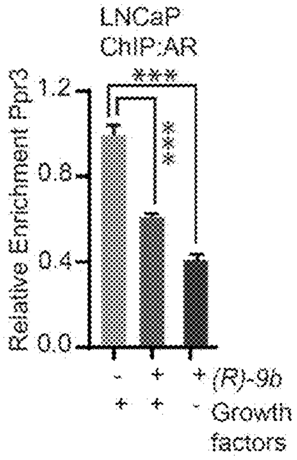
Figure 4J:
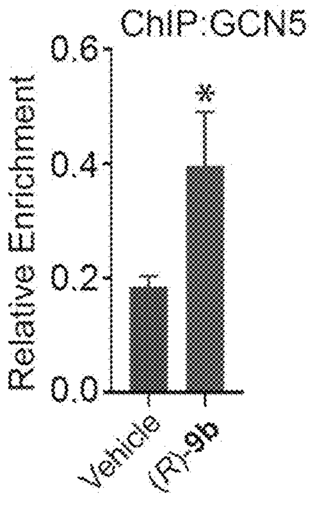
Figure 4K:
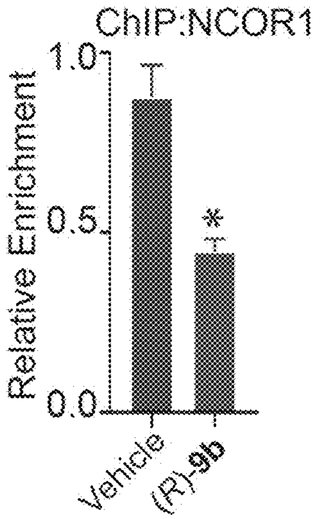
Figure 4L:
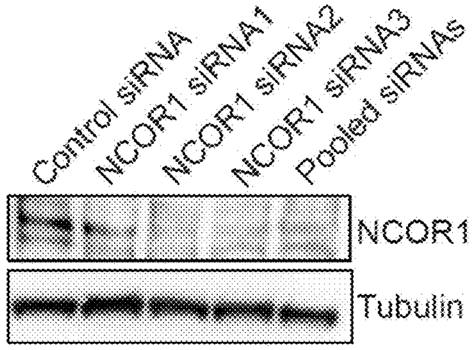
Figure 4M:
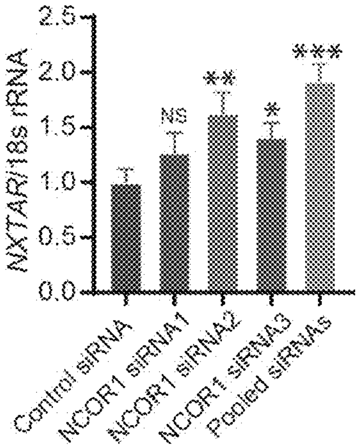
Figure 5A:
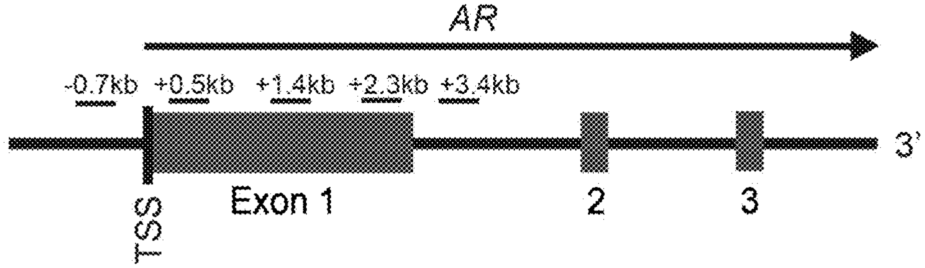
FIG. 5A-FIG. 5E. NXTAR over-expression causes an increase in repressive methylation on AR promoter. (A) Location of primers with respect to AR gene shown in a graphical format. (B) LNCaP cells were infected with either pBabe control vector or NXTAR expressing constructs and grown in androgen-free medium for 48 hrs. ChIP was performed using H3K27me3 antibody or IgG (see e.g., FIG. 17G-FIG. 17K and FIG. 17L-FIG. 17O), followed by qPCR using primers spanning regions upstream and downstream of AR TSS (−0.7 kb to +3.4 kb) as shown in (A). (C) LNCaP cells infected with pBabe or NXTAR expressing constructs and grown in androgen free medium for 48 hrs and ChIP was performed using EZH2 and IgG antibodies (see e.g., FIG. 17P-FIG. 17R), followed by qPCR. (D) Biotinylated oligos complementary to NXTAR (or lacZ as control) were used to pull down NXTAR from cell lysates prepared from VCaP cells retrovirally-infected to over-express NXTAR, followed by immunoblotting for EZH2. (E) VCaP cells were infected with NXTAR expressing construct and treated with EZH2 inhibitor, EPZ6438 (1 μM) overnight, followed by qRT-PCR. Data (B, C and E) are represented as mean±SEM. $*p \leq 0.05$; $ p<0.01$; $*p<0.001$, two-tailed Student's t-test.
Figure 5B:
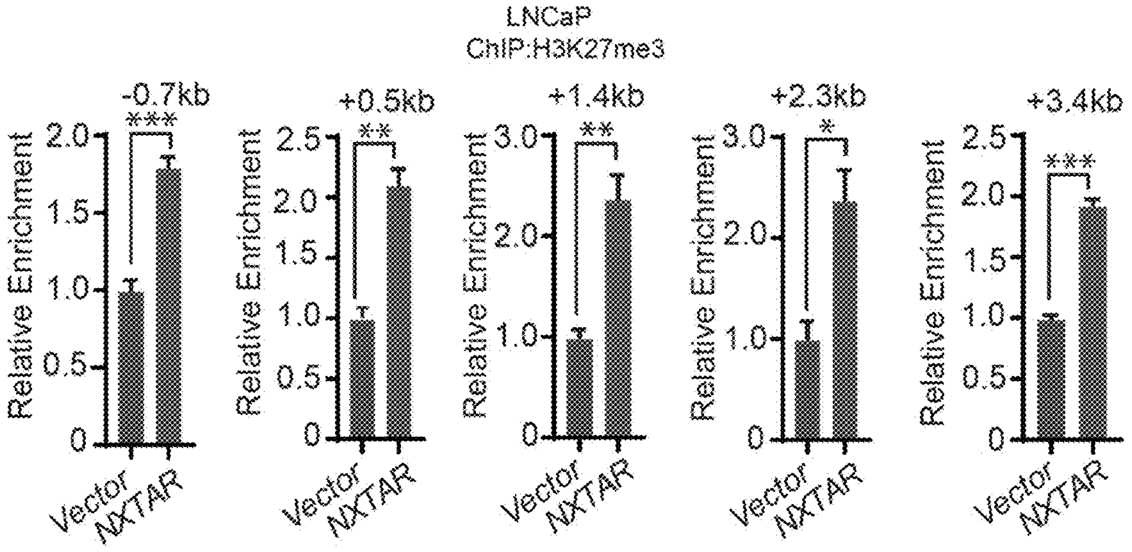
Figure 5C:
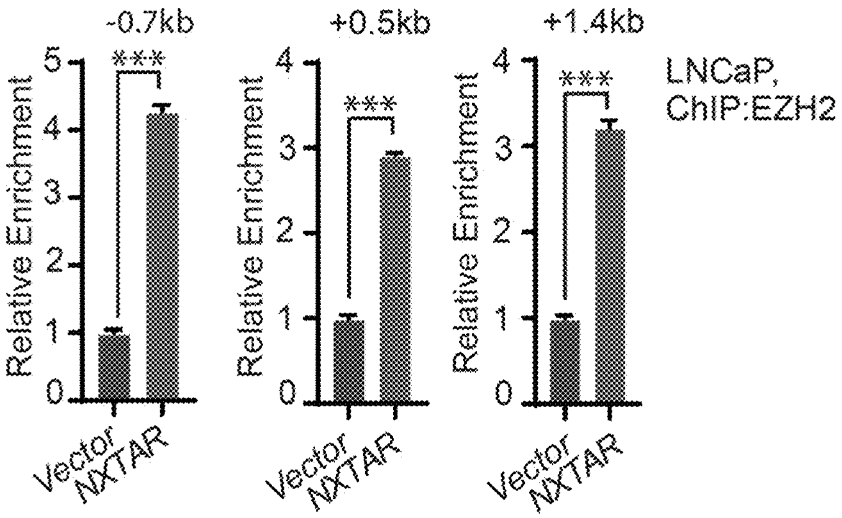
Figure 5D:
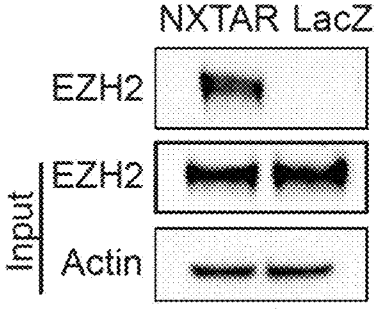
Figure 5E:
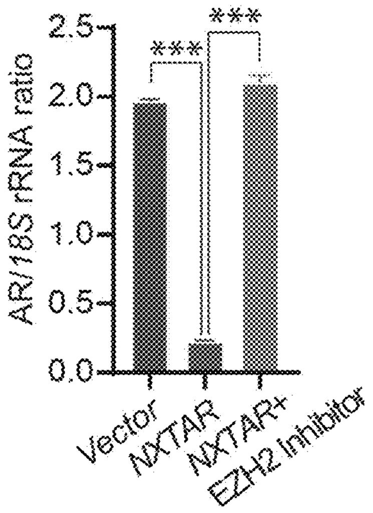
Figure 6A:
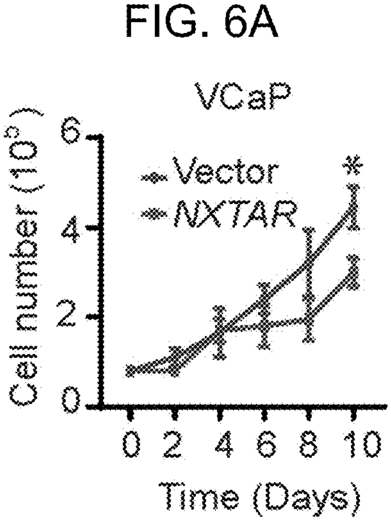
FIG. 6A-FIG. 6J. NXTAR restoration inhibits prostate cancer proliferation. (A, B) VCaP (A) and 22Rv1 (B) cells were infected with either pBabe vector or NXTAR expressing constructs and were seeded in androgen-deprived condition. Graph represents number of viable cells determined by trypan blue exclusion assay. (C, D) VCaP (C) and 22Rv1 (D) cells infected with pBabe vector or NXTAR expressing constructs were treated with either vehicle (10% DMSO) or enzalutamide for 9 or 5 days respectively, and viable cells were counted. (E) 22Rv1 cells infected with pBabe vector or NXTAR expressing constructs, treated with either vehicle (10% DMSO) or abiraterone for 5 days and the viable cells were counted. (F) 1.5 million VCaP cells that were infected either with pBabe or NXTAR vectors were implanted subcutaneously per SCID mice, and allowed to grow till they reached an average volume of ~1200 $mm^3$ for pBabe mice. (G-I) The tumors were excised, photographed (G) and the tumor weights (H) and volume (I) were recorded. (J) Tumor lysates (n=3 per group) were immunoblotted. Densitometry measurement is provided by the below the AR blot. Data are represented as mean±SEM. $*p \leq 0.05$; $ p<0.01$; $*p<0.001$, two-tailed Student's t-test. NS, not significant.
Figure 6B:
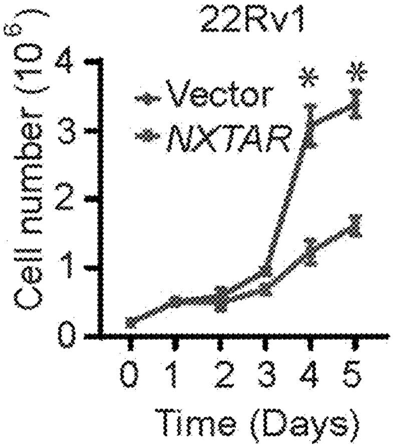
Figure 6C:
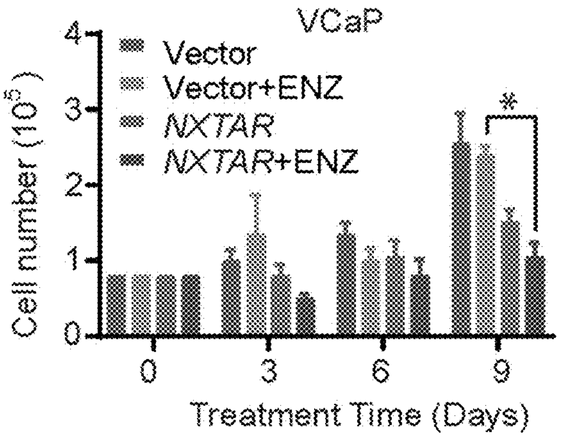
Figure 6D:
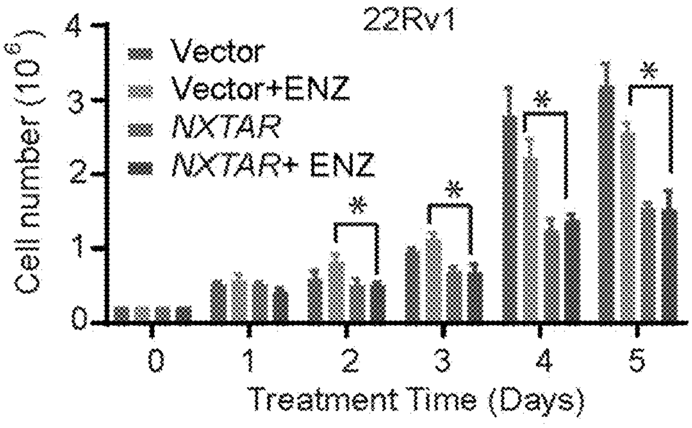
Figure 6E:
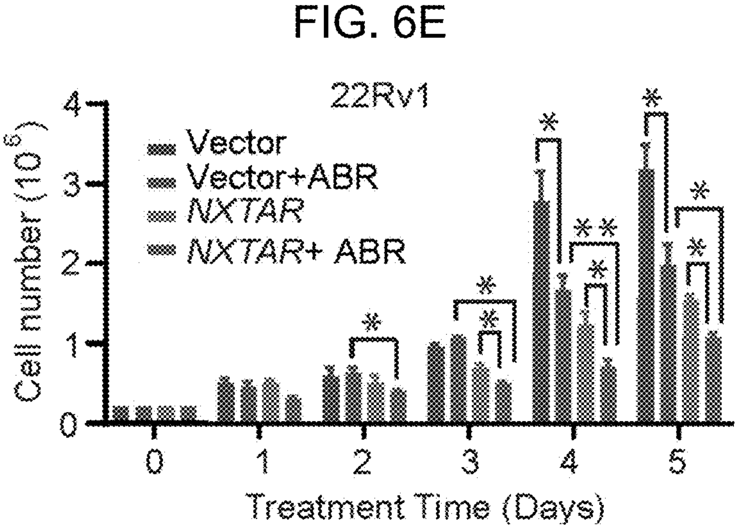
Figure 6F:
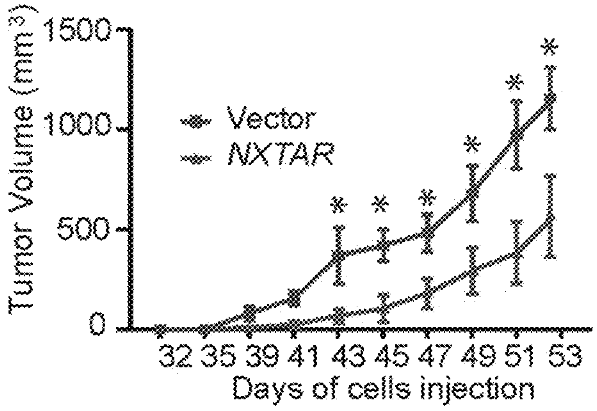
Figure 6G:
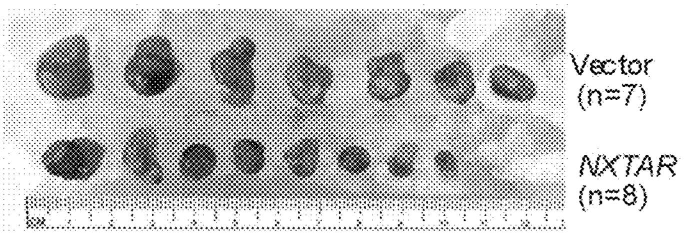
Figure 6H:
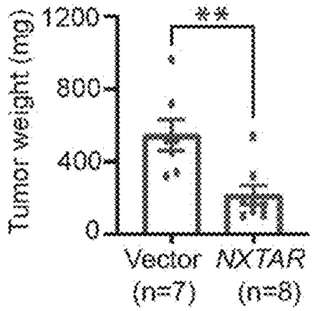
Figure 6I:
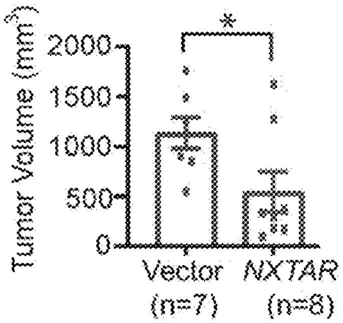
Figure 6J:
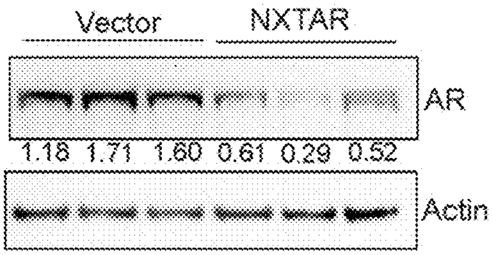

Nuclear Receptor Corepressor 1 (NCOR1) Recruitment Upstream of NXTAR Suppressing its Expression A distal intragenic enhancer was identified within the 1st intron of the NXTAR gene (chrX:67779247-67781971), using ENCODE (see e.g., FIG. 4A, blue box). Multiple transcription factor binding sites were noticed in this region, including Nuclear receptor corepressor) (NCOR1) which functions as corepressor for AR. NCOR contains a pair of SW13/ADA2/NCoR/TFIIB (SANT) domains. The N-terminal SANT is a critical component of a deacetylase activation domain (DAD) that binds and activates HDAC3, promoting histone deacetylation and transcriptional repression. Since inhibition of ACK1 leading to loss of AR levels reinstates NXTAR expression (see e.g., FIG. 2D-FIG. 2I), AR might recruit a corepressor such as NCOR1 to accomplish NXTAR suppression. To test this possibility, 22Rv1 cells were treated with (R)-9b, followed by ChIP with NCOR1 and GCN5 antibodies. qPCR with IRF8 binding site primers revealed increased GCN5 binding upon (R)-9b-treatment (see e.g., FIG. 4J). In contrast, qPCR with NXTAR enhancer region-specific primers revealed NCOR1 binding to this region, which was significantly decreased upon (R)-9b-treatment (see e.g., FIG. 4K). Further, transfection with NCOR1 siRNA2, 3 and pooled siRNAs exhibited significant downregulation of NCOR1 expression (see e.g., FIG. 4L), which was reflected in increased NXTAR expression (see e.g., FIG. 4M). Taken together with FIG. 4F-FIG. 4I and FIG. 11A-FIG. 11D, these findings uncover the molecular dynamics at NXTAR locus wherein NCOR1/AR keep NXTAR levels in check by assembling at the promoter/enhancer region, however, upon suppression of AR allows GCN5 binding to re-initiate transcriptional activity.

Epigenetic Silencing of AR Gene by NXTAR

BLASTN analysis revealed a sequence in exon 5 of NXTAR (the N5 region) with significant homology (in the complementary strand) to two regions of 30 and 43 nt separated by about 1607 nt in the AR promoter (see e.g., FIG. 12, FIG. 7A and FIG. 7B). These data open up the possibility that NXTAR could bind to the AR promoter, regulating its expression reciprocally. To test this hypothesis, a retroviral construct expressing NXTAR was generated and 22Rv1 and VCaP cells were infected. Upon restoration of NXTAR, a significant decrease in AR mRNA level was seen, which was also reflected in significant loss of expression of the AR target genes KLK3 and TMPRSS2 (see e.g., FIG. 13A and FIG. 13B). 22Rv1 cells expressed AR-V7, a variant derived from the AR locus which too was significantly compromised upon reintroduction of NXTAR (see e.g., FIG. 13A). AR protein was decreased upon NXTAR expression in a time-dependent manner in LNCaP and 22Rv1 cells (see e.g., FIG. 13C and FIG. 13D, respectively). This regulation of AR protein by NXTAR was further confirmed by its dose-dependent downregulation of AR in 22Rv1 cells (see e.g., FIG. 13F), in contrast, vector-transfected cells had no effect on AR levels (see e.g., FIG. 13E). Further to confirm functionality of LNCaP and 22Rv1 cells, qRT-PCR was performed; an increased AR and KLK3/PSA levels post-DHT-treatment was significantly compromised upon NXTAR restoration (see e.g., FIG. 14A-FIG. 14D).

To examine whether effect of ACK1 inhibitor on AR is mediated through ACK1, a "rescue" experiment was performed, wherein NXTAR overexpression caused significant loss of AR levels. However, when NXTAR expression was accompanied by activated ACK1 (caACK) expression, AR levels were restored (see e.g., FIG. 14E). As additional evidence for interdependence of AR and NXTAR expression in imparting Enzalutamide-resistance, AR and NXTAR levels were assessed in Enzalutamide treated VCaP cells. These cells are Enzalutamide-resistant and thus exhibited marginal decrease in AR levels, which is also reflected in no change in NXTAR levels (see e.g., FIG. 14F).

To understand precisely how AR transcript levels are suppressed by NXTAR, the epigenetic landscape of the AR promoter was examined. The histone-methyltransferase enhancer of zeste homolog 2 (EZH2), a subunit of PRC2, catalyzes H3K27 trimethylation (H3K27me3), leading to chromatin compaction and subsequent silencing of genes. ChIP with H3K27me3 antibodies followed by qPCR using the primers spanning the region (−0.7 to +3.4 kb) around the TSS of the AR gene (see e.g., FIG. 5A) revealed a significant increase in deposition of H3K27me3 marks in the AR promoter upon NXTAR restoration in LNCaP, 22Rv1 cells (see e.g., FIG. 5B, FIG. 15A, FIG. 15G-K and FIG. 15L-FIG. 15O) and VCaP cells (see e.g., FIG. 15C). To validate that the cause of H3K27me3 deposition is the binding of EZH2 at the AR promoter, ChIP was performed, revealing its significant binding in LNCaP cells overexpressing NXTAR (see e.g., FIG. 5C, and FIG. 16P-FIG. 16R). Similar observations were made in VCaP (see e.g., FIG. 15B) and 22Rv1 cells (see e.g., FIG. 15F-FIG. 15H). Further, (R)-9b treatment too caused a significant binding of EZH2 to the AR promoter in VCaP and 22Rv1 cells (see e.g., FIG. 15D, FIG. 15F-15H), reflecting in increased H3K27me3 levels (see e.g., FIG. 15E).

To explore the potential NXTAR binding to EZH2, RNA pull-down was performed, wherein DNA oligonucleotides complementary to NXTAR lncRNA (oligonucleotides complementary to lacZ as a control) were used to perform the pull-down of NXTAR RNA from VCaP cells (which was subjected to retroviral expression of NXTAR). Immunoblotting revealed that EZH2 could bind to NXTAR RNA, but not to the lacZ (see e.g., FIG. 5D). NXTAR pull-down was confirmed by qPCR (see e.g., FIG. 15I). Further, treatment with EZH2 inhibitor (EPZ6438) restored the AR expression (see e.g., FIG. 5E). To further assess NXTAR interaction with EZH2, 6×His tagged EZH2 construct, which was transfected in 293T cells. EZH2 was purified using nickel affinity chromatography (binding to Ni-NTA beads), followed by elution with imidazole. NXTAR immobilized on streptavidin beads when incubated with purified EZH2, exhibited considerable binding, which was not seen with the LacZ oligo. Since the in vitro RNA/protein binding assay was performed using tagged EZH2 purified from 293T cells, but not from bacteria, the possibility that NXTAR could bind to proteins associated with EZH2 in PRC2 complex, e.g., EED, SUZ12, JARID2, AEBP2, RbAp46/48, and PCL cannot be completely ruled out. Taken together, these data indicate that NXTAR could bind to the AR promoter, recruit PRC2 complex, leading to silencing of AR due to the H3K27me3 marking.

Restoration of NXTAR Mitigates Enzalutamide-Resistant Prostate Cancer Proliferation and Tumor Growth To test whether NXTAR had any effect on prostate cancer cell proliferation, 22Rv1 and VCaP cells were infected with a pBABE-puro vector or NXTAR-expressing constructs and selected using puromycin. In contrast to vector, severe loss of proliferation was seen upon NXTAR expression in VCaP (see e.g., FIG. 6A) and 22Rv1 (see e.g., FIG. 6B) cells. The loss of AR expression upon NXTAR expression was confirmed by immunoblotting (see e.g., FIG. 16A and FIG. 16B). A lncRNA that inhibits AR (and AR-V7) may limit the proliferation of AR antagonist-resistant prostate cancer cells. To test this hypothesis, VCaP and 22Rv1 cells expressing vector or NXTAR constructs were treated with enzalutamide, which did not result in a significant decrease in proliferation of either cell line, however, NXTAR expression significantly compromised proliferation upon enzalutamide treatment (see e.g., FIG. 6C and FIG. 6D). Interestingly, this reduction was comparable to that observed with NXTAR overexpression alone, suggesting that NXTAR expression causing loss of AR makes enzalutamide-mediated AR inactivation irrelevant. In addition to enzalutamide, another AR antagonist that has a different mode of action was assessed: abiraterone, which suppresses androgen synthesis. Although 22Rv1 cells are sensitive to abiraterone when it is used alone, NXTAR expression further sensitized them (see e.g., FIG. 6E). As a positive control, cells were treated with (R)-9b, which caused cell death in both cell lines (see e.g., FIG. 16C and FIG. 16D), suggesting that (R)-9b-mediated NXTAR upregulation is robust and could provide superior benefits compared with retroviral overexpression of NXTAR.

To examine the direct effect of NXTAR restoration on prostate tumor growth, equal numbers of VCaP infected with either pBABE vector or NXTAR constructs were injected in the SCID mice. Palpable tumors were formed around week 5 that were measured twice a week thereafter. Compared with mice injected with vector-expressing cells, mice injected with NXTAR overexpressing cells showed a significant reduction in tumor growth (see e.g., FIG. 6F). The tumor burden in mice injected with NXTAR expressing cells was significantly reduced compared with that of vector-transfected cells (see e.g., FIG. 6G-FIG. 61). Further, the NXTAR expressing tumors exhibited significant reduction in AR protein levels (see e.g., FIG. 6J).

Figure 7E:
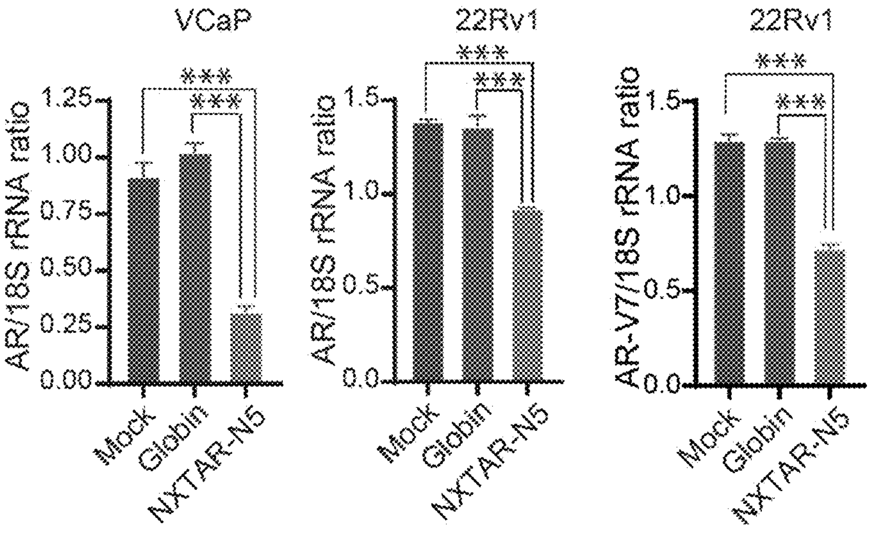
Figure 7F:
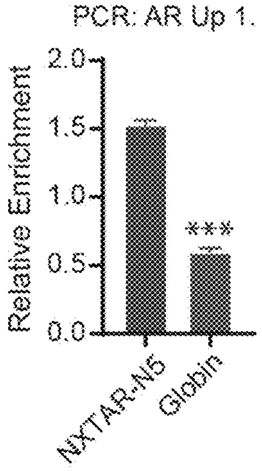
Figure 7G:
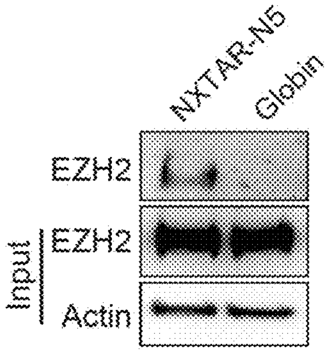
Figure 7H:
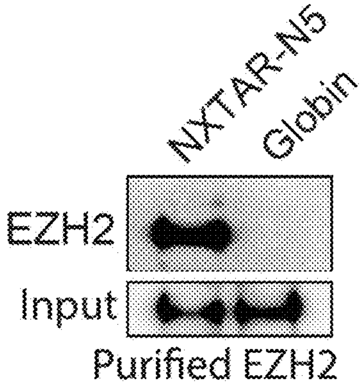
Figure 7I:
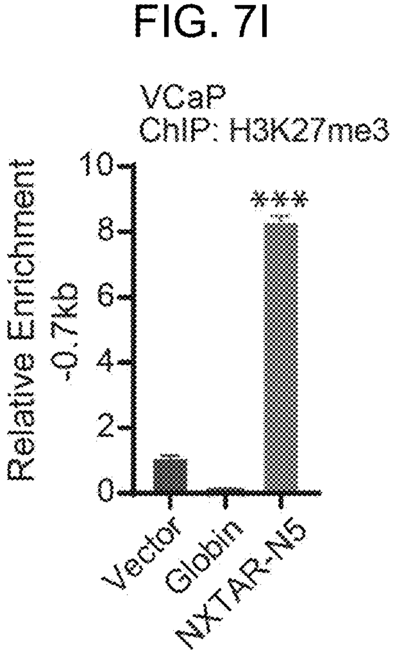
Figure 8:
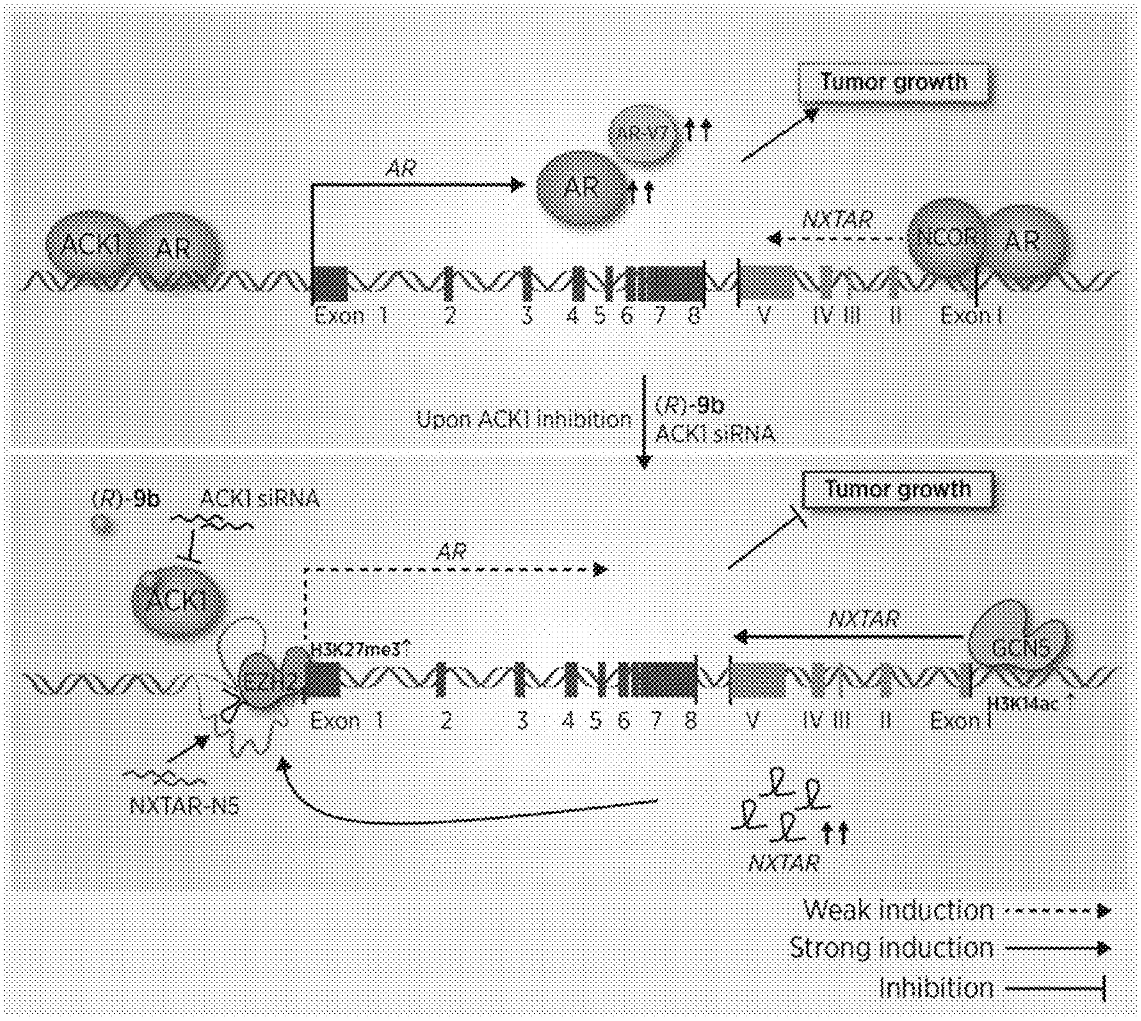
FIG. 8 is a schematic depicting the positive feedback loop discovered in this study, wherein NXTAR acts as a novel prostate tumor-suppressing lncRNA by inhibiting AR/AR-V7 expression, which in turn upregulates NXTAR levels.

NXTAR-N5 Oligonucleotide Derived from NXTAR Mitigates AR Expression and Prostate Cancer Cell Proliferation As described earlier, two regions of 30 and 43 nt upstream of the AR promoter were uncovered that have complementary sequences to the N5 region of exon V of NXTAR (see e.g., FIG. 12, FIG. 7A and FIG. 7B). Binding of NXTAR upstream of the AR promoter may hinder transcription (see e.g., FIG. 7A and FIG. 8). To test this hypothesis, an oligonucleotide was designed corresponding to the N5 region of exon V, designated NXTAR-N5 (see e.g., FIG. 7C). VCaP and 22Rv1 cells transfected with NXTAR-N5 exhibited a significant decrease in AR and AR-V7 transcription, which was also reflected in the compromised proliferation of these cells (see e.g., FIG. 7D and FIG. 7E). The bindings of NXTAR-N5 to the upstream of AR were validated; briefly, biotinylated-NXTAR-N5 oligo was immobilized onto streptavidin beads, incubated with VCaP lysate, followed by qPCR with the primer AR Up1.1 (see e.g., FIG. 7A). NXTAR-N5 bound upstream of AR, however, globin binding was significantly reduced (see e.g., FIG. 7F). In addition, NXTAR-N5 interaction with EZH2 was confirmed by performing pulldown as described above (see e.g., FIG. 7G). Moreover, NXTAR-N5 interaction with purified EZH2 (as described above) was confirmed by performing pulldown (see e.g., FIG. 7H). Furthermore, NXTAR-N5 introduction induced histone H3K27 methylation in the AR promoter region (−0.7 kb), which was confirmed by ChIP (see e.g., FIG. 7I).

Discussion

Overall, the results demonstrate that a novel tumor-suppressor lncRNA NXTAR, located close to the AR gene, suppresses AR expression by recruiting EZH2 methyltransferase and marking the AR promoter with H3K27me3 repressive epigenetic marks. The loss of AR, in turn, allowed GCN5 acetyltransferase to bind to the NXTAR upstream region, leading to deposition of H3K14ac epigenetic marks that enhanced NXTAR expression (see e.g., FIG. 8) To address how GCN5 is recruited, MotifMap, a web-based tool for genome-wide maps of regulatory elements, was used to scan the region between enhancer and promoter. It revealed a few distinct transcription factor sites (see e.g., TABLE 3); the first one was the IRF-8.

TABLE 3

Transcription factor binding sites between promoter and enhancer of NXTAR (MotifMap).

| Location | Strand | BBLS | BLS | NLOD | Z-Score | FDR | Motif ID | TF Name |
|---|---|---|---|---|---|---|---|---|
| chrX:67 782419 . . . 67782426 | − | 1.361 | 1.788 | 1 | 3.932 | 0.119 | 0 | IRF8 |
| chrX:67 782461 . . . 67782468 | + | 1.151 | 1.788 | 1 | 3.974 | 0 | 0 | MTF1 |
| chrX:67 782500 . . . 67782506 | + | 1.137 | 1.788 | 1 | 3.817 | 0.069 | 0 | MAFB |
| chrX:67 782750 . . . 67782756 | + | 1.329 | 1.887 | 1 | 3.989 | 0.029 | 0 | Neuro D |
| chrX:67 782750 . . . 67782756 | − | 1.329 | 1.887 | 1 | 3.989 | 0.029 | 0 | Neuro D |
| chrX:67 782789 . . . 67782795 | + | 1.539 | 1.887 | 1 | 3.817 | 0.048 | 0 | MAFB |
| chrX:67 783160 . . . 67783174 | − | 0.615 | 1.506 | 0.84 | 4.597 | 0.067 | 0 | TLX1::NFIC |
| chrX:67 783160 . . . 67783174 | − | 0.279 | 1.084 | 0.84 | 4.61 | 0.112 | 0.042549349343 | CTF1 |

TABLE 3-continued

Transcription factor binding sites between promoter and enhancer of NXTAR (MotifMap).

| Location | Strand | BBLS | BLS | NLOD | Z-Score | FDR | Motif ID | TF Name |
|---|---|---|---|---|---|---|---|---|
| chrX:67 783193 . . . 67783207 | − | 0.616 | 1.519 | 0.822 | 4.445 | 0.077 | 0.00725512273544 | TLX1::N FIC |
| chrX:67 783193 . . . 67783207 | − | 0.186 | 1.519 | 0.822 | 4.457 | 0.129 | 0.0605636788517 | CTF1 |
| chrX:67 783193 . . . 67783210 | + | 0.549 | 1.519 | 0.885 | 4.343 | 0.106 | 0 | NF-1 |
| chrX:67 783206 . . . 67783220 | − | 0.194 | 1.519 | 0.831 | 4.534 | 0.124 | 0.0512967868057 | CTF1 |
| chrX:67 783206 . . . 67783220 | − | 0.62 | 1.519 | 0.831 | 4.522 | 0.071 | 0 | TLX1::N FIC |
| chrX:67 783207 . . . 67783221 | + | 0.616 | 1.519 | 0.822 | 4.445 | 0.077 | 0.00725512273544 | TLX1::N FIC |
| chrX:67 783207 . . . 67783221 | + | 0.186 | 1.519 | 0.822 | 4.457 | 0.129 | 0.0605636788517 | CTF1 |
| chrX:67 783201 . . . 67783221 | + | 0.32 | 1.037 | 0.838 | 4.842 | 0.061 | 0 | ESR1 |
| chrX:67 783305 . . . 67783312 | − | 1.104 | 1.67 | 1 | 4.054 | 0.107 | 0 | MAFA |
| chrX:67 783307 . . . 67783313 | + | 1.294 | 1.67 | 1 | 3.817 | 0.061 | 0 | MAFB |
| chrX:67 783494 . . . 67783503 | + | 1.28 | 1.498 | 1 | 4.003 | 0.086 | 0.0257142288624 | PUR1 |
| chrX:67 783800 . . . 67783809 | + | 0.994 | 1.519 | 1 | 4.003 | 0.097 | 0.0316119802244 | PUR1 |
| chrX:67 784166 . . . 67784184 | − | 0.909 | 1.67 | 0.901 | 4.564 | 0.078 | 0.0348934375155 | NERF1a |
| chrX:67 784481 . . . 67784488 | − | 1.465 | 1.67 | 1 | 3.81 | 0.057 | 0 | ETS2 |
| chrX:67 784559 . . . 67784566 | + | 1.075 | 1.67 | 1 | 3.974 | 0 | 0 | MTF1 |
| chrX:67 784566 . . . 67784572 | − | 1.45 | 1.572 | 1 | 3.989 | 0.023 | 0 | Neuro D |
| chrX:67 784566 . . . 67784572 | + | 1.45 | 1.572 | 1 | 3.989 | 0.023 | 0 | Neuro D |
| chrX:67 784564 . . . 67784572 | + | 0.634 | 1.421 | 0.971 | 4.423 | 0.062 | 0 | HEB |

Interferon regulatory factors (IRFs) upon binding to a specific DNA element, also bind to coactivators such as HATs GCN5 and PCAF and become modified. ChIP with GCN5 clearly shows its binding to promoter (Ppr3/Ppr4 region) (see e.g., FIG. 4F, FIG. 4G and FIG. 11D-FIG. 11G) and adjoining IRF-8 binding region (see e.g., FIG. 4J). Taken together these findings reveal that NCOR1/AR assemble at enhancer/promoter region of NXTAR to maintain its low levels in prostate cancer, however, suppression of AR allows IRF-8 to recruit GCN5 to this newly vacated region, re-initiating NXTAR transcription. Significantly, this negative feed-forward NXTAR-AR circuitry seems to explain low levels of NXTAR in AR-positive prostate tumors or cancer-derived cell lines. Further, interruption of this circuitry by inhibition of AR expression using the ACK1 inhibitor, (R)-9b restored NXTAR levels, establishing the tumor-suppressor function of this lncRNA. Moreover, a significant loss of enzalutamide-resistant xenograft tumor growth was observed upon restoring NXTAR expression (see e.g., FIG. 6A-FIG. 6J). Overall, these data provide new insight into the mechanism by which prostate cancer cells maintain high AR levels continuously, i.e. suppression of NXTAR.

Figure 9E:
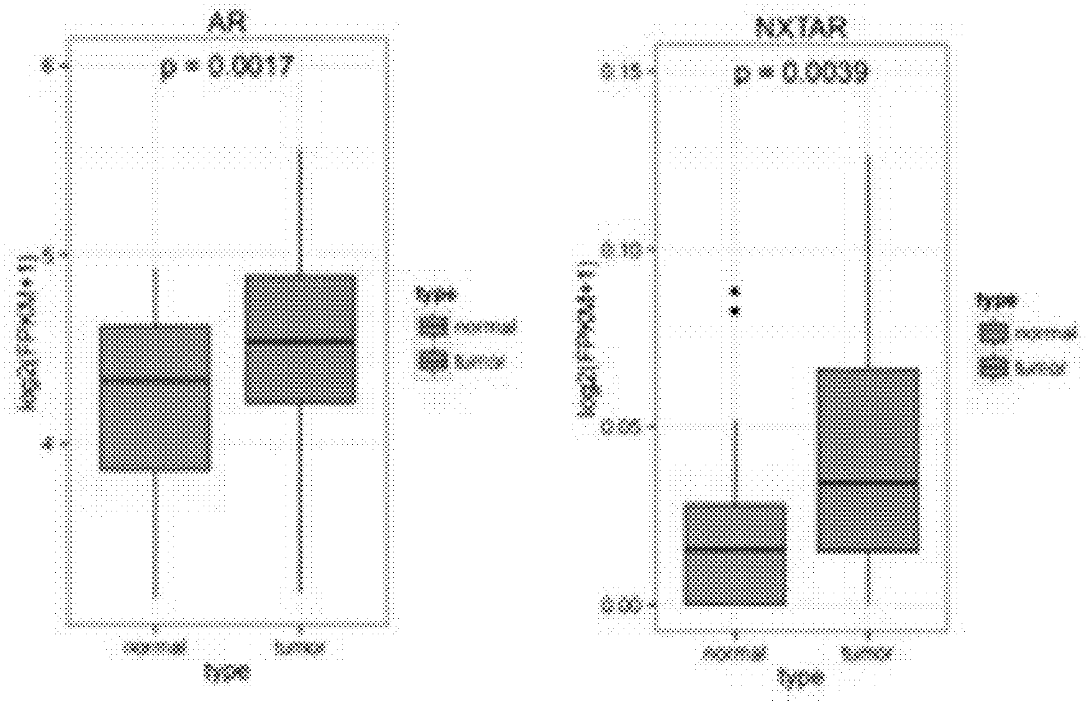

The downregulation of NXTAR in advanced prostate cancer was not observed in publically available databases (see e.g., FIG. 9E). Similar to other studies on lncRNAs e.g., HOTAIR in breast cancer, the correlation of expression with the lncRNAs and their target genes is not observed. There are several potential explanations. First, low expression of NXTAR made it hard to differentiate signal from noise in RNA-Seq data. While NXTAR was not differentially expressed in a patient cohort, a small subset of patients show a negative correlation between AR and NXTAR. Nonetheless, this data is inconclusive due to small sample size and therefore was not included. Second, the AR locus is one of the most complex loci in prostate cancer. AR expression is regulated by numerous genetic and epigenetic mechanisms. In prostate cancer (particularly in advanced patients), the AR locus is constantly altered. For example, the well-known genetic alteration in prostate cancer is amplification of the AR region that results in overexpression of AR and its nearby genes including NXTAR. Although, database analysis of PC patients shows a positive correlation of expression between AR and NXTAR, this observation, however, does not negate the negative regulation of AR by NXTAR as this may be one of the many ways AR is regulated. Importantly, this negative regulation has been shown in the tightly controlled experimental data presented herein where the only perturbation was NXTAR expression.

What is the region within NXTAR binding to EZH2 or its interacting proteins in PRC2 complex? The initial analysis suggests that there could be 2-3 contact points between NXTAR and EZH2. The 'RNAstructure' MaxExpect results generated a high fidelity NXTAR RNA secondary structure composed of highly probable base pairs, shown in FIG. 18A-FIG. 18C. It shows that (a) 490-1180 nt, (b) 1270-1450 nt and (c) 290-440 nt regions form distinct secondary structures with high probability of base pairing. Interestingly, these regions are also highly conserved in rhesus monkeys (TABLE 2). By virtue of high probability of base pairing and evolutionary conservation, these region/s may be involved in binding to PRC2 complex proteins.

Although at least 12 tumor-suppressor lncRNAs have been reported in androgen-dependent PC, only 3 have been shown to be involved in CRPCs: LINC00844, DRAIC, and PCAT29. LINC00844 was identified to be an AR-regulated lncRNA that is downregulated in metastatic prostate cancer. A tumor-suppressive locus on human chromosome 15q23 has recently been reported that contains two lncRNAs, DRAIC and PCAT29, both of which are suppressed by androgen-bound AR. In contrast, NXTAR is a distinct lncRNA, both functionally and spatially; unlike the others, (i) NXTAR is convergently paired tail-to-tail with the AR gene; (ii) it negatively regulates AR and AR-V7 expression; (iii) it is, itself, negatively regulated by AR; and (iv) its restoration overcomes AR and AR-V7, suppressing enzalutamide-resistant xenograft tumor growth. These unique qualities of NXTAR make it a highly desirable therapeutic target for recurrent prostate cancer, a stage that has become a major cause of PC-related mortality. Future studies involving restoration of NXTAR by using the small molecule inhibitor (R)-9b or NXTAR-N5 therapeutic oligonucleotide could provide long-term beneficial response in patients with CRPC.

What is claimed is:

1. A pharmaceutical composition comprising:

an isolated NXTAR-derived oligonucleotide having a sequence consisting of A*T*T*ATTATTTTAAATTTACAGAAGGGGAAACTAAGAATTATAGACATGAAGTGACT C*A*C*C (SEQ ID NO: 1) or a fragment thereof;

wherein the * represents a phosphorothioate bond modification and wherein the fragment thereof comprises at least 20 residues and includes at least one of the phosphorothioate bond modifications; and an ACK1/TNK2 inhibitor.

2. A kit comprising:

an isolated NXTAR-derived oligonucleotide having a sequence consisting of A*T*T*ATTATTTTAAATTTACAGAAGGGGAAACTAA GAATTATAGACATGAAGTGACTC*A*C*C (SEQ ID NO: 1) or a fragment thereof;

wherein the * represents a phosphorothioate bond modification and wherein the fragment thereof comprises at least 20 residues and includes at least one of the phosphorothioate bond modifications;

an ACK1/TNK2 inhibitor; and a pharmaceutical carrier.

3. The composition of claim 1, further comprising a pharmaceutically acceptable excipient or carrier selected from a nanoparticle, lipid, lipid nanoparticle, polymer, or peptide.

4. The composition of claim 1, wherein the ACK1/TNK2 inhibitor is (R)-9b.

5. The kit of claim 2, wherein the pharmaceutical carrier is selected from a nanoparticle, lipid, lipid nanoparticle, polymer, or peptide.

6. The kit of claim 2, wherein the ACK1/TNK2 inhibitor is (R)-9b.

* * * * *